US008653828B2

(12) United States Patent
Hancock et al.

(10) Patent No.: US 8,653,828 B2
(45) Date of Patent: Feb. 18, 2014

(54) APPARATUS FOR TREATING TISSUE WITH MICROWAVE RADIATION AND ANTENNA CALIBRATION SYSTEM AND METHOD

(75) Inventors: Christopher Paul Hancock, Bristol Avon (GB); Malcolm White, Bath and North East Somerset (GB); John Bishop, Bristol Avon (GB); Martin Wynford Booton, Wells Somerset (GB)

(73) Assignee: Medical Device Innovations Limited, Halton Cheshire (GB)

( * ) Notice: Subject to any disclaimer, the term of this patent is extended or adjusted under 35 U.S.C. 154(b) by 1023 days.

(21) Appl. No.: 12/311,553

(22) PCT Filed: Oct. 10, 2007

(86) PCT No.: PCT/GB2007/003827
§ 371 (c)(1),
(2), (4) Date: Jan. 6, 2010

(87) PCT Pub. No.: WO2008/043999
PCT Pub. Date: Apr. 17, 2008

(65) Prior Publication Data
US 2010/0121318 A1    May 13, 2010

(30) Foreign Application Priority Data
Oct. 10, 2006    (GB) .................................. 0620064.6
Aug. 31, 2007    (GB) .................................. 0717030.1

(51) Int. Cl.
*G01R 27/04*    (2006.01)
(52) U.S. Cl.
USPC ............................ 324/601; 324/638; 324/642
(58) Field of Classification Search
USPC .................. 324/601, 637, 638, 642, 533, 534
See application file for complete search history.

(56) References Cited

U.S. PATENT DOCUMENTS

| 6,815,947 B2 * | 11/2004 | Scheiner et al. ............... 324/230 |
| 7,339,382 B1 * | 3/2008 | Bray et al. ..................... 324/644 |
| 2003/0083654 A1 | 5/2003 | Ching |

FOREIGN PATENT DOCUMENTS

| WO | WO 0047282 | 8/2000 |
| WO | WO 2004/047659 | 6/2004 |
| WO | WO 2005/115235 A | 12/2005 |

* cited by examiner

*Primary Examiner* — Vincent Q Nguyen
(74) *Attorney, Agent, or Firm* — Arent Fox LLP

(57) ABSTRACT

A calibration method and apparatus for surgical antennas which are arranged to deliver microwave radiation (e.g. having a treatment frequency of 500 MHz to 100 GHz) into biological tissue is disclosed. An emitting region of the antenna is exposed to a plurality of calibration standards each having a different complex impedance at the treatment frequency. In one embodiment the calibration standards are created in a short-circuit-terminated waveguide cavity of variable length. In another embodiment, each calibration standard is a different mixture of two or more liquids. Measurement of the magnitude and phase of signals reflected from the emitting region when exposed to the calibration standard can permit calibration of the antenna, e.g. by generating a mapping function based on the measured values and known or reference values for the calibration standards. Also disclosed is tissue treatment apparatus having an ablation channel for conveying microwave radiation to a surgical antenna at a high power level and a separate measurement channel for conveying microwave radiation to a surgical antenna at a low power level, wherein the measurement channel bypasses noisy components on the ablation channel. A surgical antenna having an impedance transformer for matching an e.g. coaxial feed structure which terminates in one or more radiating elements with tissue to be treated is also disclosed.

15 Claims, 43 Drawing Sheets

Voltage multiplier for forward signal $\Gamma_1 = \alpha^2 \Gamma_2$

Voltage multiplier for forward signal $\Gamma_1 = \Gamma_2$

Voltage multiplier for backward signal for $\Gamma_1 = \alpha^2 \Gamma_2$

Voltage multiplier for backward signal for $\Gamma_1 = \Gamma_2$

Reflection amplitude at end of probe
Peak voltage multiplier for $\Gamma_1 = \alpha^2 \Gamma_2$ Reflection amplitude at end of probe
Peak voltage multiplier for $\Gamma_1 = \Gamma_2$

US 8,653,828 B2

APPARATUS FOR TREATING TISSUE WITH MICROWAVE RADIATION AND ANTENNA CALIBRATION SYSTEM AND METHOD

CROSS-REFERENCE TO RELATED APPLICATION

This application is a National Stage entry of International Application No. PCT/GB2007/003827, having international filing date of Oct. 10, 2007, which claims priority to GB Patent Application No. 0620064.6 filed Oct. 10, 2006, and GB Patent Application No. 0717030.1 filed Aug. 31, 2007, the disclosure of each of which is hereby incorporated in its entirety by reference.

TECHNICAL FIELD

The invention relates to the treatment of biological tissue using microwave radiation. In particular aspects, the invention concerns a surgical antenna for delivering microwave radiation to tissue, a tissue treatment system for carrying out ablation or measurement of tissue using microwave radiation from such an antenna, and a system and method of calibrating an antenna for use in such a system.

BACKGROUND TO THE INVENTION

An electrosurgical system that is arranged to controllably ablate a tumour and/or measure information concerning the tumour and surrounding healthy tissue is known. Such a system may use two channels: a first channel to perform controlled tissue ablation, and a second channel to perform sensitive tissue state (dielectric) measurements. The general principles relating to the operation of such a system are disclosed in WO 2004/047659 and WO 2005/115235.

SUMMARY OF THE INVENTION

This disclosure comprises three main aspects. The first aspect relates to a system and method for calibrating surgical antennas at the point of radiation (the aerial), and in particular to performing the calibration routine automatically when the calibration systems are used in conjunction with an electrosurgical system e.g. of the known type. The second aspect relates to further improvements to the known treatment system, which improvements offer significant advantages in terms of enhanced measurement sensitivity and reduced power levels required in the measurement mode due to the use of a separate low power transmitter and receiver (transceiver). The third aspect relates to surgical antennas that may be used with the calibration system to enable said antennas to be calibrated at the distal end (the aerial) thereby to enable said antennas to be used to perform tissue state measurements or to be used to ablate tissue where it is desirable to perform dynamic impedance matching between the distal tip of the antenna (the aerial) and the biological tissue load.

Calibration System and Procedure

At its most general, the first aspect of the invention may provide calibration apparatus for an antenna that is arranged to emit microwave radiation from an emitting region thereof, the apparatus having: a loading arrangement adapted to subject the emitting region of the antenna to a plurality of impedances, each impedance having a known value for a predetermined frequency of microwave radiation, a detector arranged to measure the magnitude and phase of microwave radiation having the predetermined frequency that is emitted from the antenna and reflected from the loading arrangement, and a processing unit configured to generate calibration data for the antenna, wherein, if the antenna is used subsequently to measure magnitude and phase of microwave radiation having the predetermined frequency with an unknown load at the emitting region of the antenna, the calibration data is usable to convert the measured magnitude and phase to be representative of the unknown load.

Preferably, the loading arrangement includes a substantially lossless waveguide cavity between a first end adapted to receive the emitting region of the antenna and a second end, and wherein a distance between the first end and the second end is variable. For example, the second end may be slidable relative to the first end, e.g. under the action of a linear actuator.

Preferably, the cavity is electrically connectable to the antenna and the second end electrically connected to the cavity. The electrical connection between the cavity and antenna and/or between the cavity and the second end may be through a radio frequency (RF) choke.

Preferably, the plurality of impedances include $0\Omega$ (short circuit) and $\infty\,\Omega$ (open circuit).

Preferably, the loading arrangement is adapted to permit generation of calibration data for two or more different frequencies of microwave radiation.

In another expression, the first aspect of the invention may provide a combination of calibration apparatus according to any preceding claim and an antenna arranged to emit microwave radiation from an emitting region thereof, wherein at least the emitting region of the antenna and the loading arrangement are packaged together in a sterile environment.

In yet another expression, the first aspect of the invention may provide a method of calibrating an antenna that is arranged to emit microwave radiation from an emitting region thereof, the method comprising: subjecting the emitting region to a plurality of impedances, each impedance having a known value for a predetermined frequency of microwave radiation, for each impedance: emitting microwave radiation having the predetermined frequency through the antenna; measuring the magnitude and phase of the emitted microwave radiation that is reflected from the loading arrangement; and generating calibration data for the antenna from the magnitude and phase measured for each of the plurality of impedances, whereby, if the antenna is used subsequently to measure magnitude and phase of microwave radiation having the predetermined frequency with an unknown load at the emitting region of the antenna, the calibration data is usable to convert the measured magnitude and phase to be representative of the unknown load.

The ability to effectively perform antenna calibration at the emitting region (e.g. distal tip) may enable efficient microwave energy transfer into biological tissue, where the impedance presented to the distal tip of the surgical antenna changes as the treatment process progresses. Once the antenna structure has been calibrated, it is then possible to perform accurate dynamic tuning adjustment to enable the distal tip of the antenna structure to be impedance matched with the changing impedance of the biological tissue. The ability to perform impedance matching between the distal tip of the surgical antenna and the biological tissue can prevent reflection of energy due to impedance mismatch, which can cause excessive heating of antenna and cable assemblies and increase the time required to perform ablation of a volume of tissue. In applications where the antenna is used in minimally invasive surgery this heating may cause to collateral damage to healthy tissue structures. A further advantage is that the dosage of energy delivered into biological tissue can be controlled with greater accuracy than that possible using a system where unquantifiable reflections due to impedance mismatches cannot be compensated for. For the implementation of this feature it is preferable for this invention to be used with a method of performing dynamic impedance matching. A system to perform such impedance matching using a three stub waveguide cavity tuner, where the stubs are automatically moved using three linear motors and a suitable control system has been disclosed in WO 2004/047659.

The ability to effectively perform antenna calibration at the distal tip may also enable the surgical antenna to be used as a useful tool for measurement of dielectric information relating to the properties of the biological tissue. Effective calibration at the distal tip of the surgical antenna enables the measurement reference plane to be moved to the exact site (or location) where the measurement is to be performed, for example at the periphery between healthy tissue and cancerous tissue, or inside the cancerous tissue. The ability to calibrate surgical antennas in this way can enable optimal measurement sensitivity to be achieved.

Therefore, the current invention can be used to enable dynamic impedance matching to be performed, and can be used to enable sensitive and repeatable dielectric measurements to be made. The current invention relates primarily to the calibration of surgical antennas, but the invention is not limited to calibrating these devices.

The calibration system disclosed herein effectively connects the distal, tip of the antenna to a plurality of load impedances between open circuit (infinite impedance) and short circuit (zero impedance) values to enable the antenna to have the capability of being able to measure or be sensitive to a range of impedances between the two extremes. The distal tip of the antenna may be automatically subjected to a range of impedances. Methods of automating the measurements are disclosed herein.

Preferably, the antenna calibration system uses a sliding short with the antenna fixed in position. RF chokes may be included to enable the antenna and the sliding short to be loosely fitted inside the cavity.

In this specification microwave means the frequency range of between 500 MHz and 100 GHz. However, frequencies between 14 GHz and 15 GHz are preferred, and a spot frequency of 14.5 GHz is used in some embodiments discussed below.

Although the primary purpose of the invention is to calibrate antennas for use in tissue ablation and measurement, the invention is not limited to this application. Indeed, the invention may be used wherever the measurement location is at the distal tip of an antenna arrangement. Put in another way, the invention may permit all systematic errors that are present between the distal tip of the antenna (the aerial) and the digital signal processing unit to be cancelled out, thus enabling the tissue load to be effectively connected to the digital signal processing unit. This may take into account variations in the components within the microwave transceiver, for example, thermal noise or short noise produced by low noise amplifiers, driver amplifiers, microwave frequency, mixers and PIN diode switches and attenuators.

It may be desirable to calibrate at more than one frequency where a first frequency is used for controlled ablation and a second frequency is used to perform dielectric measurements (tissue type/state, etc). For example, it may be desirable to calibrate an antenna structure over a frequency range of +/−50 MHz around a spot frequency of 14.5 GHz or it may be desirable to use other frequencies within the microwave or RF region of the electromagnetic spectrum. The dimensions of the calibration system (or assembly) can be adjusted to accommodate any practicable frequency (or range of frequencies) where the underlying theory related to the current invention remains valid. Due to the dynamic tuning mechanism used in the system (e.g. of the type described in WO 2004/047659), it may be necessary to calibrate at the ablation frequency. In this mode of operation, information concerning the state of the ablated tissue is used to automatically control the impedance matching mechanism to ensure that maximum power (or the demanded power) is delivered into the tissue load seen by the distal tip of the antenna. In a particular arrangement given in WO 2004/047659, four directional couplers are used to measure the forward and reflected power signals and this information is used as the basis upon which the dynamic impedance matching method is implemented. It may, for example, be desirable to perform tissue ablation at 10 GHz and make dielectric measurements at 16 GHz. In the instance where it is necessary to calibrate the system at two or more frequencies, it is desirable that all the frequencies can propagate inside the microwave structure, i.e. in the case of using rectangular or cylindrical waveguide, the waves should not be cut-off. It may also be desirable to include more than one transceiver unit in the system when more than one frequency is used and there is a large difference between the two frequencies, for example a 10 GHz difference. Higher order modes may also propagate when the wavelength of the calibration frequency signals are small compared with the size of the waveguide or co-axial calibration assembly. These effects may be taken into account by performing a system analysis to model the effects of higher order modes set up in the cavity. This may not be needed when the same frequency is used for ablation and measurement because a standard waveguide can be used which enables the relevant frequency to propagate unimpaired (e.g. for 14 GHz, WR62 (WG18) or WR75 (WG17) may be used).

The tissue ablation/measurement systems disclosed e.g. in WO 2004/047659 and WO 2005/115275 provide for impedance (or energy) matching between the surgical treatment antenna and the tissue load, and for the antenna to be capable of measuring small changes in complex impedance to enable characterisation of various tissue types, tissue states and/or stages associated with the growth of cancerous tumours to be measured. The present invention aims to improve the operational efficiency of those systems by providing for the calibration of the surgical antenna to take place at the distal tip where the antenna will radiate energy into tissue. In order to ensure that the widest possible range of impedances can be measured, it is desirable for the calibration system to be capable of locally presenting the antenna with a range of known impedances between open circuit and short circuit conditions. It is further desirable for the calibration procedure to be automated.

The antenna may be a surgical antenna or any other type of antenna structure, or other device. The invention is of particular use where the design of said antenna (or other device) does not lend itself to be connected to a standard co-axial calibration arrangement, for example, a co-axial (or waveguide) 50Ω load, and/or a co-axial (or waveguide) short circuit, and/or a co-axial (or waveguide), open-circuit, and/or a co-axial (or waveguide) sliding load. The calibration system described herein enables the reference plane for calibration to be moved to the distal tip of the antenna and takes into account the shape and geometry of the antenna structure to be calibrated.

Preferably, a range of calibration positions can be obtained by moving a sliding short circuit, connected to an electromechanical linear actuator, in such a manner that the sliding short (or plunger) starts at the short circuit position on the Smith chart and as the plunger is withdrawn from the waveguide cavity, the impedance moves around the outer circle (assuming a lossless cavity) where one or more calibration points can be measured. If the cavity is substantially lossless then there may be no real component present and so the complex impedance will either be an inductive reactance or a capacitive reactance. Such an arrangement forms a particular aspect of the current invention and is addressed in detail below. The calibration can be represented on a Smith chart or in other forms, e.g. a polar chart, phase/magnitude plots or another suitable measurement plane.

Due to the need to accurately measure both the phase and magnitude of information in terms of impedance seen at the distal end of the treatment/measurement antenna, it is desirable to calibrate the surgical antenna at the point where tissue state (dielectric) measurements are to be made. If the antenna is not calibrated at the distal tip (where it connects to the tissue load) then it is more difficult to measure the value of impedance presented to the distal tip, and it will be difficult to make valid and repeatable measurements of tissue impedances and/or be able to differentiate between various tissue types. Phase and magnitude variations associated with the components that form the transmission path between the measurement instrumentation (generator) and the distal tip of the antenna make it difficult to theoretically determine the exact phase and magnitude of the signal at the distal end of the antenna seen at the generator end, where the microwave transceiver and signal processing circuitry is located. The components in the path may include: microwave connectors and interconnects, a flexible cable assembly, a length of rigid co-axial cable that forms a part of the antenna (this is inserted inside the body), the antenna (aerial) itself, the tuning unit, the microwave signal mixers, various co-axial couplers, semi rigid or flexible semi rigid assemblies, low noise amplifiers, drive amplifiers, microwave circulators and other components within the microwave transceiver line-up. Due to the short wavelengths associated with microwave frequencies, it is very difficult to calculate or quantify the phase at the distal end of the antenna, for example the free space wavelength at 14.5 GHz is 20.69 mm, thus a variation of 1 mm caused, for example, by a connector not fully tightened, will cause a phase variation of approximately 17 degrees. Also, due to limitations on possible manufacturing tolerances, it may be impossible to build transmission line assemblies of several thousands of millimetres in length with less than 1 mm (or less than 0.1%) yield variation.

If the above assembly is connected to the measurement instrumentation (generator) and calibration is performed with the reference plane at the distal tip of the antenna, then the difficulties described above can be reduced or eliminated. Therefore, the invention addresses problems associated with inferring information regarding a remotely located tissue load connected to the distal tip of the antenna. Preferably, the cable assembly used between the generator and the distal tip of the antenna exhibits a low insertion loss and a small variation in phase with random flexure. It is preferable for the insertion loss of the complete assembly (flexible cable assembly and rigid co-axial antenna) to be less than 1.5 dB, and for the phase variation to be less than 2 degrees for any possible physical random variation of the flexible cable assembly.

The flexible cable assembly may be a co-axial cable assembly or a waveguide assembly or a combination of the two, for example, one metre of low loss waveguide assembly could be attached to the output of the electrosurgical unit and a second metre of flexible co-axial cable could be attached to the distal end of the waveguide assembly and be used as the flexible section to ease antenna manipulation. This arrangement could be particularly suitable where it is desirable to implement a structure where the treatment antenna is attached to a mechanical arm that forms a permanent structure. In this arrangement, a rotary joint may be employed to move the fixed arm in one plane. Said waveguide assembly may be flexible, twistable, or a combination of the two. The advantages of using a waveguide assembly are the high power handling capability and low insertion loss.

In one aspect, the invention may therefore relate to a calibration system to enable a surgical antenna arrangement to be calibrated at the distal tip. Such a calibrated antenna arrangement may be used to make repeatable measurements of the complex impedance of biological tissue for the purpose of the determination of the type of biological tissue and/or the state of said tissue, and/or for differentiating between healthy and cancerous tissue. Alternatively or additionally, the calibrated antenna arrangement may be dynamically impedance matched into a load represented by the changing state of said biological tissue during the treatment (or ablation) process to ensure that said energy is efficiently launched (or matched) into said biological tissue load, hence providing a controlled and efficient method of causing tissue ablation which can avoid the drawbacks associated with conventional ablation systems.

According to the invention, calibration takes place at the distal tip of the antenna, i.e. the reference plane where said calibration is to be made is positioned at the distal tip of the surgical antenna. During calibration, it is desirable for the distal tip of the antenna be exposed to a large range of impedances. Ideally the range should span from an open circuit, where the impedance is infinity, to a short circuit, where the impedance is zero, to make it possible for as much information as possible regarding the state of the biological tissue to be available for capture. The calibration system described in this invention may enable both the calibration plane to be located at the distal tip of the antenna and for the impedance measurement range to be maximised. It is required to be able to repeatably measure small changes in magnitude and/or phase in order to increase the chance of being able to differentiate between healthy and cancerous tissue or between types of cancerous tissue. It is therefore preferable to optimise the measurement sensitivity or capability. Described generally, this can be achieved using a sliding short circuit (or plunger) inserted inside a waveguide cavity that is of large enough geometry to prevent the wave from being cut-off. The exact location of the antenna and the overall physical geometry of the calibration system may be optimised based on the theory set out herein e.g. by using Computer Simulation Technology (CST) Microwave Studio® electromagnetic field simulation tool. However, the design of the calibration system is not limited to using this simulation package. Other suitable electromagnetic field simulation packages that may be used include Ansoft HFSS and Flomerics Microstripes.

In an alternative arrangement for performing a multipoint calibration, a plurality of fixed loads designed to fit to the distal tip of the surgical antenna that take into account the non 50Ω impedance environment created by the radiating tip (the aerial) could be used. However, this arrangement may require each load to be physically connected to the distal tip of the antenna. This may be particularly important in a surgical environment where possible operator error is preferably minimised and the time available to perform surgical procedures is limited. Other possible calibration arrangements include: a threaded arrangement whereby the load is moved by twisting a rod inside a cavity containing a moving load (short), or an arrangement whereby a load is moved using a biased, e.g. spring loaded, ratchet mechanism (e.g. similar to that used in retractable pens). In the latter arrangement, for example, the pressed state (where the spring is compressed) may cause the movable load to be in the short circuit position, and the released state (where the spring is released) may cause the movable load to be in the open circuit position, i.e. the movement between the pressed and released states may be an exact multiple of an odd number of quarter wavelengths at the frequency of operation to enable the impedance transformation from an open circuit to a short circuit or vice versa.

In another aspect, the invention may relate to a method of connecting a transmission assembly to a calibration system to perform an automated calibration using measurement instrumentation located away from the calibration site. In a preferred embodiment, the transmission assembly is 1.62 metres in length and comprises: a co-axial connector (preferably N-type), a flexible transmission cable of length 1.5 metres, and an antenna assembly of length 0.12 metres comprising itself of a section of rigid co-axial cable with an outer jacket made from a composition of stainless steel and copper or silver (the inner of the outer jacket shall be copper (or silver plated) to provide low conductor loss for the electromagnetic field), and a distal tip made from a low loss ceramic material that forms an impedance transformation circuit, and also provides the desired hardness and sharpness to enable the antenna to be directly inserted through human tissue. This invention is not limited to the use of co-axial transmission assemblies, or co-axial antenna structures. For example, the transmission line may comprise a waveguide assembly (solid, flexible or flexible/twistable) and a ceramic antenna structure may be coupled directly into said waveguide structure. The transmission assembly may be greater than 1.5 metres in length. The length may be limited by the insertion loss of the cable assembly and the antenna structure since the Q of the system is limited by the insertion loss and it is required for the Q to be as high as possible to enable a resonant cavity to be set-up between the tuner and the digital tip of the antenna. For conventional low loss co-axial cable the length may be limited to 3 metres.

In yet another aspect, the invention may relate to a method of operating the sliding short to enable the antenna to be connected to a plurality of calibration impedances. An example of calibrating to a specific impedance between the open and short load is as follows: if the sliding short is moved an electrical distance of three eighths of a wavelength at the frequency of operation from the short circuit (the generator) towards the tissue (the load) then, assuming that the transmission loss along said path is zero, the impedance will comprise an inductive reactance of value equal to the characteristic impedance of the transmission line. It should be noted that this analysis assumes that a perfect short circuit exists when the sliding short is at the distal tip of the antenna. The advantage of using the sliding load arrangement is that the variable load (or plunger) can be initially located inside the waveguide cavity to act as a short circuit and then automatically moved along the cavity using, for example, a linear actuator, and a plurality of measurement points will be taken during the movement of the sliding short. Assuming that the loss of the cavity is negligible, then the movement of the sliding short will produce a number of points around the circumference of the Smith chart and the centre of the circle, or the matched position, will be able to be accurately located.

In this aspect, a linear actuator may be attached to the generator and a sliding short, which forms a part of the calibration system, may be mechanically linked to the linear actuator, for example, using a mechanical arrangement whereby the sliding short is permanently connected to a rod which has a small groove (or recess) machined somewhere along its length, and the shaft of the actuator contains a hollow tube with a protruding section (maybe a ring) similar in size to said groove to enable the two mechanical devices to be linked together and separated with relative ease, but, at the same time, providing a good repeatable means of locating the rod inside the actuator. The calibration system may be physically connected to the generator by using two popper arrangements, i.e. similar to those used on jackets or coats, or alternatively by using pieces of hook and loop material (e.g. Velcro®) attached to the generator and to the calibration unit.

Other considerations include: using spring loaded ball bearings and locating holes in the waveguide cavity to locate the position of the sliding short, or a pen type arrangement, i.e. arrangements with a discrete number of calibration points.

There are a number of possible electromechanical actuators that may be considered for moving the sliding short inside the waveguide cavity. It may be preferable to use a linear actuator, for example, an LAL20 or an LAL35 linear actuator from SMAC (http://www.smac-mca.co.uk/LAL.htm), but other electromechanical actuators that may be used include: a stepper motor, a moving coil actuator, a magnetostrictive linear actuator or a piezo-electric based device.

This aspect of the current invention may also take into account that the antenna and calibration system are single use items, and it is necessary for them to be contained in a sterile container or housing, hence the movement of the sliding short is preferably in one direction only and this direction is such that the sliding short moves out of the waveguide cavity, thus when the mechanical linkage between the sliding short and the linear actuator is first made, the sliding short should preferably be in the 'short circuit' position. One of the possible advantages of the automated calibration system described here is the simplicity of use; for example, it should be possible for an operator (e.g. technician or surgeon) to connect the proximal end of the cable assembly to the RF output port of the generator, and connect the sliding short of the calibration system to the generator (or electronic instrumentation unit), then press a 'calibration' button once to enable a fully automated system calibration to be performed. This aspect makes the electrosurgical system user friendly and more attractive for surgical use than a system that, for example, requires a plurality of fixed impedance loads to be manually connected to the distal tip of the antenna, since, in this instance, the operator is required to make a number of physical connections and may be required to repeat a specified calibration sequence for each load; this process can be time consuming, requires specific operator training, and is prone to human error.

The cable assembly, surgical antenna and the calibration unit may form a single use disposable item. These components may therefore be contained in a sterile package with only a small section of the cable assembly (which may be attachable to a customised microwave connector), and the sliding short (or plunger) accessible for connections to be made to the electronic instrumentation (generator). These parts will not be in contact with the patient and therefore are not required to be sterile. Consideration is, therefore, given to materials used for the calibration system housing and the moveable plunger. If these units are to be disposable, it may be preferable to develop a mould (or tool) to produce the units from a plastic material and then metallise the surfaces with a layer of high conductivity material, for example, silver or gold, to a thickness that allows the microwave signals to propagate unimpaired, for example, a thickness of five skin depths will allow 99% of the energy to propagate. Silver may be most preferred as it is an acceptable material for use in a medical environment, i.e. if small deposits of silver were to be left behind on the probe tip subsequent to calibration then this would not present a patient hazard.

Alternatively, the calibration unit may be non-disposable. In this case, the surgical antenna may be packaged in such a manner that it can be inserted inside the calibration unit and calibrated whilst remaining in a sterile environment. For example, the antennas may be packaged inside a sterile bag or packet that fits tightly to the body of the antenna and the wall thickness of the material is such that that it does not affect the performance of the distal tip of the antenna (the aerial), i.e. the material is transparent to the microwave signals. In this arrangement, the calibration system may be located inside the generator with the electronic instrumentation, and the antenna may be inserted into a slot or inlet on the front of the generator to enable calibration to be performed. The antenna holder may have a dust cap or cover that is attached to the calibration inlet to protect it from duct or ingress.

It is desirable to calibrate invasive surgical probes comprising coaxial monopole structures having radome aerials with sharp pointed ends because of their ability to penetrate soft material with minimal constraints on shape and configuration. Such probe structures can create measurement ambiguities which may add uncertainty to results obtained from standard one-port calibration equipment, e.g. an SMA calibration kit.

The encountered ambiguities can be separated into two categories: random errors and systematic errors. Random errors are non-repeatable measurement variations due to physical changes in the test set-up. Possible sources include connector repeatability, e.g. test port cables and instrument noise. These errors are usually unpredictable and cannot be removed by calibration. However, these can be minimised by taking measurements several times and taking the average value. Systematic errors may therefore be the most significant source of measurement uncertainty. The open-ended structure and non-standard shape of some surgical probes which make them desirable for use in the system may make it difficult to consistently and repeatably produce a good matched termination using standard calibration equipment. In other words, surgical probes within a batch of probes do not have a uniform impedance and their shape does not allow standard SMA calibration loads to be connected. Performing a calibration using normal calibration standards will therefore result in significant errors in the measured complex impedance, which leads to unreliable tissue type recognition.

A slidable short circuit movable inside a waveguide cavity discussed above goes some way to ameliorating this difficulty. Its effect is to mimic a vector network analysis calibration procedure, in which a series of known devices (standards) are connected to the device under test (DUT) and the response to those standards recorded. In the arrangement described above, the surgical probe is receivable in the cavity whereby a plurality of impedances having known values based on the (known) wavelength of the emitted microwave radiation can be presented by positioning the short circuit at suitable locations along the cavity. The sliding short circuit enabled the reactance of the cavity to be varied. The locations of the sliding short circuit are selectable based on the wavelength of the emitted radiation to present a plurality of known calibration standards (impedance values) to the probe. Signals reflected from the calibration standards are recorded to determine a reference point (e.g. a perfectly matched point) with which to compare subsequent measurements.

This method is particularly effective when the complex impedance of probes to be calibrated is such that their impedance values are in the same region of the Smith chart. If the complex impedance of the probe tip varies then the circle formed by the plunger moving out of the cavity (the complete Smith chart will be traversed in a plunger movement equal to a half of the wavelength at the frequency of interest—at an operating frequency of 14.5 GHz, this is about 10 mm) will vary in terms of diameter and the centre point. For example, if the impedance caused by the probe being inserted inside the cavity of the calibration jig is 50+j0Ω then the diameter will be zero and the centre will be 50Ω. It is possible to move the centre point presented by the probe to as more suitable region by use of an additional stub (or a plurality of stubs within the waveguide cavity—three stubs can permit the point to be moved anywhere on the Smith chart, assuming a lossless system). However, adjusting the additional stub(s) to move the impedance to a more appropriate point is only practical if a single adjustment suffices for all probes. If the probes exhibit a wide variety of impedance magnitudes, an adjustment may be required for each probe. This may not be practical.

Thus, in a development of the first aspect, there is disclosed a calibration technique capable of accurately calibrating a batch of probes whose complex impedances may be in any region of the Smith chart. At its most general, the development of the first aspect can be expressed as a one port error correction technique which provides a plurality of calibration standards which have a range of complex impedances at a predetermined frequency and which can conform to surround an emitting region of a probe. For example, the calibration standards may be fluid (e.g. liquid) or fluid-like (granular or particulate) solid (e.g. dust or sand). Each probe can be calibrated by immersing the antenna on the probe which emits a microwave radiation field at the predetermined frequency into the calibration standards. This may mimic the insertion of the probe into tissue. Calibration is performed by detecting the magnitude and phase of radiation reflected from the interface between probe and calibration standard.

Thus, according to the first aspect of the invention there may be provided a method of calibrating a surgical probe having an antenna arranged to emit a microwave radiation field at a predetermined frequency, the method comprising: sequentially presenting the probe to each of three or more calibration standards which have a range of complex impedances at the predetermined frequency; detecting the magnitude and phase of microwave radiation reflected from the probe when presented to each calibration standard to determine a measured impedance value for each calibration standard; and comparing the measured impedance values with reference impedance values for each standard to determine a mapping function for transforming subsequent measured impedance values, wherein each calibration standard is arranged to conform to the shape of the probe to surround the antenna.

Each calibration standard may be a fluid (preferably liquid) or fluid-like (e.g. flowable) solid (preferably powdered material such as sand or dust). Alternatively, the calibration standard may be a conformable or malleable solid e.g. adapted to wrap around the antenna of the probe. Presenting the probe to each calibration standard may include immersing the antenna in each liquid.

The calibration standards may be formed by mixing two or more materials having differing impedances in differing proportions. The two or more materials may all be liquid to facilitate mixing. By selecting appropriate materials, a range of consistent calibration standards (i.e. mixtures having repeatably obtainable complex impedances) whose complex impedances are spread across the Smith chart can be obtained. The range of complex impedances of the calibration standards at the predetermined frequency may include real components spread between 0.5 and 2.0.

The predetermined frequency may be a single stable frequency. For calibration to be accurate, the predetermined frequency is preferably the frequency of operation of the device, e.g. 500 MHz or more, preferably 10 GHz or more, e.g. 14.5 GHz, 24 GHz or the like.

The proposed calibration standards (sometimes termed reference liquids herein) may enable the mismatch between each probe in a batch of probes to be compensated. In one embodiment, the reference impedance values for each calibration standard are measurements taken using a reference probe. In this case, calibration measurements taken for a given probe (e.g. the detected impedance of the calibration standards through the probe) may be mapped on to the measurements taken for the reference probe. The mapping function may then be used on measurements taken from unknown samples. The mapped measurements can be used to identify tissue, e.g. by comparing them with stored values for known tissue types obtained using the reference probe. The comparison may use a look up table or the like.

Thus, the calibration technique proposed herein may permit determination of the mapping function to enable measurements taken by the calibrated probe to be accurately compared with known values stored for the reference probe.

Alternatively, the calibration may be absolute, i.e. the impedance values of the calibration standards may be known. In this case, the mapping function may act to map measured impedances to actual impedances. Actual impedance values for various tissue types (which may be known from reference books or predetermined by experiment) may be stored in a look up table for comparison, i.e. to enable the tissue type at the probe tip to be identified.

The calibration technique disclosed herein may reduce uncertainties in the impedance measurements made using open-ended coaxial monopole antennas which terminate in radome aerials.

The calibration standards may be formed from varying proportions of two or more miscible liquids which have differing impedances for microwave radiation at the predetermined frequency. For the most accurate and repeatable results, it may be desirable to use only two liquids, and for these liquids to have a consistent content, e.g. be free from impurities or have a fixed proportion of ingredients. For example, the two liquids may be pure (and anhydrous) ethanol and de-ionised water. To aid repeatability, it is desirable for the water and ethanol in each calibration standard to be obtained from the same source. The calibration standards may be mixtures comprising varying proportions of the two liquids, e.g. 100% water, 50% water/50% ethanol, and 100% ethanol.

Pure liquids need not be essential however. In one embodiment, different proportions of water and methylated spirit where used to form the calibration standards. These two materials have the advantage of being readily miscible and biocompatible. Methylated spirit or denatured alcohol is effectively a mixture of ethanol (~90%) and methanol (~10%). To aid repeatability it is desirable for the content of the methylated spirit (i.e. relative proportion of ethanol and methanol) to remain constant.

Measurement/Ablation System Configuration

According to the second aspect of the invention, there may be provided tissue measurement and ablation apparatus having: a source of first microwave radiation having a first predetermined frequency and second microwave radiation having a second predetermined frequency, a probe for directing microwave radiation from the source into tissue, the probe having an antenna adapted to emit the microwave radiation from an emitting region thereof; a first channel for carrying microwave radiation between the source and the probe in a controlled ablation mode; a second channel for carrying microwave radiation between the source and the probe in a measurement mode; a switch for selecting a channel according to the required mode of operation; and a detector for detecting the magnitude and phase of microwave radiation reflected from the tissue; wherein the first channel is operable at a first power level and includes a tuner arranged to dynamically match the impedance of the apparatus with the impedance of the tissue seen by the emitting region of the antenna, and one or more power couplers arranged to couple the reflected microwave radiation to the detector; and wherein the second channel is operable at a second power level and is arranged to directly supply the reflected microwave radiation to the detector. Preferably, the second power signal is supplied via a circulator with high isolation and a carrier cancellation circuit.

Preferably, the first power level is two or more orders of magnitude larger that the second power level.

The second channel may include a transceiver for transmitting a low power signal in a forward direction from the source to the probe and receiving and directing the reflected microwave radiation to the detector. Noise sources in the transceiver circuitry, i.e. components that generate random (thermal or short) noise, can limit the measurement sensitivity of the system. Thus in the second aspect, a new low power transceiver design is disclosed. This can be important since the sensitivity of the overall measurement system is determined by the transceiver topology, along with the choice of cable assembly, the surgical antenna design, and the method of antenna calibration.

The enhanced system described here may use two separate channels (or modes of operation) and one co-axial cable assembly and surgical antenna to deliver the modes of operation. The two channels (or modes of operation) are the treatment channel, which includes dynamic impedance matching between the energy source and the distal tip of the surgical antenna, and the dielectric measurement channel, which uses a low power microwave signal to transmit energy into the biological tissue and may include a circulator, with a carrier cancellation circuit, to provide a path for the reflected signal to travel back to the receiver to enable tissue type/state (dielectric) measurement to be performed. It is preferable for the circulator used to separate the transmitted and received paths to exhibit a high level of signal isolation between the transmit and receive ports (normally ports 1 and 3 for conventional circulator configurations). Full analysis of the operation of the treatment channel has been performed and it has been found that a resonant cavity is set up between the triple stub tuner (the tuning filter) and the distal tip of the surgical antenna (the aerial) and the operation of this cavity is similar to that of a Fabrey-Perot cavity. The effectiveness of this cavity is determined by the insertion loss of the cable assembly connected between the output of the triple stub tuning network and the proximal end of the surgical antenna, and the insertion loss of the surgical antenna itself. A full analysis of the operation of this tuning system is provided in Appendix A at the end of this description. The analysis given considers changing the impedance of the tuner to match the conditions experienced at the distal tip of the antenna, such that the maximum power (or the demanded power) is transmitted out of the end of the antenna and into the surrounding tissue load. This process involves microwave power reflecting in both directions between the distal tip of the antenna and the triple stub tuner. For matched conditions, a standing wave may be set up in the cable, where the field is higher than the incident field from the generator and the field transmitted into the tissue load. The magnitude of this field will be determined by the power of the incident wave, the insertion loss of the transmission line, and the degree of mismatch at the distal end of the antenna. A large mismatch at the distal tip of the antenna will require a correspondingly high mismatch to be set up at the triple stub tuner and this will lead to a large number of multiple reflections and a large standing wave. The magnitude of this standing wave will be determined by the Q of the cavity, which is a function of the insertion loss of the cable assembly between the triple stub tuner and the antenna, which itself is a function of the length of the cable. This device uses a resonant cavity to enable a generator (source) to deliver a demanded energy (or power) into a tissue load when the load is not matched to the source impedance, i.e. a high mismatch or reflection coefficient exists at the distal tip of the surgical antenna. In one embodiment, the antenna may be arranged to match the initial impedance of the tissue. As the tissue is treated its impedance will change, which will change the impedance match and cause reflections. For example, water content may be removed from the tissue, which will cause the impedance to change.

The system may be used to probe materials to determine various types of information or properties/characteristics relating to the materials, or be used to provide a complex conjugate match between an energy source and a load to enable maximum energy transfer from a fixed impedance source into a variable impedance load. In the latter case, a control system may be used to measure the complex impedance seen at the distal tip of the surgical antenna (at the point where it is in contact with the load) and automatically make adjustments to an impedance matching network connected between the generator and the load to enable maximum power transfer between the generator and the load. This arrangement will minimise reflections due to impedance mismatches between the generator and the load. The output impedance of the matching network may be adjusted to be the complex conjugate of the load in order to achieve matching. The ability to make an effective measurement of the complex impedance needed to create a complex conjugate condition at the output of the matching filter can depend upon the ability to calibrate the surgical antenna at the measurement plane, i.e. at the position where the surgical antenna is in contact with the load. The ability to calibrate at this point means that the microwave measurement system up to this point is effectively transparent, i.e. the distal tip of the antenna is effectively connected to the position in the system where the digital signal processing is performed, e.g. the input to a digital signal processing unit.

Antenna Structure

According to the third aspect, there may be provided a surgical antenna for insertion into tissue, the antenna comprising: an elongate body with a feed structure comprising: an inner conductor along the length of the elongate body, and an outer conductor surrounding the inner conductor and separated therefrom by a dielectric material, a connector for connecting the conductors to a microwave power source to receive microwave frequency energy therefrom, and an insertion tip at a distal end of the elongate body for penetrating the tissue, wherein the insertion tip comprises a radiating structure connected to the conductors for emitting the microwave frequency energy out of the antenna to treat the tissue, and an impedance transformer for matching the impedance of the dielectric material with the treated tissue.

Preferably, the insertion tip comprises a ceramic cone tip to which the radiating structure is attached. The ceramic cone tip may be the impedance transformer. In one embodiment, the radiating structure may comprise metal spirals that are fabricated onto the surface of the ceramic cone. Alternatively, the radiating structure may comprise a plurality of co-axial monopoles or dipoles which protrude through the ceramic cone and an impedance transformer to match the parallel impedance of the monopoles or dipoles with the feed structure.

The surgical antenna structures of the third aspect may be particularly suitable for use with the calibration system described herein. Examples include: a measurement/ablation antenna for treating breast tumours, a conical or spiral tip antenna consisting of a cone made from a microwave ceramic material with metal spirals fabricated onto the surface of the cone (the cone may also form an impedance transformer to provide impedance matching between the dielectric used in a co-axial feed structure and the treatment tissue), a turnstile antenna arrangement where two dipoles are energised with currents of equal magnitude but in phase quadrature, a loaded waveguide antenna where the ceramic loading material also forms the radiating antenna (the aerial), for example, a ceramic blade antenna with a portion of the blade metallised, a monopole (or needle antenna) with balun, a monopole with an inverted balun, a monopole with a ceramic tip with an inverted balun, a monopole with a ceramic tip without a balun, and an arrangement using a plurality of co-axial monopoles/dipoles protruding through a ceramic cone with an impedance transformer to match the parallel impedance of the monopoles/dipoles with the co-axial feed structure. Specific embodiments are given in this document for the co-axial antenna with four monopole radiators, the co-axial antenna for liver treatment, the spiral antenna, the antenna using the inverted balun arrangement, and the sapphire blade loaded waveguide antenna.

The above surgical antennas may be used for treating and/or measuring information relating to solid tumours, soft tissue, and may also be used in other surgical procedures. For example, treatment and location of breast tumours, treatment and location of prostate cancer, treatment of brain tumours, treatment of liver tumours, and for use in liver resection, treatment and location of ulcers, and treatment and measurement of lung cancer.

The surgical antennas presented in this description have been developed for use in treating solid tumours, where it will be necessary to be able to dynamically match microwave energy into a variable tissue load, and/or for use in identifying various tissue types or states, for example, differentiating between healthy and cancerous tissue or for determining when the distal tip of the antenna is in contact with cancerous tissue. It is desirable for these antenna structures to be calibrated at the distal tip (the aerial).

BRIEF DESCRIPTION OF THE DRAWINGS

A detailed description of the above aspects of the invention is given below with reference to the accompanying drawings, in which.

DETAILED DESCRIPTION; FURTHER OPTIONS AND PREFERENCES

Calibration System and Procedure

Figure 1:
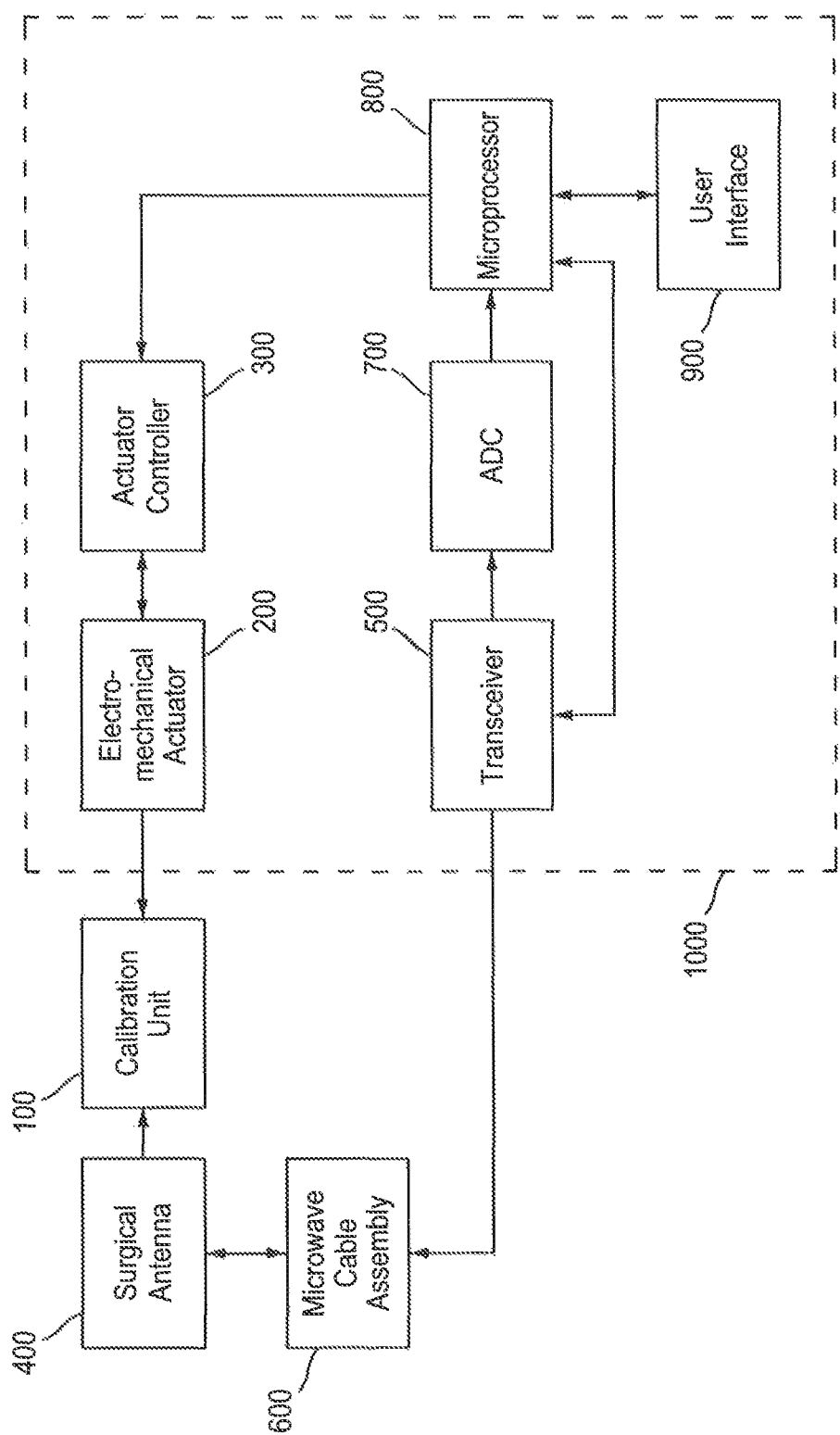
FIG. 1 shows a block diagram of an antenna calibration system that is an embodiment of the present invention.
Figure 7:
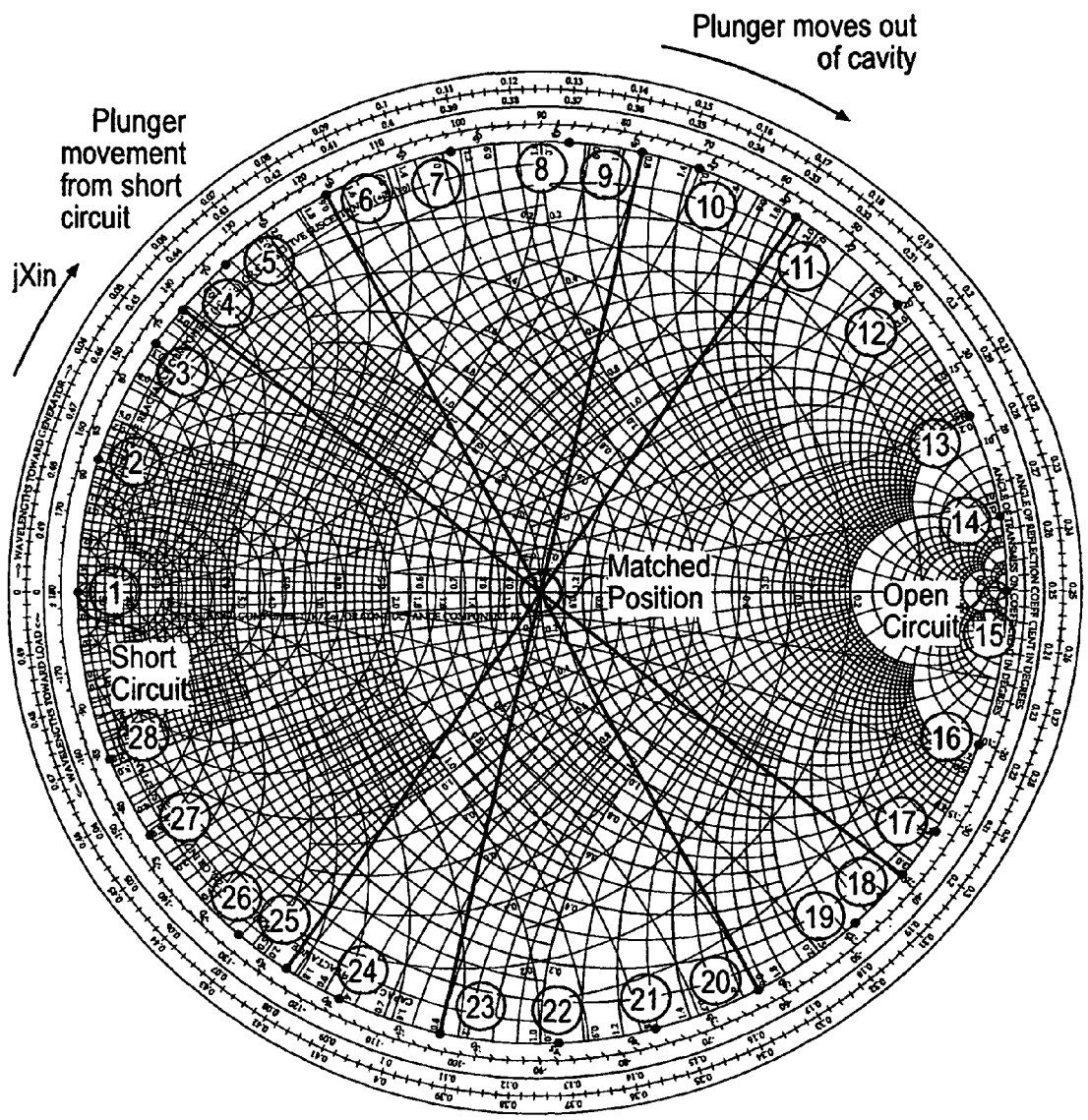
FIG. 7 shows a Smith chart with calibration measurement points plotted thereon.

FIG. 1 shows a block diagram of the automated multi-point surgical antenna calibration system. It is preferable for the electronic instrumentation 1000 to be housed inside an enclosure and this enclosure may be referred to as the generator. The calibration unit 100 is a mechanical assembly comprising a mechanism to enable a multipoint calibration to be performed. The surgical antenna 400 is coupled to the calibration unit 100 in such a manner, as to allow the distal tip of the antenna (the aerial) to be subjected to a plurality of impedance values set up by adjustment of a mechanical sliding mechanism in calibration unit 100. The mechanical sliding mechanism may be known as a sliding load or a sliding short circuit, and adjustment of this mechanism is performed using an electromechanical actuator 200, whose function is to move the sliding mechanism e.g. in and out of the calibration unit assembly. The electromechanical actuator is controlled using an actuator controller 300, which may be a proportional-integral-differential (PID) controller. Such a controller ensures that the movement of the actuator can be controlled precisely. The control signals for actuator controller 300 come from a digital signal processor/microprocessor unit 800, and these signals are based on instructions provided e.g. by a user via the user interface 900. The impedance seen at the distal tip of surgical antenna 400, due to the position of the sliding load contained within calibration unit 100, is then measured by digital signal processor/microprocessor unit 800. In order for the measurement of the calibration impedance to be performed, a microwave signal is sent to surgical antenna 400 via microwave cable assembly 600. The microwave signal is generated using the transmitter section of microwave transceiver 500. The transmitted signal from transceiver 500 is sent along microwave cable assembly 600 to surgical antenna 400 and the position of the sliding load within calibration unit 100 causes the distal tip of surgical antenna 400 (the aerial) to be subjected to a mismatch (producing a reflection coefficient of between 0 and 1). The reflected signal due to this mismatch is sent or transported from the distal tip of surgical antenna 400, along the shaft of the antenna, back along microwave cable assembly 600 to the receiver section of transceiver 500. The receiver down converts the frequency of the signal to a frequency that can be used by analogue-to-digital-converter (ADC) 700, whilst preserving the phase information contained within the signal to enable digital signal processor/microprocessor unit 800 to extract phase and magnitude information from the signal. This information is used to determine a calibration point. Therefore, each position of the sliding load (governed by the voltage signal applied to the electromechanical actuator 200 provided by PID controller 300 via digital signal processor/microprocessor unit 800) provides a single calibration point. The phase and magnitude information may be converted into complex impedance using digital signal processor/microprocessor unit 800 and each value of complex impedance corresponding to a position of the sliding load may be plotted on an impedance chart known as a Smith chart. This information provides the information necessary to calibrate the system with a reference plane (or measurement point) placed at the distal tip of surgical antenna 400. FIG. 7 shows a Smith chart showing 28 calibration points. This plot shows all of the measured points located on the outer circumference of the Smith chart, thus this arrangement assumes that the waveguide cavity contained within calibration unit 100 is lossless. In practice, there may be some losses associated with the waveguide cavity and also cable assembly 600 and surgical antenna 400. This loss will bring the calibration circle closer to the centre of the Smith chart, i.e. the radius of the calibration circle will be reduced.

The Smith chart provides a convenient means of representing any impedance value. In practice, the system measures phase and magnitude information for each of the positions of the sliding short within the cavity and this information may be plotted, stored or converted into any format. It may be convenient to store phase and magnitude (two numbers) for each position of the sliding short into a look-up table or into memory (RAM or DRAM) and once all points have been measured, a mathematical computation can be made to establish a reference point for subsequent tissue state measurements. For example, the reference point may be 0, 1 or −1. It is advantageous to measure enough calibration points to enable phase changes of between 0° and 360° to be measured and for measurable magnitudes to span the range of between −1 and 1. The reference position is determined by calibration prior to taking tissue state measurements. The reference position is also determined by calibration when a new cable-antenna assembly is connected to the generator.

It may be desirable to measure over a wide range, i.e. to capture a phase change of up to 360°, since the phase change for various tissue types can be large.

In use, real tissue state measurements are compared with the reference point to establish the impedance seen at the distal tip of the antenna.

Figure 2:
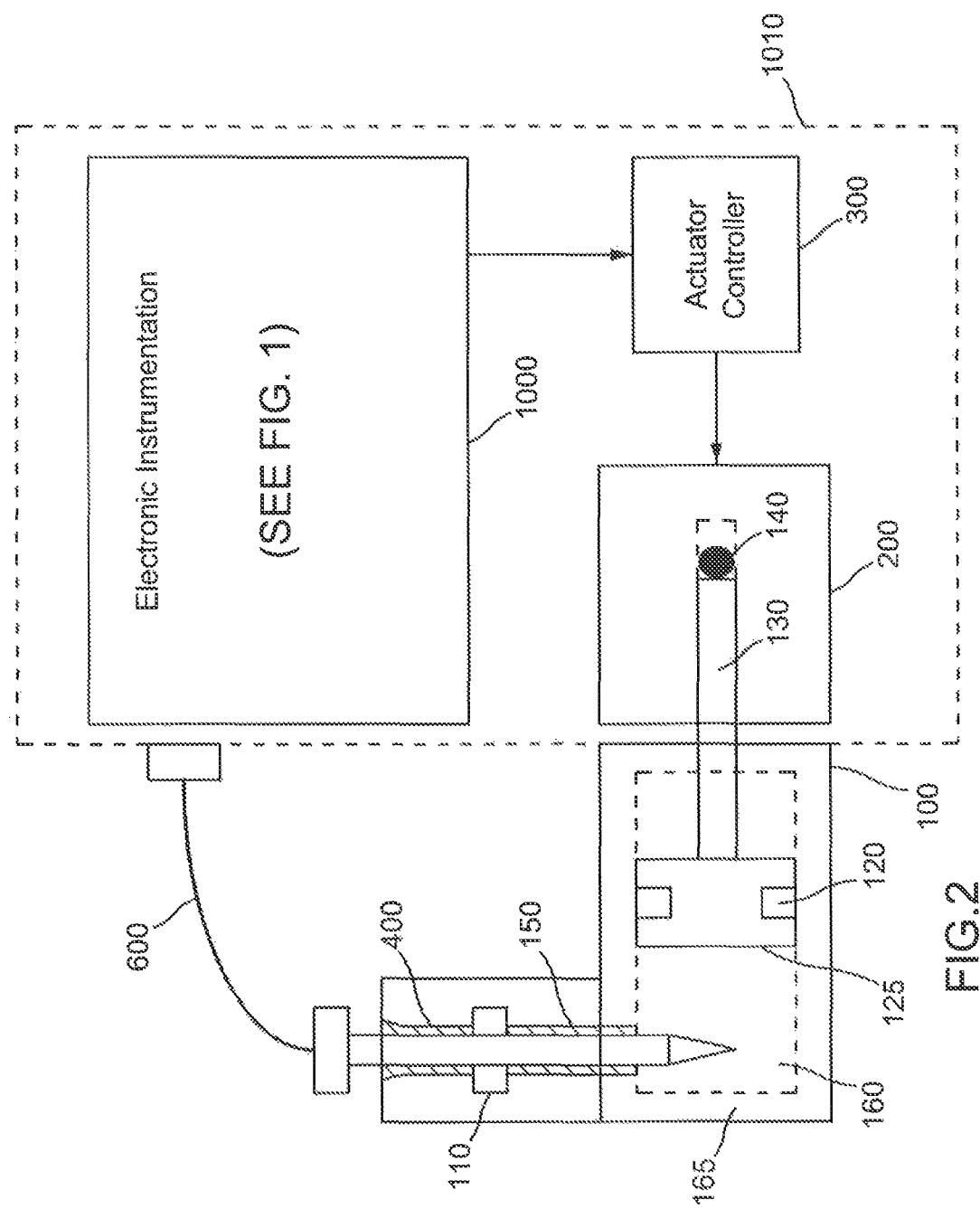
FIG. 2 shows an automatic calibration system with a calibration unit separate from a generator.

FIG. 2 shows an embodiment of an automatic calibration device connected to the rest of the system. The calibration unit 100 is connected externally to generator 1010 using a suitable and secure attaching arrangement 180. This attachment device may be a strip of Velcro®, a popper/stud arrangement, or any other suitable mechanical linkage. In this configuration, calibration unit 100, surgical antenna 400, and cable assembly 600 form a single use disposable item. The surgical antenna 400 may be sterilised and assembled into calibration unit 100 during manufacture. Indeed, calibration unit 100 and a section of cable assembly 600 may be housed in a sterile package (not shown). During the calibration process, the calibration unit 100 and plunger 130 are attached to the generator 1010 and the proximal end of the cable assembly 600 is connected to the transceiver contained within electronic instrumentation 1000 (see FIG. 1) contained within generator 1010. A mechanical linkage 140 is used to connect plunger 130 to linear actuator 200. Actuator controller 300 is controlled using electronic instrumentation 1000.

Calibration unit 100 contains two RF chokes; the first choke 110 is used to ensure that antenna 400 is electrically connected to walls 165 of calibration unit 100 via insertion tube 150 without the need for an interference fit between the wall of the insertion tube 150 and the outer jacket of surgical antenna 400. It is preferable to use choke 110 rather than designing the components to have an interference fit as it is desirable to coat surgical antenna 400 with a layer of biocompatible material, for example, Parylene C, and this coating may get scraped off if the outer jacket of antenna 400 is in close contact with the wall of insertion tube 150. The second choke 120 is used to enable the plunger to slide along the waveguide cavity 160 freely whilst providing a good electrical short circuit between the sliding load (or sliding short) 125 and the inner wall of waveguide cavity 160.

Figure 3:
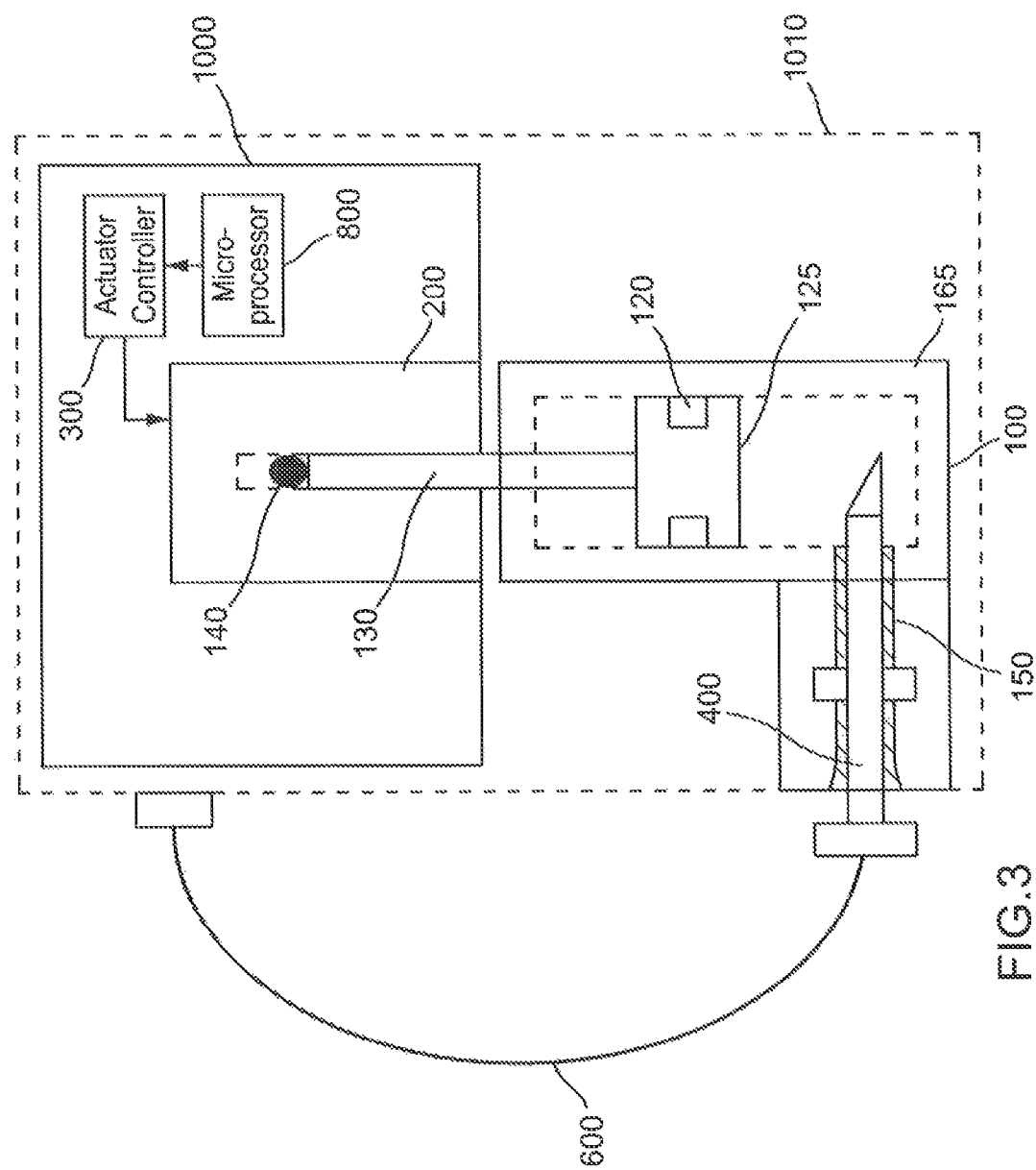
FIG. 3 shows an automatic calibration system with a calibration unit inside a generator.

FIG. 3 shows a configuration for the automatic calibration system where calibration unit 100 is contained within generator 1010. Features in common with FIG. 2 are given identical reference numbers. In this arrangement the disposable items are surgical antenna 400 and cable assembly 600 only. Due to the fact that calibration unit 100 will be used to calibrate many surgical antennas, it may not be possible for the wall of insertion tube 150 to provide a sterile environment for surgical antenna 400, therefore, it may be necessary for surgical antenna 400 to be packaged inside a sterile bag or a housing that can be peeled off subsequent to calibration, hence providing a sterile environment for surgical antenna 400.

Figure 4:
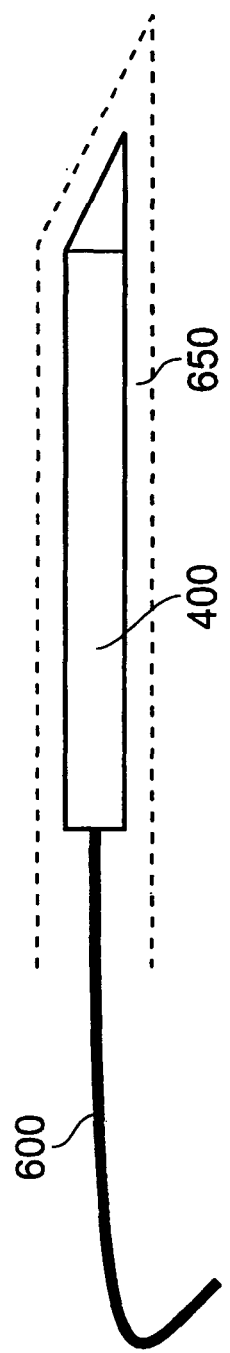
FIG. 4 shows a surgical antenna with a sterile cover.

FIG. 4 shows a sterile cover (bag or housing) 650 that can completely enclose surgical antenna 400 and a section of the attached cable assembly 600. To enable surgical antenna 400 to be effectively calibrated using the arrangement shown in FIG. 3, the wall of the sterile housing 650 is as thin as possible and made from a material that does not adversely affect the electrical properties of the distal tip (the radiating aerial) of surgical antenna 400, i.e. it is desirable for the sterile housing 650 to be electrically transparent to the impedance produced by the sliding load at the microwave frequency used to perform the calibration procedure. The thickness of the sterile housing 650 should also be limited to ensure that surgical antenna 400 will fit down insertion tube 150 without being ruptured or damaged. First RF choke 110 helps ensure that the outer wall of surgical antenna 400 is electrically shorted to the wall of insertion tube 150 and that RF leakage is minimised. The effectiveness of RF choke 110 can be enhanced by keeping the thickness of sterile housing 650 as thin as possible and by using a material for sterile housing 650 that is low loss at the calibration frequency of choice. In the arrangement shown in FIG. 3 the plunger 130 is permanently connected to linear actuator 200 using mechanical linkage 140. For example, sterile housing 650 preferably has a thickness less than 0.2 mm, and more preferably less than 0.05 mm, the material preferably has a loss factor or dissipation factor (tan $\delta$) of less than 0.0009, and more preferably less than 0.0002 at the frequency of interest.

The actuator 200 used to move the plunger in and out of the waveguide cavity contained within calibration unit 100 may take the form of a linear motor, a moving coil actuator, a piezoelectric device, a stepper motor or magnetostrictive material based actuator. For the system developed here, it was preferable for electromechanical actuator 200 to be a high resolution linear actuator with a long enough stroke to enable complete movement around the circumference of the Smith chart. A linear actuator with the part number LAL35-025-71F made by SMAC Europe Ltd is suitable.

The calibration that can be performed using the above embodiments is a one port (single port) calibration. It is desirable to calibrate over as large a range of loads as possible. The measurements performed using the treatment (dynamic matching) and measurement system (tissue state/type recognition) will contain measurement errors and these errors can be broken up into two groups: systematic errors and random errors. Random errors are non-repeatable measurement variations due to noise (for example, short noise or thermal noise generated by components within the system), temperature variations, and other non deterministic physical changes in the system. Systematic errors include leakage and mismatch signals in the microwave circuit (instrumentation) line-up, isolation characteristics between reference and test signal paths, (for example, the circulator used in the transceiver circuit 500), and system frequency response. In normal microwave measurement systems, systematic errors are the most significant sources of measurement uncertainty. In a stable measurement environment, systematic errors are repeatable and corrected for by calibration. During measurement calibration, a series of known devices (or standards) are connected to the measurement device (the radiating aerial of the surgical antenna in this instance). The systematic effects are determined as the difference between the measured and the known response of the standards. Once characterised, these errors can be mathematically related.

Figure 5:
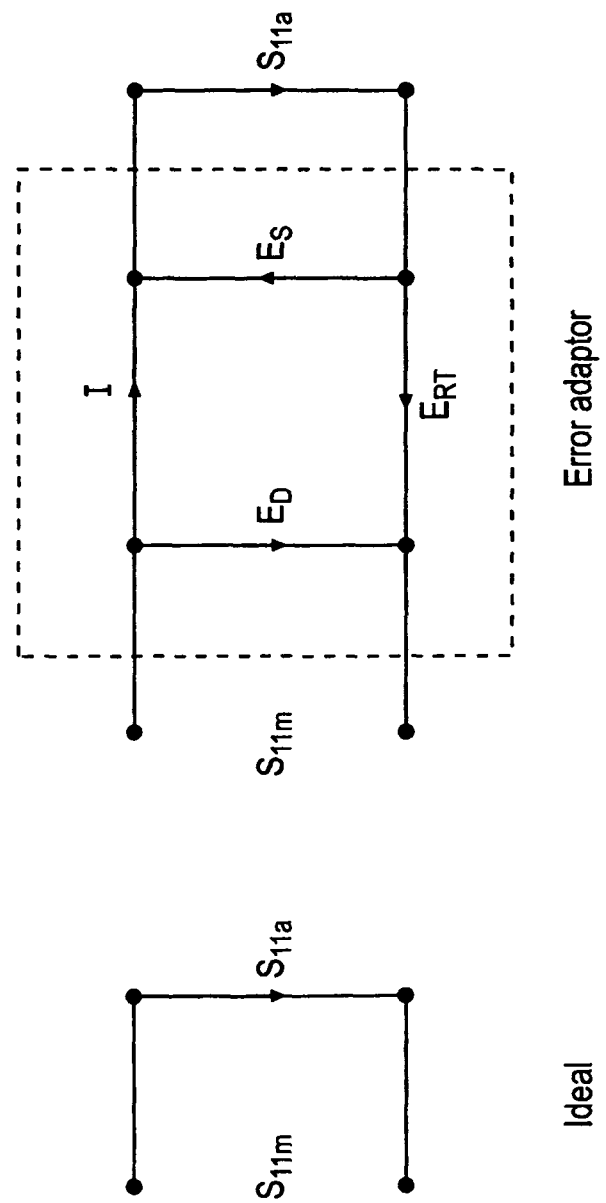
FIG. 5 shows a model for a one point calibration arrangement.

The calibration technique disclosed above is a one port calibration. The system disclosed herein is also a one port system. The measurement that is performed is a reflection measurement, where a signal is sent from a low power microwave source through an antenna to a load and the signal that is reflected back from the load is measured. In other words, a single port transmits a signal, and meanwhile receives the signal reflected from the biological tissue load. This measurement is often referred to as a scattering parameter measurement, and the particular measurement performed here is the forward reflection measurement, known as an $S_{11}$ measurement. The dynamic range of reflection measurements is limited by the directivity of the measurement port. To improve the measurement accuracy and sensitivity, it is desirable to conduct a one-port calibration because this can measure and remove three systematic error terms present in one port measurements: directivity, source match, and reflection tracking. FIG. 5 shows the equivalent circuits of an ideal case and an error adaptor. The relationship between the actual scattering parameter $S_{11a}$ and the measurement result $S_{11m}$ is given by equation 1:

$$S_{11m} = E_D + \left(\frac{E_{RT} \times S_{11a}}{1 + (E_s \times S_{11a})}\right), \qquad 1$$

where $S_{11m}$ is the measured $S_{11}$ value, $S_{11a}$ is the actual $S_{11}$ value, $E_D$ is an error from the directivity of the measurement system, $E_{RT}$ is an error from reflection tracking, and $E_s$ is an error from mismatch at the source.

In order to get the three systematic error terms so that the actual reflection measurement can be derived from the measurements taken, it is necessary to create three equations and three unknowns and solve them simultaneously. In order to achieve this, three calibration standards are required, for example, a short circuit, an open circuit and a known load impedance. If, for example, only one calibration standard was used, which, for example, may be air or a short circuit, then measurement accuracy and sensitivity would be limited. In the preferred embodiment given for the automated calibration system developed in this work, a plurality of calibration points are measured to give the desired level of sensitivity.

Figure 6A:
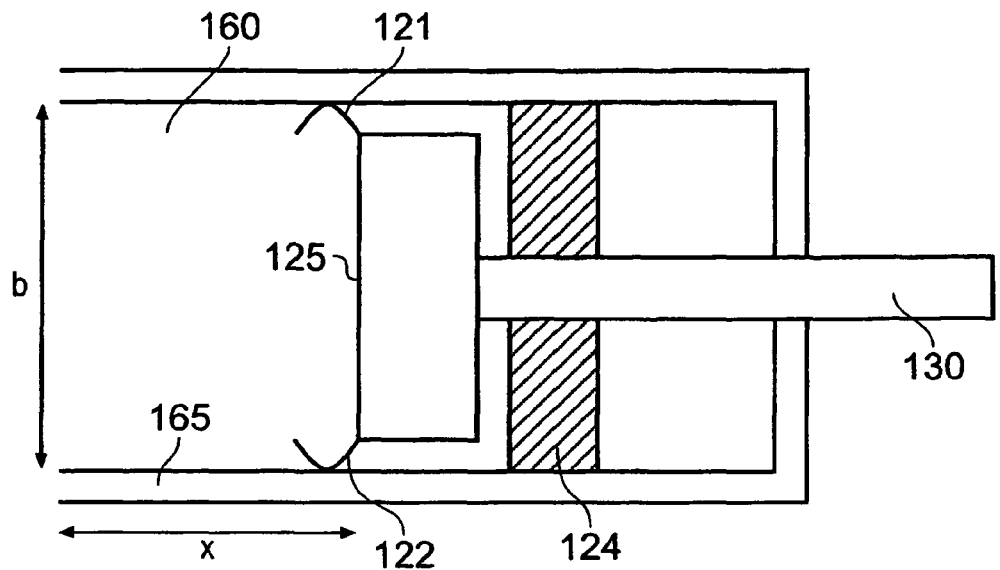
FIG. 6 shows adjustable sliding short circuits for an automated calibration system that is an embodiment of the invention.
Figure 6B:
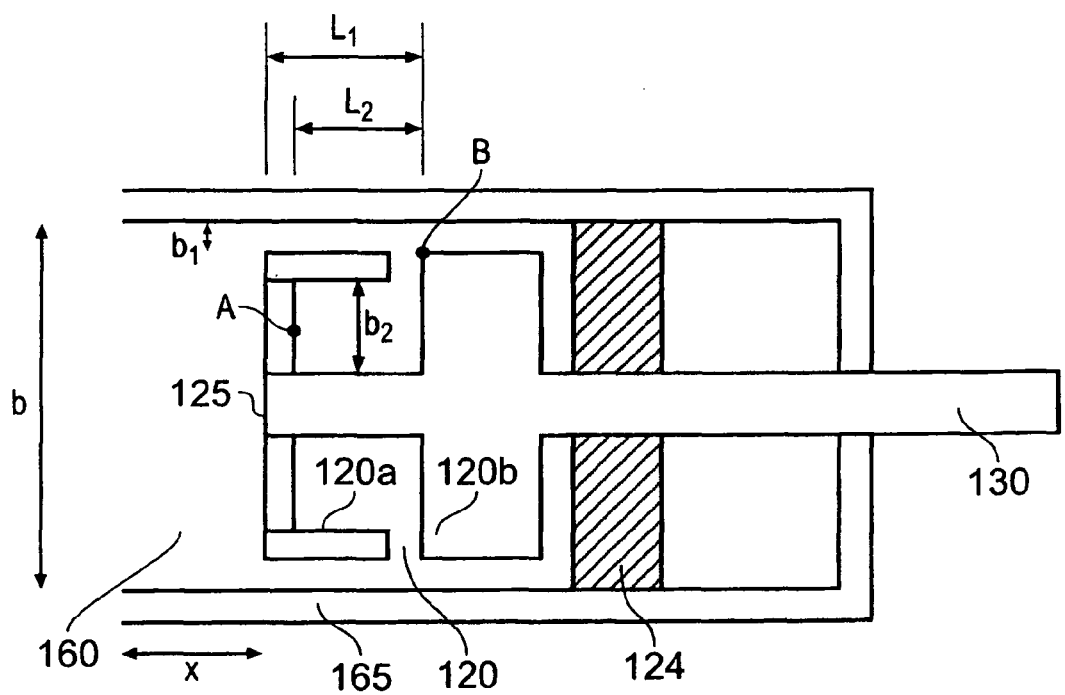

Two methods of producing an adjustable short circuit, or a sliding short circuit (or a sliding load) to provide a variable reactance within a waveguide system are shown in FIGS. 6(a) and 6(b) respectively, where the normalised waveguide input impedance $Z_{in}$ is given by equation 2 below:

$$\frac{Z_{in}}{Z_0} = Z_{in} = jX_{in} = j\tan\left(\frac{2\pi x}{\lambda_g}\right) \qquad 2$$

where x is the short position (in metres), $Z_0$ is the waveguide impedance (in ohms), $X_{in}$ is the reactance (in ohms), and $\lambda_g$ is the guide wavelength (in metres).

Any value of $X_{in}$ can be realised by proper adjustment of the short position x within the waveguide cavity 160. For example, if x=$\lambda_g$/4 then the reactance will be infinite (an open circuit). The contacting type adjustable waveguide short is shown in FIG. 6(a), where beryllium springs 121, 122 are used to make a good electrical contact between the moving wall 125 and the inner waveguide wall 165. The disadvantage with using this arrangement is that it can suffer from noisy-contact problems, where, for example, dust particles can compromise the quality of the sliding contact, and the short circuit may become intermittent and lead to erratic electrical behaviour over time after excessive movements in and out of the cavity have taken place. These problems can be overcome by using a non-contacting adjustable short such as that shown in FIG. 6(b). This arrangement ensures that ohmic contact occurs at a zero current point or a point of infinite impedance. At the preferred frequency, both L1 and L2 are $\lambda_g$/4 (or (2n−1)$\lambda_g$/4) long. The L2 line section transforms the short circuit at point A into an open circuit at the contact point B. Any resistance at the contact points is in series with the open and hence the impedance of the combination is infinite, regardless of the value of contact resistance. The L1 line section transforms the infinite impedance into a short circuit at the front face of the non-contacting short. Since the short circuit is independent of the contact resistance, the erratic behaviour associated with contacting-type shorts is avoided. In accordance with the above description, moving wall or moving short 125 will be electrically connected to inner wall 165 of waveguide cavity 160. In the arrangement shown in FIG. 6(b), the sliding wall or sliding short 125 is physically connected to choke arrangement 120, and 120 is physically constructed using two metallic sections 120a and 120b, both of which are connected together using plunger or rod 130.

In the arrangements shown in FIGS. 6(a) and 6(b), a lossy material 124 is shown placed behind the sliding wall. The purpose of this lossy material is to absorb any residual microwave energy that may leak out of the structure. FIGS. 6(a) and 6(b) show a plunger or rod 130 connected to the sliding wall (short) 125 to enable said wall to be moved along waveguide cavity 160.

The variation in reactance $jX_{in}$ as a function of plunger movement inside the waveguide cavity will be as shown on the Smith chart given in FIG. 7. FIG. 7 shows 28 calibration points positioned around the outer circumference of the Smith chart. Points 1 and 15 represent a short circuit and an open circuit condition respectively, points 2 to 14 provide values of inductive reactance, and points 16 to 27 provide values of capacitive reactance. It has been assumed that the waveguide cavity is lossless, i.e. as sliding short 125 traverses away from the distal tip of surgical antenna 400, the insertion loss or transmission loss is negligible. This is in fact a valid assumption to make since at the preferred frequency of interest (14.5 GHz) the lateral movement required to enable travel all around the circumference of the Smith chart (from the generator to the source and back to the generator again, or from the short circuit position to the open circuit position and back to the short circuit position again) is around 10 mm. In order to minimise insertion loss, it is preferable to silver plate the inside wall 165 of the waveguide cavity 160. If waveguide cavity 160 is made from a lossy material then the loss will be represented on the Smith chart as circles with smaller diameters or a spiral rather than a circle, where the tip of the spiral moves closer to the centre of the Smith chart.

Figure 8:
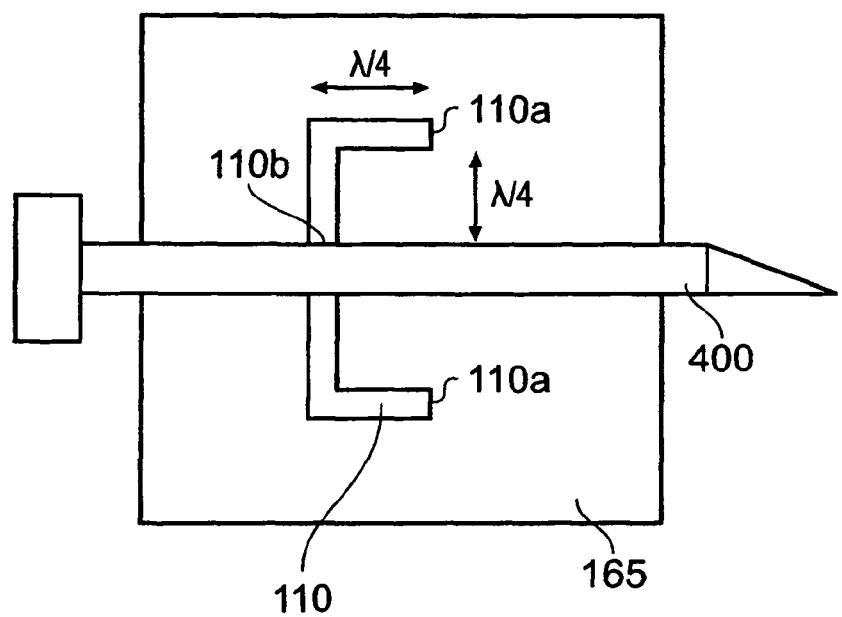
FIG. 8 shows a choke arrangement for the calibration system of the invention.

An illustration of the operation of a waveguide choke is given in FIG. 8. The total length of the choke 110 is a half wavelength at the frequency of interest. Since the far end 110a is a physical short circuit, an electrical short circuit is placed at the wall of the region where the surgical antenna is located 110b. This arrangement allows the antenna to be inserted inside the calibration unit 100 through antenna holder 150 without the need for a physical contact between the outer wall of surgical antenna 400 and calibration unit 100. This is particularly advantageous when the outer wall of surgical antenna 400 is coated with a thin layer, for example 104 m, of biocompatible material, since an interference fit (or even a tight fit) may cause the biocompatible material to be scraped off. The ability of choke 110 to form a short circuit will be somewhat dependant upon the shape of the choke in practice. For example, if the choke is circular then the difference between the inner and outer radii needs to be a bit more than a quarter wavelength at the frequency of operation because the actual wavelength in the radial cavity is determined by Bessel functions not sine functions as is the case for rectangular waveguide sections, therefore the wavelength close to the axis is longer and becomes nearly the same as for free space at large radii.

Figure 9:
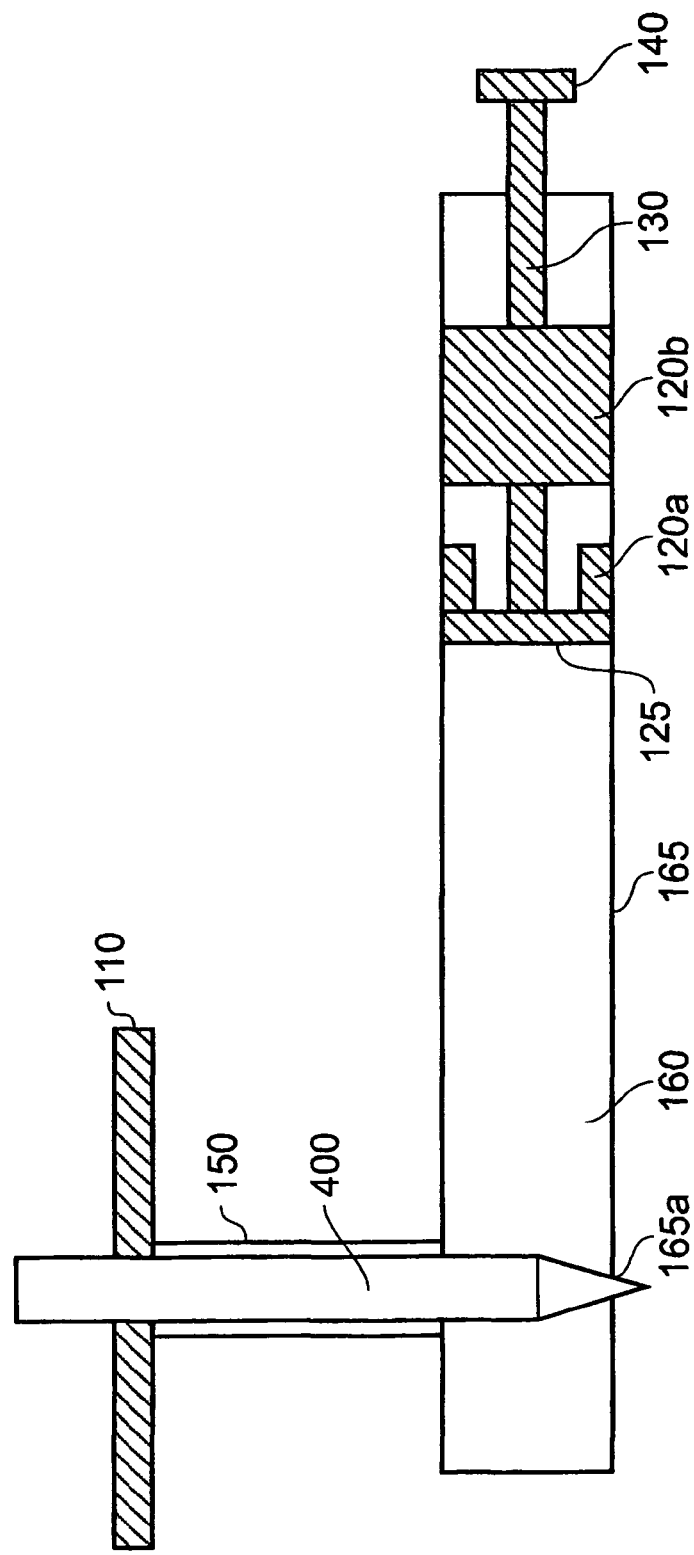
FIG. 9 shows a sectional view through a calibration unit that is an embodiment of the invention.

FIG. 9 shows a section through a calibration system that uses the sliding short circuit 125 to enable the distal tip of surgical antenna 400 to be exposed to a number of impedances between a short circuit and an open circuit. The position of the sliding short 125 with respect to the distal tip of the surgical antenna 400 determines the impedance seen by said tip. So long as waveguide cavity 160 is a lossless structure, the impedance seen will either be short circuit (0Ω), open circuit (∞ Ω), an inductive reactance, or a capacitive reactance. In theory, all impedances will be realised by a movement of the sliding short 125 of a half the wavelength at the frequency of interest. Further movement past the half wavelength position will cause the distal tip of surgical antenna 400 to see the same impedance as before, i.e. ¾λ will give an open circuit, λ will give a short circuit, etc. In the arrangement shown in FIG. 9 the distal tip of surgical antenna 400 fits inside a small hole 165a which is used to locate the antenna. First choke 110 is used to create a short circuit between the inner wall of antenna holder 150 and the outer wall (or conductor) of surgical antenna 400. Second choke 120 is used to create a short circuit between the inner wall 165 of waveguide cavity 160 and the sliding short 125. Plunger or rod 130 is attached to second choke 120a/120b and sliding short 125 to enable said sliding short 125 to be moved in and out of waveguide cavity 160. Plunger 130 is connected to an Actuator (not shown) using a mechanical linkage 140.

The size of waveguide cavity 160 is determined by the frequency used by the system to perform the calibration procedure. Table 1 provides a list of standard waveguide cavities with physical dimensions for the waveguide cavity and the frequency range over which the waveguide cavities can be used. If the cavity size is smaller than that required for the operating frequency range then the electromagnetic fields may not propagate inside the waveguide, i.e. the wave is cut-off. The preferred embodiments used in the calibration systems herein are either waveguide 17 (WR75) or waveguide 18 (WR62) which enable dominant mode ($TE_{10}$) operation at 14.5 GHz (the preferred frequency of interest). Operation at other frequencies is possible using the same or different waveguides, based on the information in Table 1.

TABLE 1 waveguide cavity characteristics

| Waveguide type | Frequency range (GHz) | Outer dimensions and wall thickness (mm) | Cut-off wavelength for $TE_{10}$ mode (mm) | Cut-off frequency for $TE_{10}$ mode (GHz) |
| --- | --- | --- | --- | --- |
| WR187 (WG12) | 3.95-5.85 | 50.8 × 25.4 × 1.626 | 95.0 | 3.16 |
| WR159 (WG13) | 4.90-7.05 | 43.64 × 23.44 × 1.626 | 80.9 | 3.71 |
| WR137 (WG14) | 5.85-8.20 | 38.1 × 19.05 × 1.626 | 69.8 | 4.29 |
| WR112 (WG15) | 7.05-10.0 | 31.75 × 15.88 × 1.626 | 57.0 | 5.26 |
| WR90 (WG16) | 8.20-12.4 | 25.4 × 12.7 × 1.27 | 45.7 | 6.26 |
| WR75 (WG17) | 10.0-15.0 | 21.59 × 12.07 × 1.27 | 38.1 | 7.88 |
| WR62 (WG18) | 12.4-18.0 | 17.83 × 9.93 × 1.02 | 31.6 | 9.49 |
| WR42 (WG20) | 18.0-26.5 | 12.7 × 6.35 × 1.02 | 21.3 | 14.1 |
| WR34 (WG21) | 21.7-33.0 | 10.67 × 6.35 × 1.02 | 17.3 | 17.3 |
| WR28 (WG22) | 26.5-40.0 | 9.14 × 5.58 × 1.02 | 14.2 | 21.1 |

The frequency of operation also determines the physical dimensions of first choke 110 and second choke 120a/120b. This invention is not restricted to using a rectangular geometry for the waveguide cavity; it may be desirable to use cylindrical or square geometries or any other suitable shape.

It is desirable for the calibration frequency to be high enough (or the geometry of the waveguide used to be large enough) to ensure that the electromagnetic wave can propagate inside the waveguide, i.e. the frequency used is above the cut-off frequency, and that the waveguide introduces a minimal amount of power loss (or insertion loss) at the frequency of interest.

For example, if a rectangular waveguide is used then the length of the broad wall (longest length) must be at least one half of the wavelength at the frequency of interest, or for a cylindrical waveguide, the diameter should be at least one half of the wavelength at the frequency of interest.

Figure 10A:
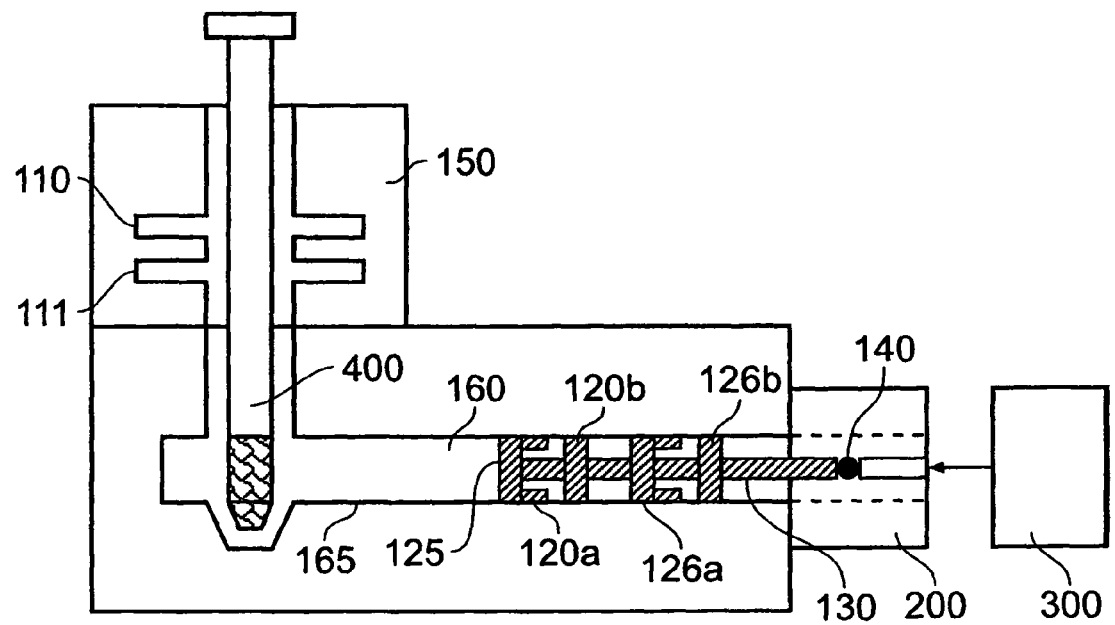
FIG. 10 shows a calibration assembly with a plurality of chokes that is another embodiment of the present invention.

FIG. 10(a) shows a calibration system that may be used to calibrate a waveguide type antenna structure where the distal tip radiator (the aerial) is a ceramic blade structure. This figure illustrates that it is possible to perform distal tip calibration on antenna structures that have been developed for various applications. In other words, the method of performing distal tip calibration using a sliding short can used to perform a one port calibration on any suitably designed microwave antenna structure.

The calibration unit shown in FIG. 10(a) uses two chokes 110, 111 to ensure that the antenna structure 400 is electrically short circuited to antenna holder 150 without the need for physical contact to be made between the inner wall of antenna holder 150 and the outer wall of surgical antenna 400. The use of a two choke arrangement may reduce any electric field leakage that comes from (or radiates out of) the gap between the hole or channel made for the antenna holder 150 and surgical antenna 400. The calibration unit may also use two chokes 120a/120b, 126a/126b connected to the sliding short 125 to ensure that the inner wall 165 of waveguide cavity 160 is electrically shorted to the sliding short without the need for a physical contact to be made, thus ensuring that the sliding short can be moved in and out of waveguide cavity 160 with ease. The use of two chokes may ensure that a better short circuit is made, and that any leakage field that may emanate (or radiate) out of the cavity is minimised.

The greater the number of chokes used, the better the short circuit, and the lower the leakage field.

Figure 10B:
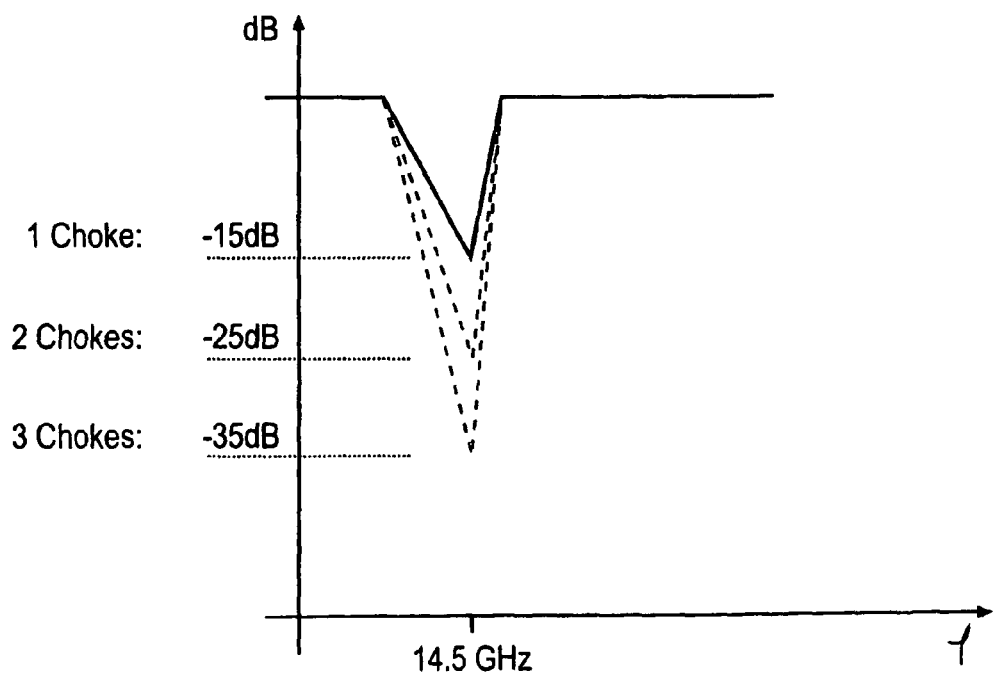

FIG. 10(b) illustrates the effect of using a plurality of chokes in terms of leakage power level at the frequency of interest. It can be seen that the leakage power is reduced as the number of chokes is increased. The choke arrangements given here are particularly suitable for a system that uses a single frequency since the exact physical lengths needed to produce half wavelength chokes may only be strictly valid at one frequency. In reality, a variation in frequency around a centre frequency will not drastically affect the ability of the choke to create the desired short circuit condition, but the effectiveness will degrade as the frequency moves away from the frequency at which the choke length is an exact multiple of a half wavelength. The physical length of the choke may be a half wavelength at the frequency that lies at the centre where the unit is required to operate over a band of frequencies, or the choke may have a stepped profile.

Figure 11:
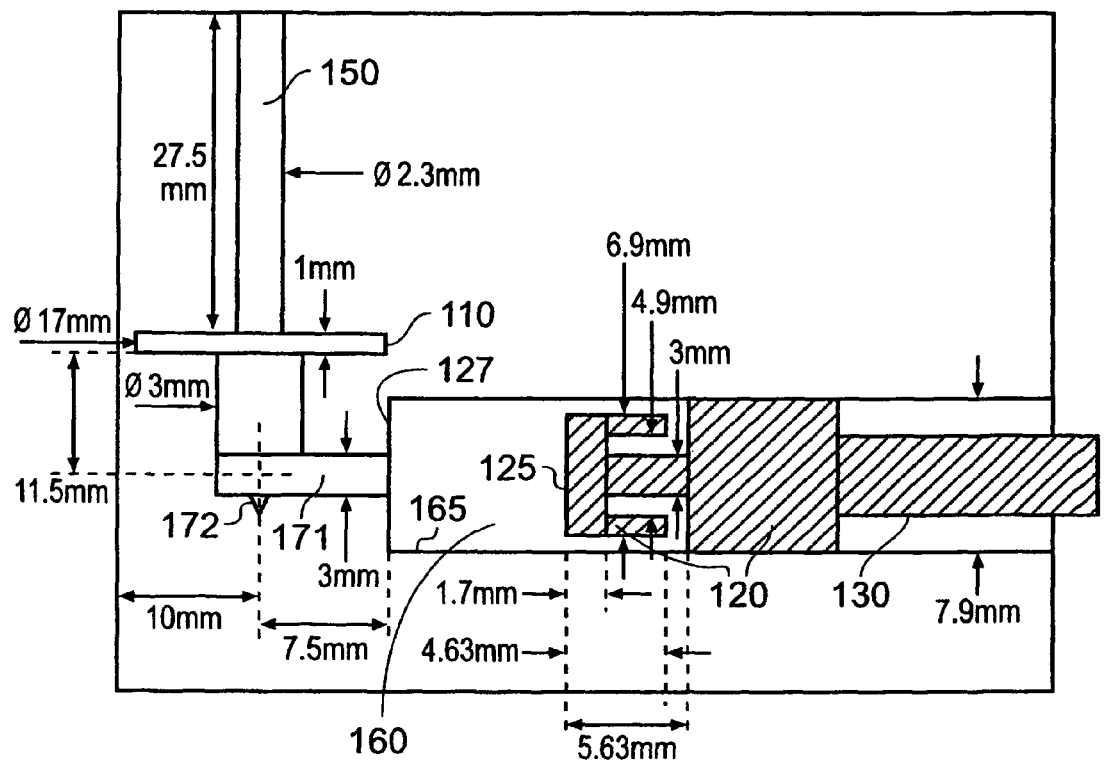
FIG. 11 shows another embodiment of a calibration assembly with dimensions for a practical system.

FIG. 11 shows the cross-section through the side of a specific embodiment for the sliding short calibration system. Suitable dimensions are shown, although the drawings are not to scale. This design was modelled using Computer Simulation Tools (CST) Microwave Studio® where the effectiveness of first choke 110, second choke 120, and sliding short 125 was evaluated. It was found that the position of sliding short 125 required to enable distal tip of surgical antenna (not shown) to see a short circuit was about 4 mm from the end wall 127 of waveguide cavity 160. The inside diameter of antenna holder 150 was chosen to enable a co-axial antenna with an outside diameter of 2.2 mm to fit inside the calibration unit. The chosen hole diameter of 2.3 mm also allows for the surgical antenna to be coated with a thin layer of biocompatible material, for example, a 10 μm conformal coating of Parylene C. A location hole 172 was drilled, to enable the tip of the surgical antenna to be located inside the calibration unit. The depth of hole 172 was chosen to allow for a majority of the radiating monopole (the aerial) of surgical antenna to be exposed to sliding short 125. Second choke 120 provided a good short circuit between sliding short 125 and waveguide wall 160. The complete assembly was made from brass, which is a low loss material and can be machined with relative ease. The structure was optimised to operate at a fixed frequency of 14.5 GHz and the dimensions given for the structure, shown in FIG. 11, were used in the electromagnetic field simulations that were performed on the structure.

Figure 12:
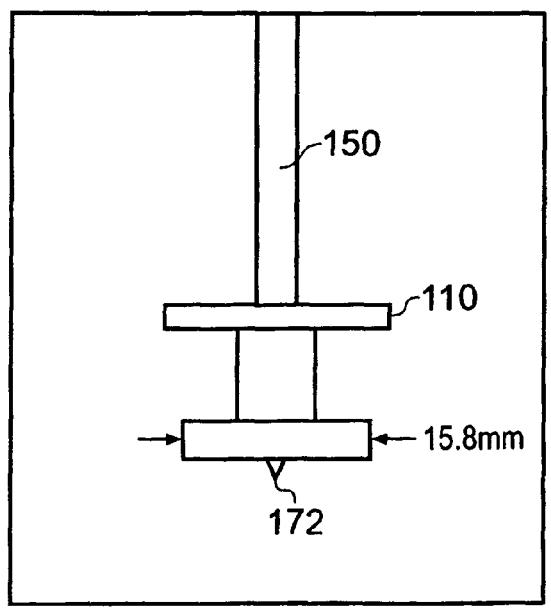
FIG. 12 shows an end view of the calibration system shown in FIG. 11.

FIG. 12 shows the same specific embodiment, but this time the end view is given. It can be seen that the inner diameter of the antenna holder 150 below first choke 110 is increased to 3 mm.

Figure 13:
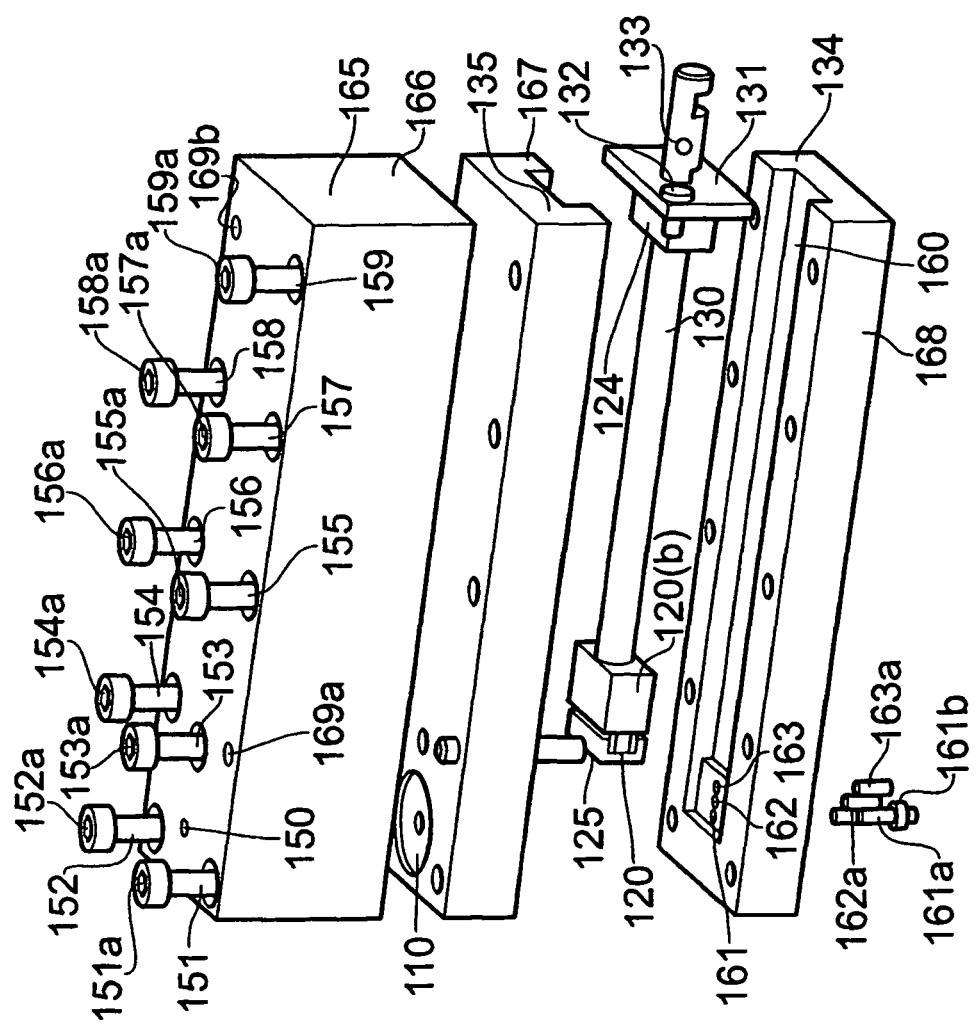
FIG. 13 shows a three dimensional view of a calibration assembly that is another embodiment of the present invention.

FIG. 13 shows a full assembly of the sliding short waveguide calibration unit that is an embodiment of the invention. The unit is made from brass and comprises of four main sections. The first section is top block 166, which comprises a hole 150 for antenna holder to be inserted, eight holes 151, 152, 154-159 for M4×35 mm long cap head stainless steel assembly bolts to be fitted, two holes 169a, 169b for 4 mm diameter×25 mm long silver steel dowel pins to be fitted, and one hole 153 for a M4×20 mm cap head stainless steel bolt.

The second section is middle section 167 with holes corresponding to those in top block 166 and also comprises one hole 135 for M2.5 pan head stainless steel screw to be fitted to secure plunger mounting plate 131, a milled recess 110 to form first choke, and one half of waveguide cavity 160.

The third section is the plunger assembly 130, which comprises sliding short 125, second choke 120a/120b, plunger mounting plate 131 with a block of material attached to the back 124 (this material may be microwave energy absorbing material that can be used to absorb any leakage fields that may be present due to a non perfect short circuit between the inner walls 165 waveguide cavity 160 and the second choke 120a/120b), and two holes 131 in plunger mounting plate for M2.5 pan head stainless steel screws 132, 133 to be fitted.

The fourth section is, the bottom section 168, which comprises a hole 150 for antenna 400 to be fitted (this hole only allows a portion of surgical antenna to be inserted through the cavity), eight holes 151, 152, 154-159 for M4×35 mm long cap head stainless steel assembly bolts to be fitted, two holes 169a, 169b for 4 mm diameter×25 mm long silver steel dowel pins, one M2.5 tapped hole 161 to allow M2.5 brass tuning screw to be fitted to enable the position of the distal tip of surgical antenna to be adjusted in the vertical plane to enable the calibration unit to accommodate variations in the design of the distal tip of the surgical antenna (the aerial), two M2 tapped holes 162, 163 to allow M2 tuning screws to be fitted, and the second half of waveguide cavity 160.

The M2 brass tuning screws 162a, 163a are tuning stubs and are used to tune the system to accommodate for variations in the design of the distal tip (the aerial) contained within the surgical antenna structure. These variations may be due to variations in the manufacturing process or due to the need to calibrate a range of different surgical antenna designs. The inclusion of tuning screws 161a, 162a and 163a enables the calibration unit to be flexible in terms of being able to accommodate variations in the design of the surgical antennas. The calibration unit is not limited to surgical antennas and may be used to calibrate other antennas with similar physical geometries that are suitable for use in other applications.

Figure 14:
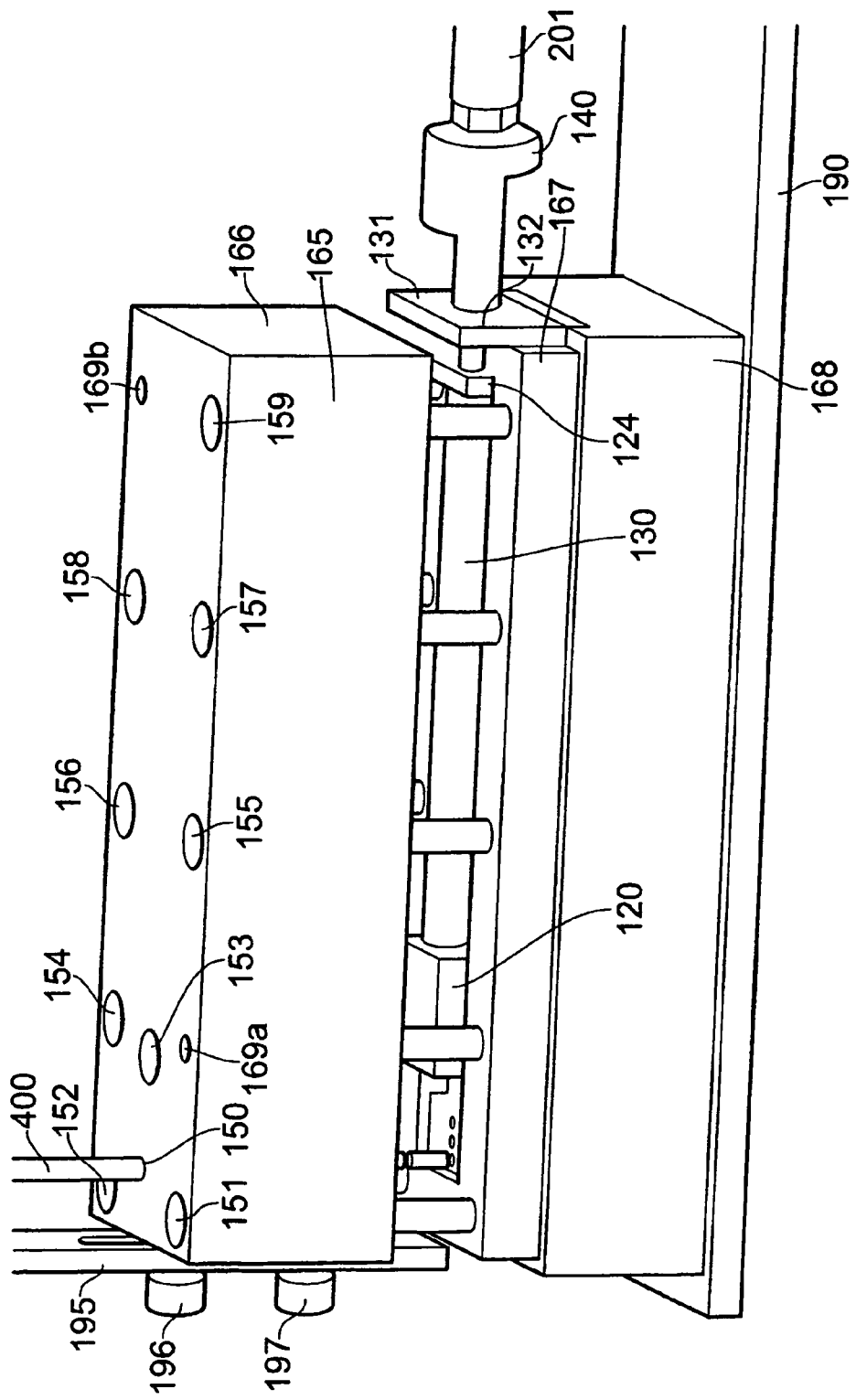
FIG. 14 shows a partially assembled three dimensional view of the calibration assembly shown in FIG. 13.

FIG. 14 shows another drawing of the complete assembly, but this time with the assembly mounted on a plinth 190, which is also used to mount electromechanical actuator 200 (not shown). A section of adjustable surgical antenna guide 195 is shown along with guide mounting screws 196, 197. FIG. 14 also shows surgical antenna 400 inserted into antenna holder 150. It can be seen that the distal tip of surgical antenna 400 fits inside M2.5 tapped hole 161 to a level that is determined by the adjustment of M2.5 brass tuning screw 161a. FIG. 14 also shows mechanical linkage 140 and a section of movable actuator rod 201.

Figure 15:
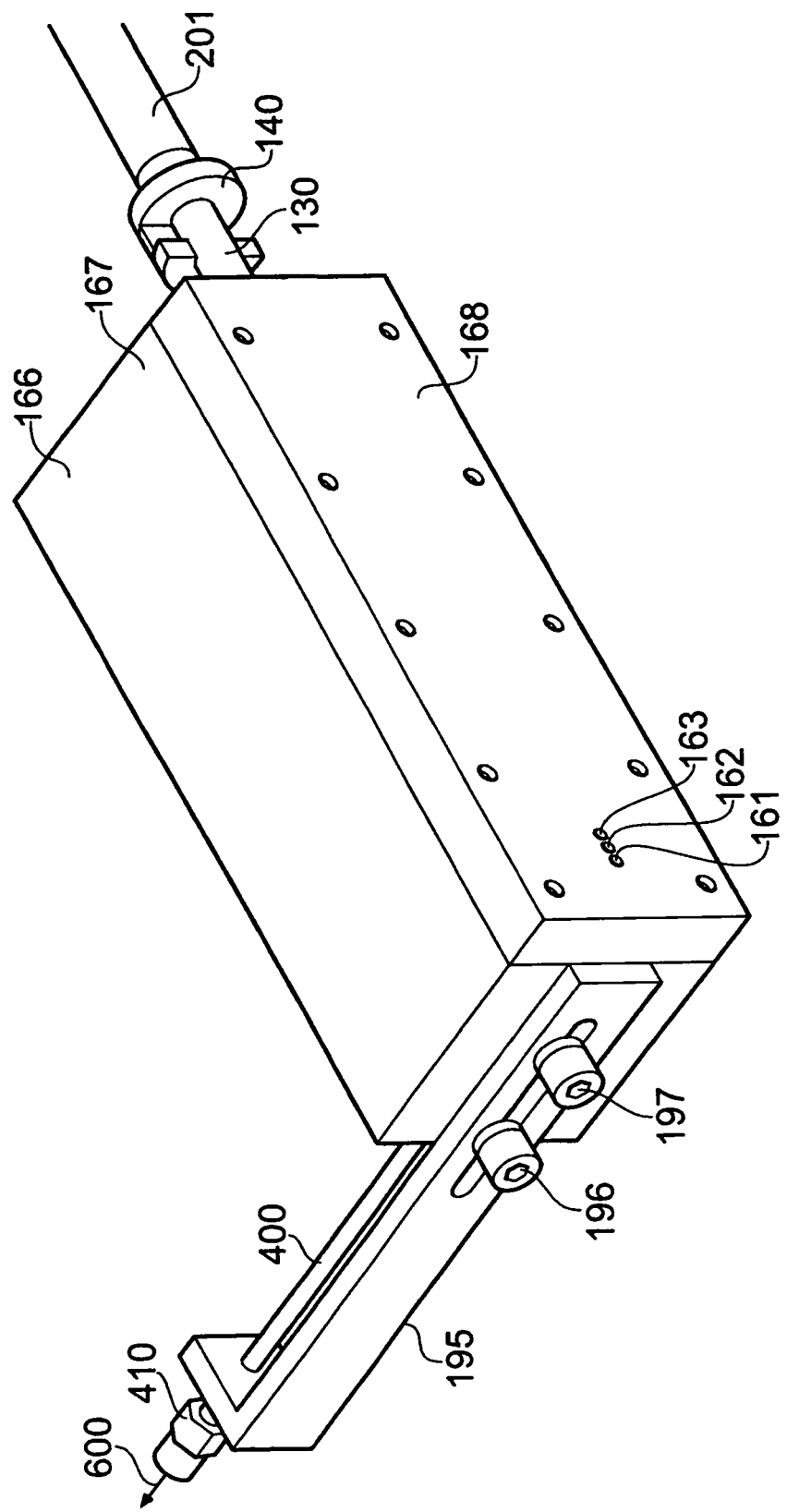
FIG. 15 shows the fully assembled calibration assembly of FIG. 13.

FIG. 15 shows a calibration assembly with an adjustable surgical antenna guide 195. Again, surgical antenna 400 is shown inserted into calibration assembly 100. The supporting section of adjustable surgical antenna guide assembly 195 is located near microwave connector 410 which is used to interface co-axial cable assembly 600 with surgical antenna 400. It is desirable for the supporting section of adjustable guide 195 to be close to said connector 410 since the outside diameter of cable assembly 600 is likely to be several orders of magnitude greater than the outer diameter of surgical antenna 400, thus the loading caused by the weight of cable assembly 600 could otherwise cause the rigid co-axial section of surgical antenna 400 to bend or an unnecessary force may be exerted on the antenna shaft, which may result in the shaft bending. FIG. 15 also shows the location of three tapped holes 161, 162, 163 for tuning screws 161a, 162a, 163a. From this drawing it can be seen that said tuning screws will be inserted into the waveguide assembly from the bottom, thus plinth 190 has a thickness or height to enable said screws to be inserted with a minimal length of thread inside the holes whilst allowing the calibration unit 100 to sit flat. It is necessary to mill a slot out of plinth 190 to enable said tuning screws to be fitted and adjusted.

Figure 16:
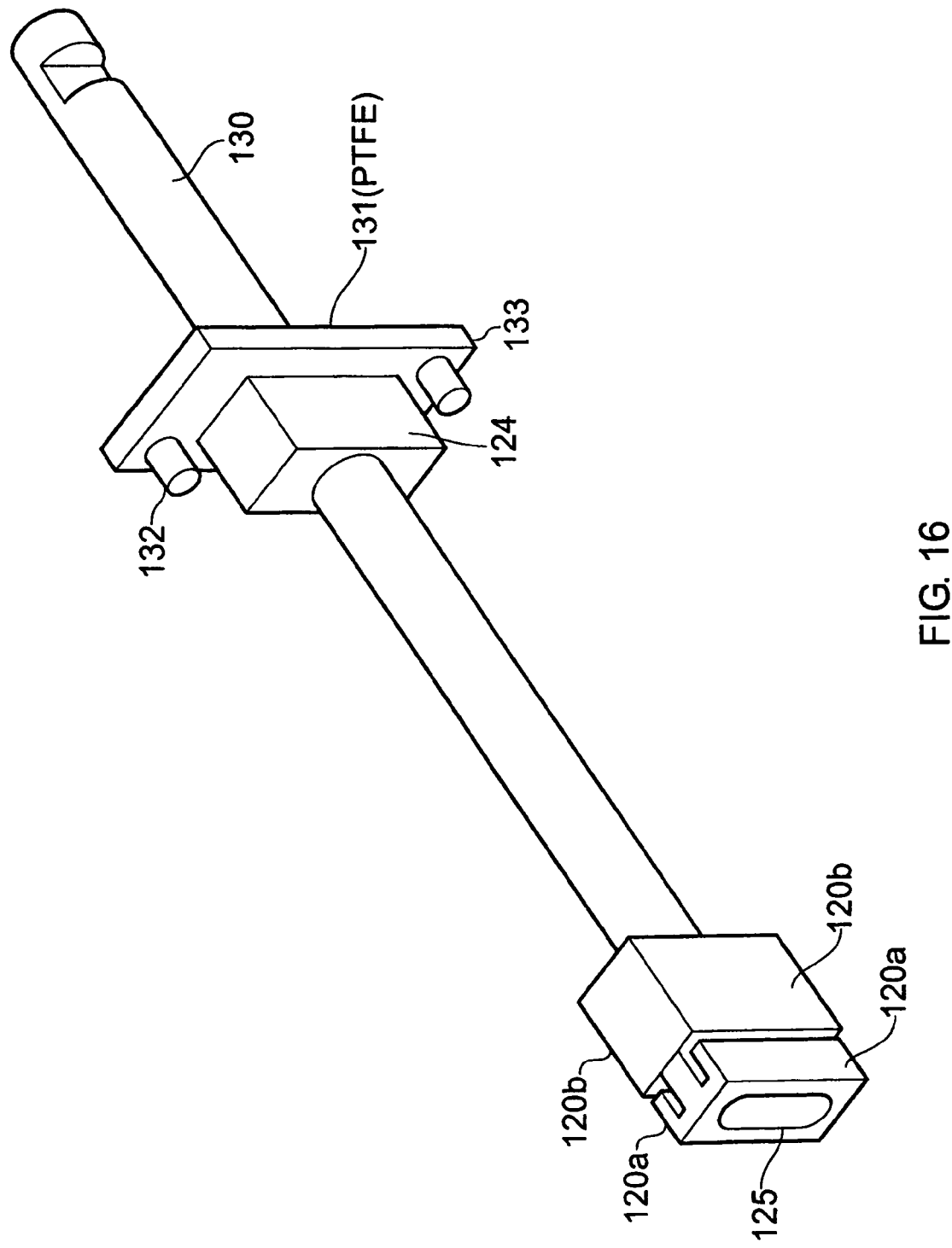
FIG. 16 shows a three dimensional view of the plunger used in the calibration system of FIG. 13.

FIG. 16 shows plunger 130 and second choke 120a, 120b. In this specific embodiment, silver steel is used as the material of plunger 130, and second choke 120a, 120b is made from brass and soldered to the end of rod 130. The face of sliding short 125 may be machined subsequent to the soldering process to ensure that any imperfections in the solder joint have been removed and that the face of 125 is flat. A mounting plate 131 is also connected to plunger 130 for the purpose of securing the structure to the rest of the calibration assembly. Two fixing screws 132, 133 are used to hold the structure in place. A non metallic block of material 124 is attached to mounting plate 131. The purpose of 124 is to support an assembly comprising of plunger 130 and second choke 120a, 120b contained within waveguide cavity 160. The material of choice for 124 may be a material that absorbs microwave energy, for example, an RF foam from R&F Products (ref. http://www.randf.com/rf foam.html). These RF foams can be optimised for reflection loss or insertion loss and a brief summary of suitable materials is given in Table 2.

TABLE 2

RF Foam absorbing products available from R&F Products

| Product | Description |
| --- | --- |
| RFLS | Single layer lossy foam for insertion loss range from 1 dB t0 50 dB per inch. Thickness range from 0.125" to 4.5" |
| RFML | Multilayer foam made up of three RFLS layers. Layered structure gives a good broadband absorption over a wide frequency range |
| RFRET | Reticulated foam with a continuously graded lossy coating. Provides optimum in broadband performance with the lowest weight |
| RFWP | Waterproof foam |
| RFRIGID | Rigid version of RFRET |

These foams are often referred to as radar absorbing materials (RAM) and the materials comprise of coatings whose electrical and magnetic properties have been altered to allow absorption of microwave energy at discrete or broadband frequencies.

Figure 17:
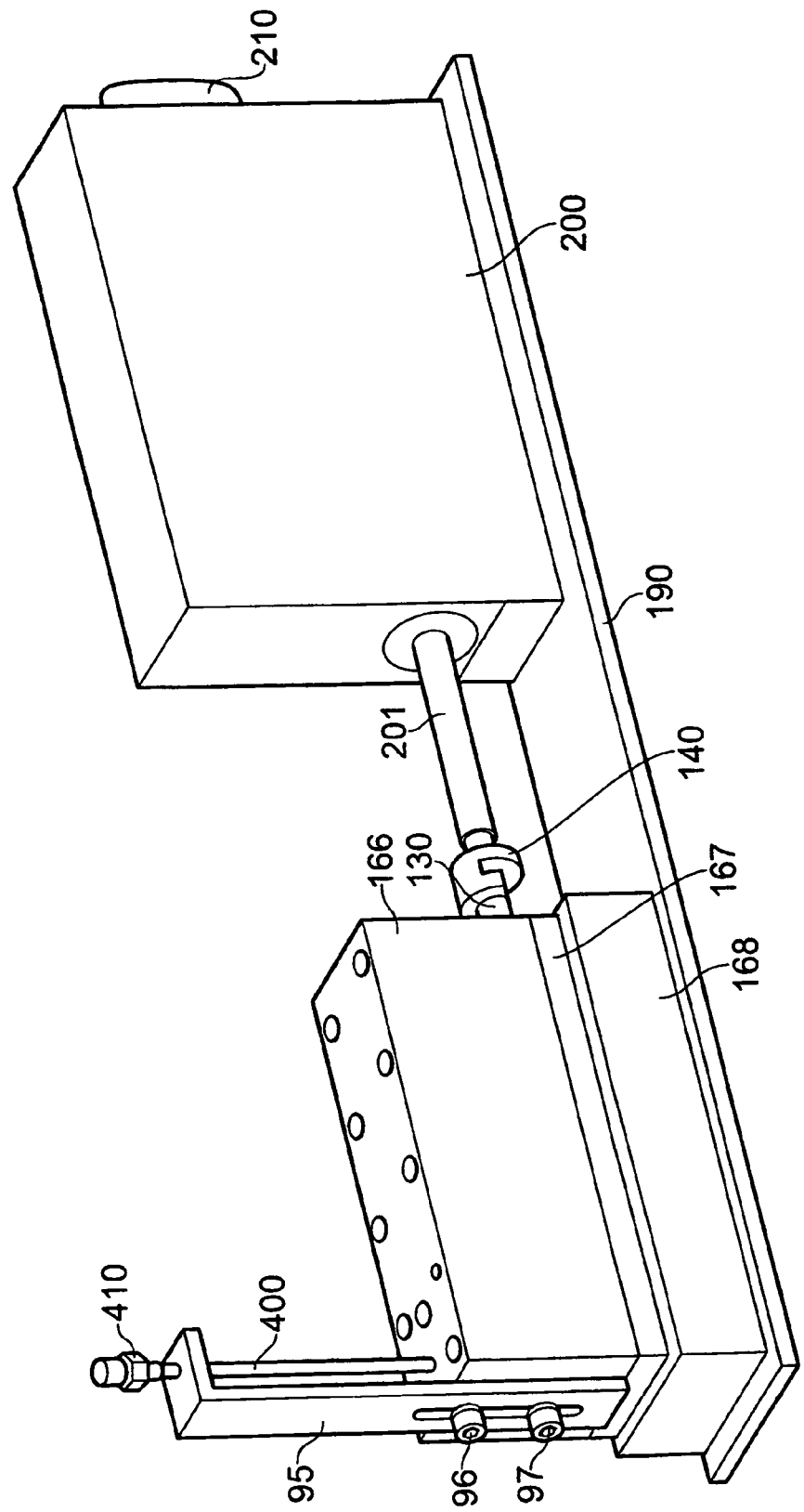
FIG. 17 shows a three dimensional view of a full calibration system according to the present invention.

FIG. 17 shows a complete mechanical and electromechanical embodiment of an automated calibration unit. Electromechanical actuator (linear motor) 200 is shown mounted onto plinth 190 and moveable shaft 201 is coupled to plunger 130 using mechanical linkage 140. Connector 210 is used to supply the electrical input signals necessary to drive electromechanical actuator 200. These signals are suitably conditioned signals produced by actuator controller 300. Said controller 300 may provide proportional, integral, or differential control to introduce gain, prevent overshoot and provide a fast actuator response time respectively. The signals provided by actuator controller 300 to actuator 200 are based on the signals derived or developed in digital signal processor/microprocessor unit 800, and these signals are based on measured information or user commands supplied to the system.

Figure 18:
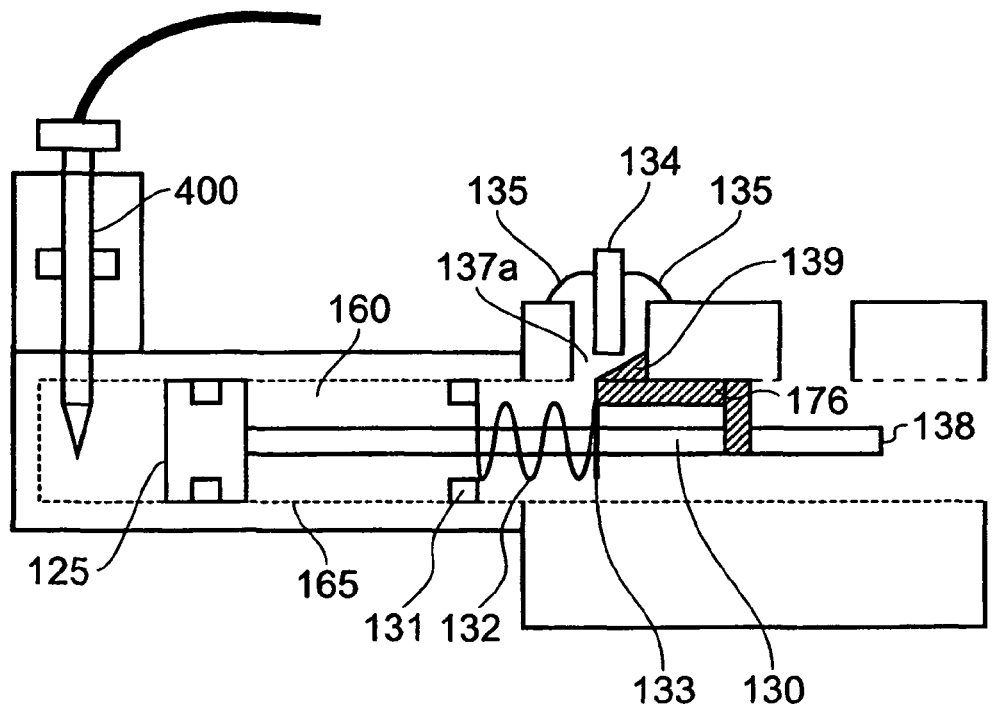
FIG. 18 shows a calibration unit with a retractable mechanism that is another embodiment of the present invention.
Figure 19:
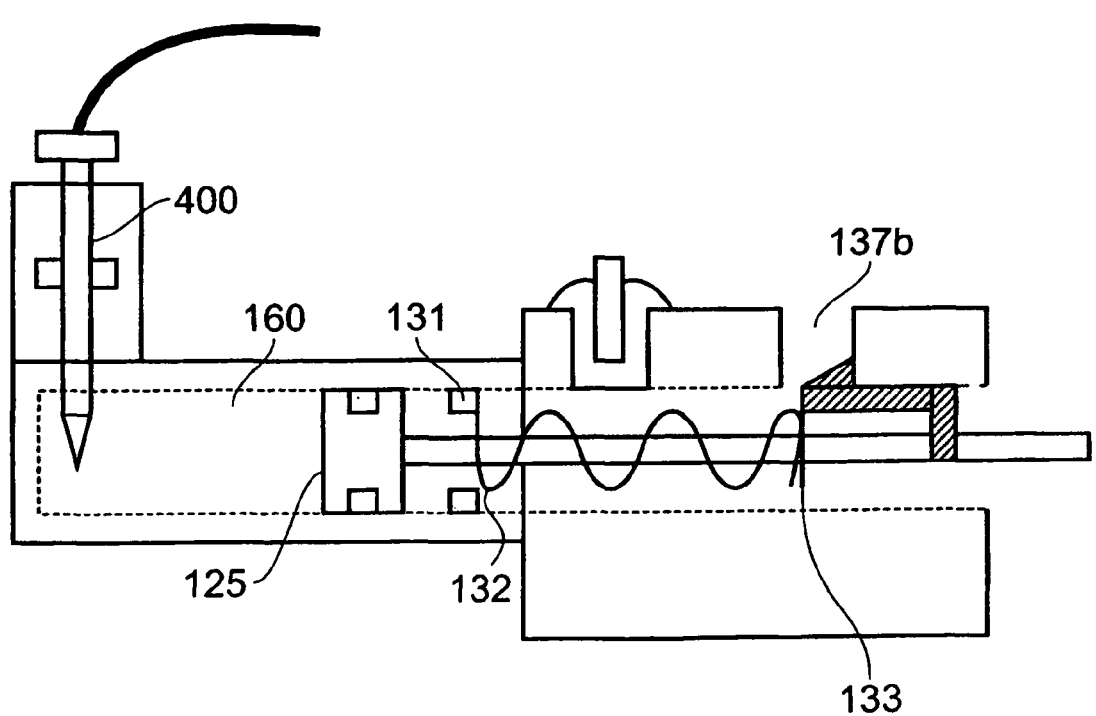
FIG. 19 shows the calibration assembly of FIG. 18 in a retracted position.

FIGS. 18 and 19 show another embodiment of a calibration system that is based on the same principle of moving a sliding short 125 inside a waveguide cavity 160 to enable the distal tip of surgical antenna 400 to be subjected to different impedances. In this embodiment the system is completely mechanical. FIG. 18_shows an arrangement that uses a retractable mechanism similar to that used in the operation of a ball point pen. FIG. 18 shows the position of the sliding short 125 with respect to the distal tip of surgical antenna 400 set to enable the distal tip to see a short circuit condition. This position is achieved by machining a ledge 131 into the wall of waveguide cavity 160 to enable the end of a spring 132 to be permanently attached (or remain in contact) and remain positioned even when spring 132 is under tension, i.e. the spring must not come through the inside diameter of ledge 131. The opposite end of spring 132 is attached to a plate (or disk) 133 whose diameter is larger than the diameter of spring 132 to prevent the spring extending past said plate, thus spring 132 is contained within the region between ledge 131 and plate 133. In the arrangement shown in FIG. 18, spring 132 is compressed by physically pushing the end cap 138 to enable a toothed projection 139 on resiliently deformable member 136 to be located in recess 137a. Resilient member 136 is permanently attached to plunger 130. It may be preferable for member 136 to be made from a plastic material. The position of ledge 131 must be such as to allow sliding short to travel a distance that is at least a half of the wavelength at the frequency of operation in order to allow for all points around the circumference of the Smith chart to be captured. Preferably the allowable distance of travel is one wavelength at the frequency of interest in order to ensure correct operation of the system. A block (or button) 134 is attached to the walls of the waveguide 165 using an additional two springs 135. The purpose of block 134 and springs 135 is to enable member 136 to be deformed, thereby releasing projection 139, when a force is applied to block 134 to enable its inner face to push against projection 139. When this operation occurs, spring 132 is under less tension and the projection 139 is located in recess 137b. FIG. 19 shows the condition when spring 132 is released and the projection 139 has moved to position 137b. In this condition, sliding short 125 is moved away from the distal tip of surgical antenna (the aerial) 400 by a distance that enables the distal tip of surgical antenna 400 to see an open circuit condition. Spring 132 is still under some tension to ensure that the position of moving short 125 is fixed and is not loose inside waveguide cavity 160. The mechanical calibration arrangement shown in FIGS. 18 and 19 enable only two calibration points to be measured. In this instance the two points are shown to be an open circuit and a short circuit, but this arrangement is not limited to measuring only these positions, for example, if the movement was to represent an eighth of the wavelength at the frequency of interest in the direction of movement from the short circuit position moving from the source towards the generator, then the impedance seen at the distal tip of surgical antenna 400 would be an inductive reactance equal to the characteristic impedance of the waveguide cavity.

Figure 20:
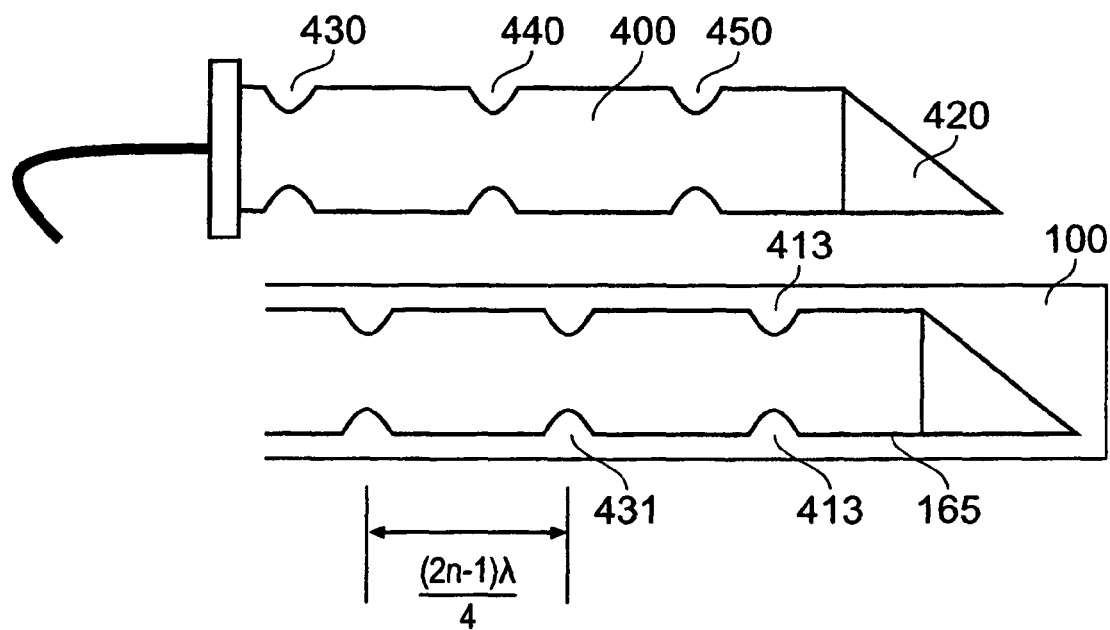
FIG. 20 shows a calibration arrangement which is yet another embodiment of the present invention.

Other distal tip calibration arrangements that may be considered are those using fixed calibration points, where it is necessary to physically attach calibration jig or assembly 100 to surgical antenna 400. It is possible to design and develop a plurality of calibration loads that can be physically or manually attached to the distal tip of the surgical antennas to provide a fixed impedance environment or a suitable calibration standard. Each known standard will enable the distal tip of the antenna to see a different impedance. It is preferable for at least three known impedance standards to be used, for example, an open circuit, a short circuit, and an impedance that is the same as the characteristic impedance of the system (the antenna shaft, cable assembly, microwave components, etc), for example, 50Ω or 75Ω. At least three standards are preferred to ensure that system errors (DC offsets, etc) are removed. FIG. 20 shows an arrangement where a fixed point calibration technique is used to calibrate a surgical antenna. The calibration unit 100 contains three protrusions 413 that are spaced appropriately to allow the distal tip 420 of surgical antenna 400 to be subjected to three different load impedances. Surgical antenna 400 contains three grooves 430, 440, 450 to enable the antenna to be located at three unique positions inside the calibration unit 100. The calibration unit 100 is designed around the geometry of surgical antenna 400 such that surgical antenna 400 fits inside calibration unit 100 where the air gaps between the inner walls 165 of calibration unit 100 and the outer wall of surgical antenna 400 are minimised. It is desirable for the distance between the centre of adjacent notches (and corresponding grooves) to be at odd multiples of a quarter or an eighth of the wavelength at the frequency of interest such that when all three grooves 430, 440, 450 of surgical antenna 400 are in contact with three respective protrusions 413 the distal tip 420 of surgical antenna 400 is subjected to a short circuit condition. A short circuit condition may occur when the tip of the antenna is pushed up against a shorted wall or the tip fits snugly into a matting part.

When the position of surgical antenna 400 within calibration unit 100 has been adjusted such that only the last two grooves 440, 450 are in contact with corresponding protrusions 413 in calibration unit 100, the distal radiating tip 420 of surgical antenna 400 will see an open circuit condition. If the position is changed again such that only the last groove 450 is in contact with first notch then the impedance seen by radiating tip 420 will change yet again. Assuming again that the distance between the centres of adjacent notches and grooves is an odd multiple of a quarter wavelength at the frequency of interest and that the effective waveguide cavity 160 that has been set up is lossless over the distance of interest, the radiating tip 420 of surgical antenna 400 should see a short circuit condition once again.

The protrusions 413 in FIG. 20 may be provided by a spring. Thus, the schematic protrusions shown in FIG. 20 may be replaced by grooves that can fully house ball bearings when the outer wall of surgical antenna 400 pushes against them. Small springs allow ball bearings to take two positions. The first position is where the ball bearings are pushed inside the grooves made in the wall 100 of waveguide cavity 160 to allow surgical antenna 400 to be located, or to be free to move inside calibration unit 100. The second position is where the ball bearings are located inside grooves 430, 440 inside surgical antenna 400 to allow surgical antenna 400 to be located in a fixed position to enable radiating tip 420 to be calibrated. One end of each of the small springs is connected to the surface of its respective ball bearing and the other end is connected to wall 165 of calibration unit 100. This connection may be made using glue, by welding, by soldering, or by any other suitable means. When surgical antenna 400 is located inside calibration assembly 100, it may be preferable for one half (a hemisphere) of the ball bearing to totally-fill a corresponding groove 430, 440. It is desirable for the small_springs to be as rigid as is practically possible in order to prevent movement of the surgical antenna inside cavity 160 of calibration unit 100.

In the embodiment shown in FIG. 20, it is preferable for the waveguide cavity to support the dominant mode of propagation rather than higher order modes of propagation. Since higher order modes of propagation will only exist when the operating frequency is high enough or the waveguide structure is large enough to enable the geometry (diameter or wide wall) to have physical dimensions that are more than one half wavelength at the frequency interest, it is possible that only the dominant mode will be able to propagate.

Suitable materials for the calibration unit 100 in FIG. 20_include aluminium, copper, brass, silver plated steel, silver plated aluminium, or gold plated nickel.

Figure 21:
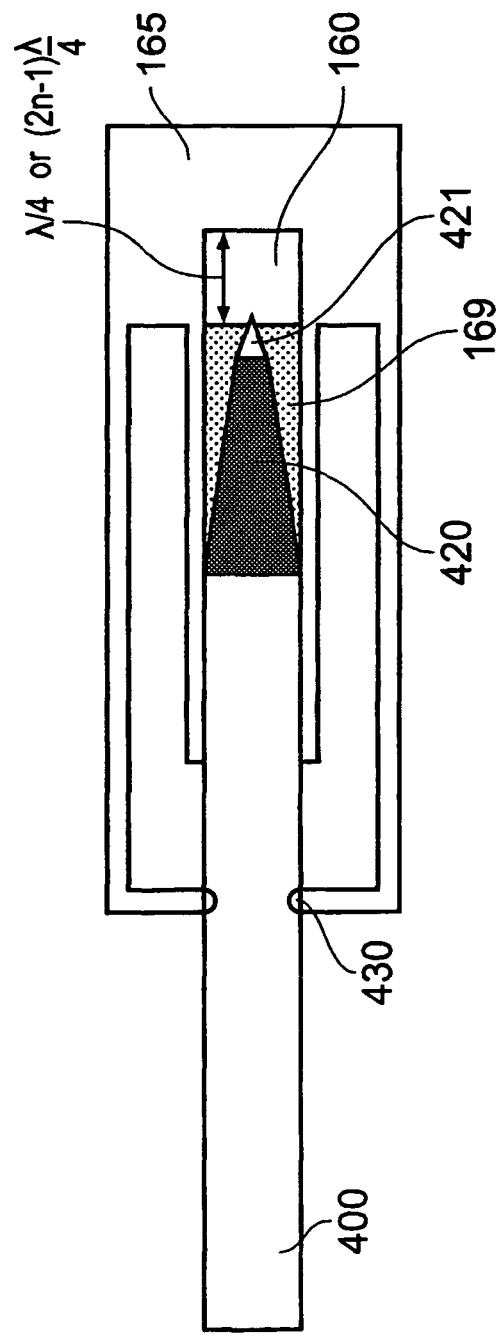
FIG. 21 shows a single point calibration unit that is another embodiment of the present invention.

In certain applications it may be adequate to calibrate the distal tip 420 of the antenna 400 using one calibration point only. Applications where this arrangement may be appropriate include material type or property differentiation where there is a large difference between the characteristics of the material, for example, where a change in the real part of impedance from 100 to 1Ω exists, or where it is only necessary to measure a difference rather than an exact position referenced to a fixed calibration point. Depending upon the required measurement sensitivity, it may be possible to use single point calibration for the treatment/measurement system being developed here to perform dynamic tissue impedance matching and tissue state recognition. FIG. 21 shows an embodiment of a single point calibration arrangement, where a centre conductor 421 of a surgical antenna 400 protrudes into a waveguide cavity 160. In the arrangement shown, the length of the cavity is an odd multiple of the quarter wavelength at the frequency of interest, which may be used to enable the tip of centre conductor 421 to see an open circuit load. The material used to fill waveguide cavity 160 is air, but other materials may be used. It may be desirable to fill the cavity with a material that exhibits a high relative permittivity at the frequency of interest to enable said cavity to support the dominant mode of propagation whilst keeping the physical dimensions of the cavity as small as possible. In an alternative embodiment, the distal tip of centre conductor 421 may contact with wall 165 of the calibration assembly body to enable said tip 421 to be exposed to a short circuit load. In this instance it is preferable for calibration material 421 to be the same as wall material 165 and for this material to be a good conductor. If the two materials are the same and they exhibit the properties of a good conductor then both the overall distal tip of the radiating section (the aerial) 420 of surgical antenna 400, and the tip of centre conductor 421 will see a short circuit load.

Figure 22A:
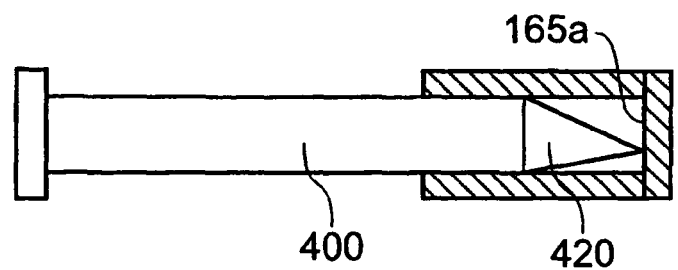
FIG. 22 shows a calibration assembly for a coaxial antenna that is another embodiment of the present invention.
Figure 22B:
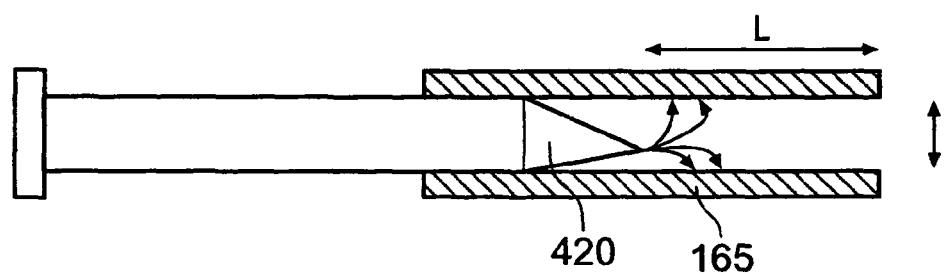
Figure 22C:
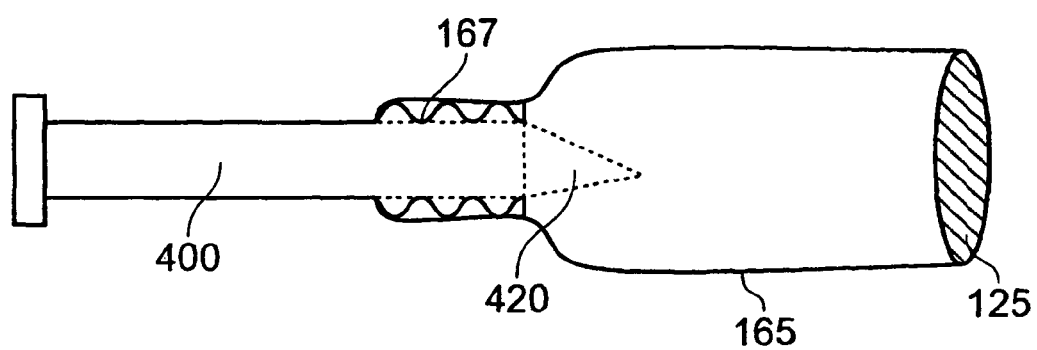

FIG. 22 depicts a single point calibration arrangement that uses co-axial loads rather than the waveguide loads or waveguide cavities that are discussed above. A co-axial version of a short circuit load or calibration point connected to the distal radiating tip 420 of surgical antenna 400 is shown in FIG. 22(a).

The co-axial short circuit load is realised by terminating the end of radiating tip 420 with a metal plate 165a. Said plate 165a creates a boundary at which the electric field associated with the transverse electromagnetic (TEM) mode is zero. Thus the reflection coefficient is −1, which is the reflection coefficient for a short circuit. At low frequencies it would be possible to connect the tip of inner conductor to the outer conductor of antenna 400 to obtain a good short circuit load, but at microwave frequencies considered in this work the reactance associated with the inductance of the wire will be appreciable and also some of the field would radiate out of the end of 420, thus adding a resistive component to the terminating impedance. The co-axial version of the open circuit load is shown in FIG. 22(*b*). In this arrangement, the wall 165 of the calibration fixture extends past the radiating tip 420 to prevent radiation emanating out of the end of the structure. In this case, the inside diameter of the calibration fixture must be chosen so that the circular waveguide section is below cut-off at the highest frequency of interest. The length L should be chosen to be sufficient to attenuate the dominant mode ($TE_{11}$) by at least 20 dB to ensure that all modes will be attenuated by at least this amount, hence negligible radiation will be produced at the end of the structure.

The co-axial version of the sliding short circuit load is shown in FIG. 22(*c*). In this arrangement, a metallic tube 165 slides over the outer conductor of surgical antenna 400 and a good electrical contact between the outer wall of 400 and the inner wall of 165 is made using beryllium copper spring fingers 167. This sliding short arrangement may be used to vary the reactance seen at the distal tip of radiating antenna section 420. All values of reactance from 0Ω (short circuit) to ∞ Ω (open circuit) are available by moving the sliding load over a distance equal to a half of the wavelength at the frequency of interest (or the calibration frequency). The half wavelength movement corresponds to a change in reflection coefficient from −1 to +1 respectively. It is assumed that when the distal tip of radiating antenna section 420 is in contact with end plate 125 attached to sliding short, then a short circuit load is produced. The arrangement shown in FIG. 22(*c*) takes advantage of the impedance transforming properties of a lossless transmission line.

Figure 23:
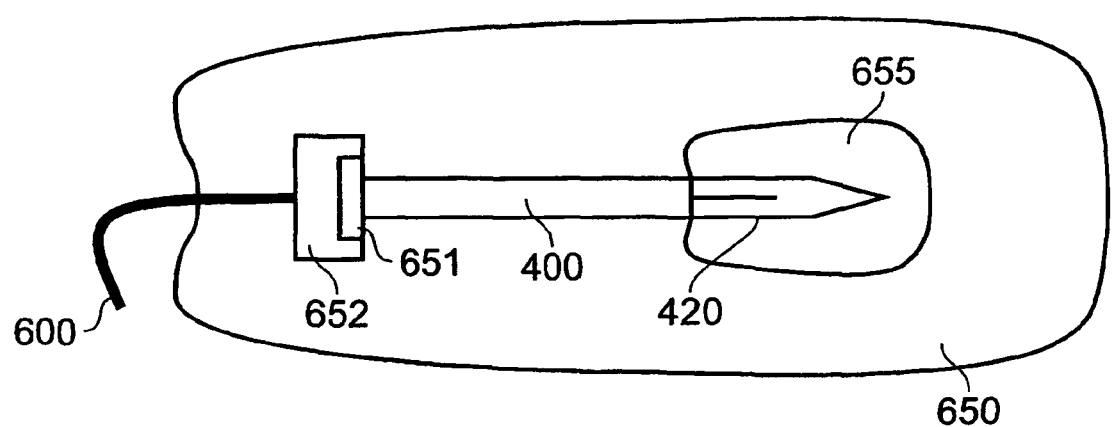
FIG. 23 shows an antenna in a sterile packaging suitable for a single point calibration.

FIG. 23 shows a single point calibration arrangement where the calibration load is integrated within the antenna and cable assembly packaging system. In the arrangement shown in FIG. 23 the radiating antenna section 420 is surrounded with a material 655 that is used to provide the stable calibration load and said calibration load 655 differs from the material used to provide sterile housing (or sterile environment) 650 for cable assembly 600 and surgical antenna 400. It is desirable to use the same material for the calibration load 655 and sterile packaging 650 in order to simplify the manufacturing process. The radiating tip 420 should be fully immersed inside calibration material 655 (650) and it must be ensured that there are no air gaps between 420 and 655 (650) to ensure that the system is calibrated to a known load. Considerations must also be given to the electrical and mechanical composition of the material used for 655 and/or 650, for example the material must be consistent in terms of density of material around radiating tip 420 in order to minimise variations in material characteristics, for example, low density PTFE may slightly change its value of relative permittivity when squashed. The arrangement shown in FIG. 23 shows flexible cable assembly 600 connected to surgical antenna 400 by way of an SMA female 651 that is connected to the proximal end of surgical antenna 400 an SMA male 652 that is connected to the distal end of cable assembly 600 and a first material (calibration material) 655 covering the distal radiating tip 420 of surgical antenna 400. The complete structure is enclosed in a sterile bag or housing 650. The assembly will remain inside sterile housing 650_until the calibration procedure has been completed and surgical antenna 400 is ready to be used to treat the patient.

The complete process involved with calibrating the electrosurgical system developed in this work may be as follows:

1. Connect flexible cable assembly 600 to surgical antenna 400 (alternatively they may be formed in one piece)
2. Sterilise cable/antenna assembly using gamma or steam sterilisation (or other known sterilisation method)
3. Attach calibration load material to distal tip 420 (N.B. calibration load material is preferably biocompatible and sterilised. As mentioned above, this material may be the same as the material used for sterile packaging)
4. Place assembly inside sterile bag or housing
5. Attach proximal end 1011 of cable assembly 600 to output port of generator 1010
6. Send instructions to generator 1010 to initiate the system calibration process via user interface 900 (these instructions may be automatically initiated)
7. Perform calibration to enable radiating tip to be effectively moved to the signal processing unit
8. Remove sterile bag (or housing) and calibration load contained within
9. Surgical antenna 400 is now ready to be inserted inside patient to measure various tissue properties or states and/or to destroy tumours with controlled energy using dynamic impedance matching between the fixed impedance energy source and the tissue, where the mechanism of control is based on the information measured at the distal radiation section (the aerial) 420 of surgical antenna 400.

A further arrangement may use fixed calibration loads that can be screwed onto the end of surgical antenna 400. In a particular embodiment it may be possible to put a thread on the outer wall of surgical antenna 400 and build a calibration load with a tapped hole using a matching thread to enable a good contact to be made between the two parts. The calibration load may be designed using electromagnetic simulation tools to enable the distal radiating section (the aerial) 420 of surgical antenna 400 to see any discrete load between an open circuit and a short circuit impedance (real, imaginary or complex). This concept may be extended further to provide a calibration tool that comprises two threaded screw on loads connected together (possibly back to back) to enable a non-automated two point calibration to be performed. In this instance, it may be desirable to design the calibration loads to enable the radiating tip 420 to see an open and a short circuit impedance. This idea could be further extended to a plurality of such fixed loads by building a 'star' shaped calibration tool that contains a plurality of calibration loads. This concept may have applications where the system is to be used in a non-sterile environment and/or trained operating staff are available to perform the manual calibration routine. Yet another extension to the idea of using the screw arrangement may be to extend the length of the thread of the calibration load and perform the calibration routine during the process of screwing the surgical antenna to the calibration load. Once the two parts are securely connected (or matted) by a couple of turns of the thread, a variation in impedance will be seen by distal radiating tip 420 as the calibration load is further screwed onto the outer shaft of the antenna. When the calibration load is fully screwed onto the radiating tip 420, the antenna will have seen (or will have been subjected to) a plurality of loads to enable a number of calibration points to be measured. It may be preferable to use this arrangement in the opposite direction, i.e. initially screw the calibration load fully onto the shaft of the antenna until the distal radiating tip mates with the end face of the calibration standard and then take a number of calibration points whilst unscrewing the antenna shaft. It may also be possible to place pins or stops within the thread of the calibration load to enable calibration to be performed at a number of fixed calibration impedances. A particular embodiment of this idea may be to use springs to enable the pins to be pushed inside the calibration load to enable the tip of the radiating section 420 to be located, and once the position has been found the pins would be moved out of the region where the tip is located to enable the calibration process to be performed. There may be a plurality of pins located along the thread, each being spring loaded to enable the pins to be moved out of the region where the tip is located prior to measuring the calibration point. This calibration process may require two mechanical or manual adjustments to be made to measure each calibration point, i.e. to push a spring loaded pin corresponding to desired position into the assembly, and to twist antenna (or calibration load) until the new calibration position is reached.

It should be understood from the above that this invention is not limited to using the sliding short (or sliding load)_arrangement, or the other aforementioned means of calibration, for example, unique loads that have been specifically designed for the particular surgical antenna structure, for example, the pen structure (described above) to provide an open circuit and a short circuit to perform the necessary distal tip calibration. It may be possible to use air as the calibration load and/or the packaging material, for example sterile foam, placed around the distal tip of the antenna during packaging, and/or another suitable and stable calibration material. In some instances, it may be possible to use one calibration load only, and this load may be the sterile packaging for the surgical antenna. It may be possible and desirable to perform an additional calibration also at the generator end, for example, using a short circuit connected to the output connector. A particular procedure may be to firstly calibrate the generator to a short circuit termination connected to the output port of the generator, and secondly replace the short circuit termination with the cable and probe assembly and then calibrate again with the distal tip of the surgical antenna loaded with free space or air. In this particular arrangement the short circuit may be replaced with an open circuit or a non-terminated output connector. The particular calibration adopted will be dependent upon the signal to noise ratio of the system and the degree of difference caused by load or material variations of the properties being measured.

The calibration system introduced here can be machined from a solid block of metal, for example, aluminium, brass or copper. Said solid block may also be plated with, for example, silver or gold to provide a low loss environment for the electromagnetic waves to propagate.

It may be preferable for the calibration system to be manufactured using a plastic material, where the surface is coated with a metallic material. It is preferable for the thickness of metallization to be at least several skin depths at the frequency of operation in order to ensure that a high proportion of the electromagnetic field will propagate inside the structure and conduction loss is minimised. For example, if the thickness of metallization is five skin depths then 99% of the electromagnetic energy will propagate. For example, with a frequency of operation of 14.5 GHz and a copper conductor, the required skin depth is 0.506 µm, hence to achieve a layer of thickness equal to five skin depths, the required thickness is 2.530 µm.

It may be desirable to produce a plastic mould or a tool for manufacturing purposes. It may be preferable to split the structure into two sections for ease of manufacture and assembly, and to simplify the metallization process (it should be easier to produce a uniform thickness of metallization with an open structure). In this instance, it would be preferable to split the structure into two equal parts and perform the split along the broad-wall of the waveguide section, where the electric field is zero. The two halves could then be joined together using metallic screws or metallic glue or a combination of the two. In order to ensure that the field leakage along the seam (or join) is minimised, it is desirable to place the screws at one eighth (or one quarter) of a wavelength apart at the frequency of operation to prevent any gaps that are present from acting as radiating slots or aerials. The metallised plastic structure also has the advantage of minimising the weight of the calibration system and reducing the cost of manufacture. Also, the calibration assembly could be split down the middle for manufacture by injection moulding as long as the two parts are carefully fitted together as no currents flow across the centre-line, thus the join does not need to conduct. Given it is envisaged that the calibration system will be a disposable item, these two aspects may offer a significant advantage during the product manufacture phase.

The calibration technique disclosed herein uses a one port reflection detection method. In other words, the measurement that is performed is a reflection measurement, where a signal is sent from a low power microwave source through an antenna to a load and the signal that is reflected back from the load is measured. This measurement is often referred to as a scattering parameter measurement, and the particular measurement performed here is the forward reflection measurement, known as an $S_{11}$ measurement. The dynamic range of reflection measurements is limited by the directivity of the measurement port. To improve the measurement accuracy and sensitivity, it is desirable to conduct a one-port calibration because this can measure and remove three systematic error terms present in one port measurements: directivity, source match, and reflection tracking.

Figure 39:
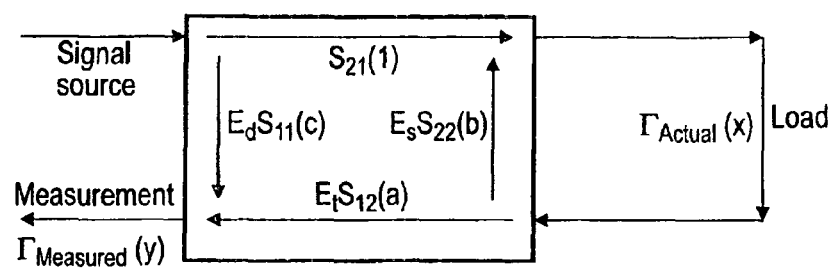
FIG. 39 is a schematic diagram showing typical systematic errors that can occur in one port reflection detection methods.

FIG. 39 is a schematic diagram showing an alternative expression for the relationship between an actual scattering parameter $\Gamma_{Actual}$ and a measurement result $\Gamma_{Measured}$. From the diagram, the following equation can be derived:

$$\Gamma_{Actual} = \frac{\Gamma_{Measured} - E_d}{E_s(\Gamma_{Measured} - E_d) + E_t} \qquad 3$$

where $\Gamma_{Measured}$ is the measured $S_{11}$ value, $\Gamma_{Actual}$ is the actual $S_{11}$ value, $E_d$ is an error from the directivity of the measurement system, $E_t$ is an error from reflection tracking, and $E_s$ is an error from mismatch at the source.

All of the terms in equation 3 may be complex numbers. One way of compensating for the three systematic error terms so that the actual reflection measurements can be derived from measurements taken is to create three equations with three unknowns and solve them simultaneously. This can be achieved using three known calibration standards, e.g. a short circuit, an open circuit and a known load impedance.

An alternative solution is to obtain a mapping function by determining values for three relative error terms ($E_d'$, $E_t'$ and $E_s'$) by comparing $\Gamma_{Measured}$ for three or more calibration standards with known values for those standards measured using a reference probe. Equation 3 can be manipulated to give expressions for the relative errors in terms of the three known and three measured complex impedances.

For subsequent measurements, the mapping function is applied to obtain a complex impedance value for comparison with a stored set of values corresponding to various materials (e.g. biological tissue types) measured using the reference probe.

The mapping function can be more accurate if more than three calibration standards are used.

Figure 40:
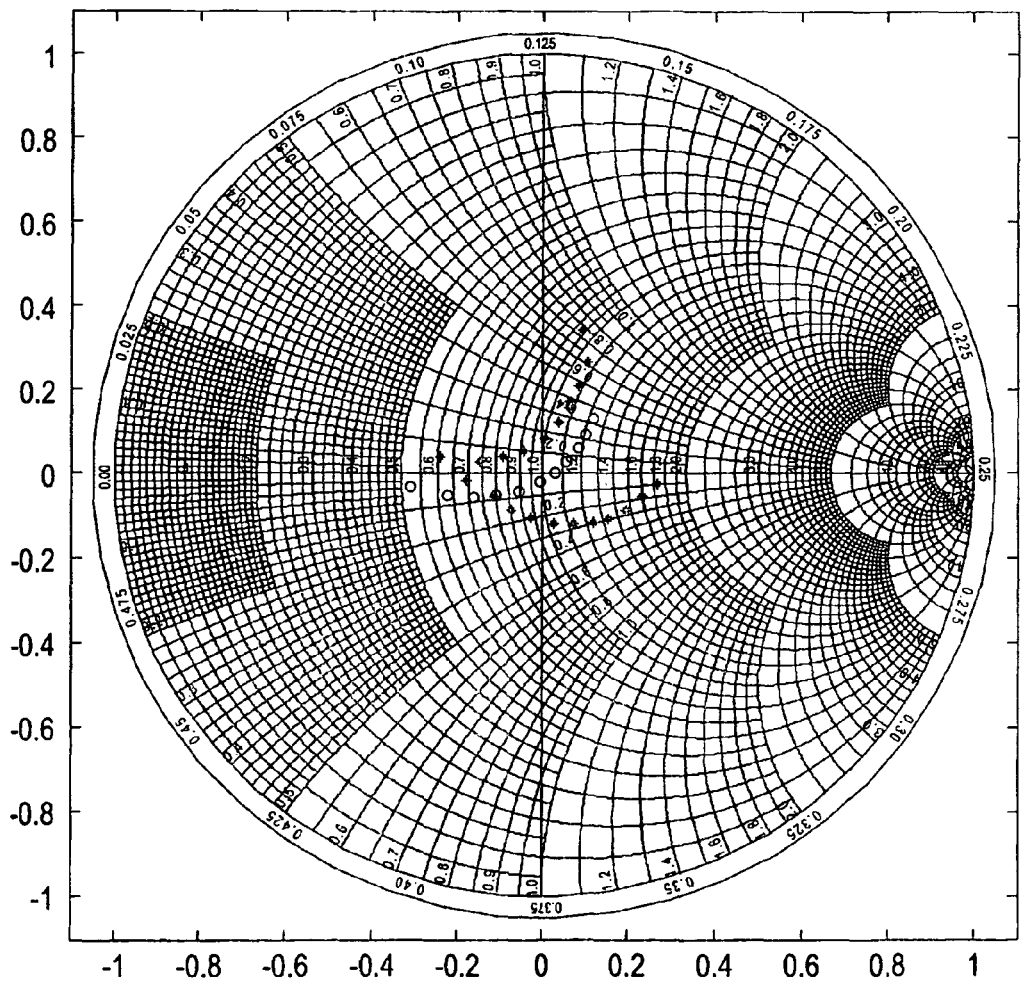
FIG. 40 is a Smith chart having measured impedance values of a set of calibration standards for each of a plurality of probes plotted thereon.
Figure 41:
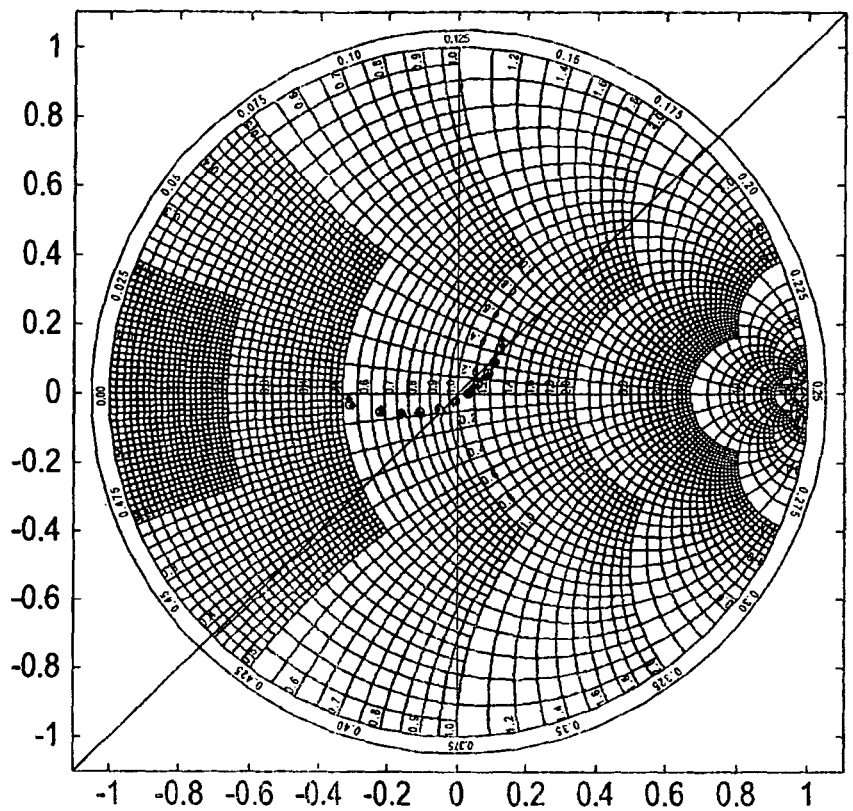
FIG. 41 is a Smith chart showing the measured impedance values plotted in FIG. 40 after phase correction.

FIGS. 40 and 41 are Smith charts with data plotted thereon which demonstrates that the liquid calibration standards discussed below provide very accurate repeatably obtainable complex impedances. There are three sets of eleven data points on each Smith chart. Each set of data points is for a series of eleven calibration standards measured using the same probe. The eleven calibration standards in each series were mixtures of water and methylated spirits (from the same source) in the proportions shown in Table 3.

TABLE 3 composition of calibration standards

| Standard N° | % water | % methylated spirits |
|---|---|---|
| 1 | 0 | 100 |
| 2 | 10 | 90 |
| 3 | 20 | 80 |
| 4 | 30 | 70 |
| 5 | 40 | 60 |
| 6 | 50 | 50 |
| 7 | 60 | 40 |
| 8 | 70 | 30 |
| 9 | 80 | 20 |
| 10 | 90 | 10 |
| 11 | 100 | 0 |

The following procedure was used to prepare the calibration standards:
- two 5 ml Baxa Exacta-Med dispensers were used to separately measure liquid quantity and mix water-methylated spirit concentration samples into a set of test tubes
- as shown in Table 1, the samples were obtained from mixtures of water and methylated spirit. Starting from a 100% (10 ml) water sample, the remaining 10 samples were formed by 10% (1 ml) increments in methylated spirit and 10% (1 ml) decrements in water
- all liquid samples were made to a 10 ml liquid quantity. To ensure the 10 ml liquid quantity was maintained throughout the preparation, measurements were taken at a specific level from the dispensers. This minimises any variations in liquid residuals from the dispensers, thus keeping the concentration mixtures closely to the desired quantity
- all tests were carried out at room temperature
- the prepared standards were kept tightly capped to prevent liquid evaporation and to preserve the concentration content
- the probe was directly connected to a calibrated Agilent 85131F 3.5 mm flexible test port cable which was clamped in a vice to maintain measurement accuracy and to minimise variations in phase and magnitude due to dynamic cable bending
- all complex impedance measurements were made at a spot frequency of 14.5 GHz
- the test tubes holding the liquid concentrations were secured in a fixed position during measurement by clamping the test port cables to a vice to minimise measurement noise
- the probe was inserted into the material at a depth of more than 1 cm and held at the middle of the test tube.

The network analyser and calibration kit used to record and analyse the reflected measurements were an Agilent 8720ET and an Agilent 85052B respectively.

FIG. 40 shows the actual data measured for the three series of calibration standards. FIG. 41 shows the data after phase correction (e.g. to compensate for twisting in the cable and the like which can introduce phase-only errors). The three sets of data sit on top of one another in FIG. 41, which indicates that the calibration standards have consistent and repeatably obtainable complex impedance values.

Figure 42:
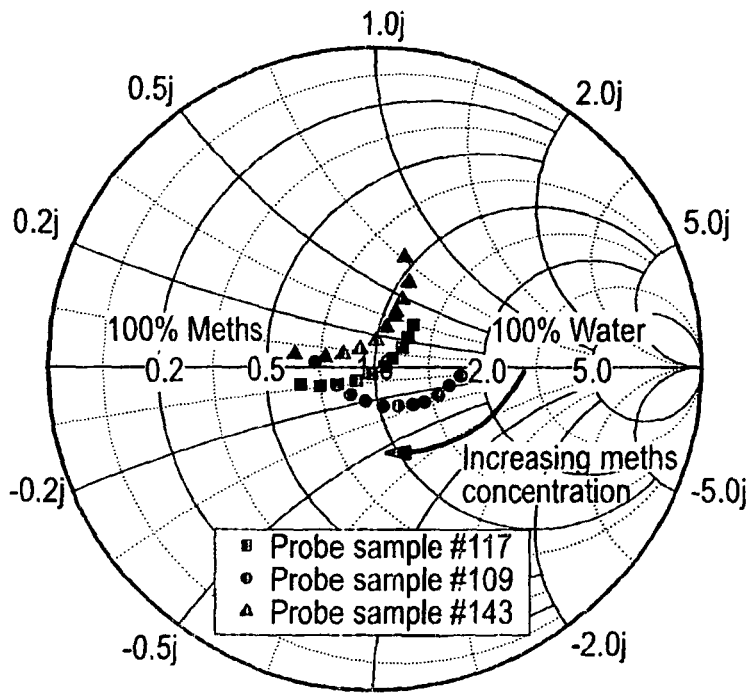
FIG. 42 is a Smith chart having measured impedance values of a set of methylated spirits/water calibration standards for each of a three probes plotted thereon.
Figure 43:
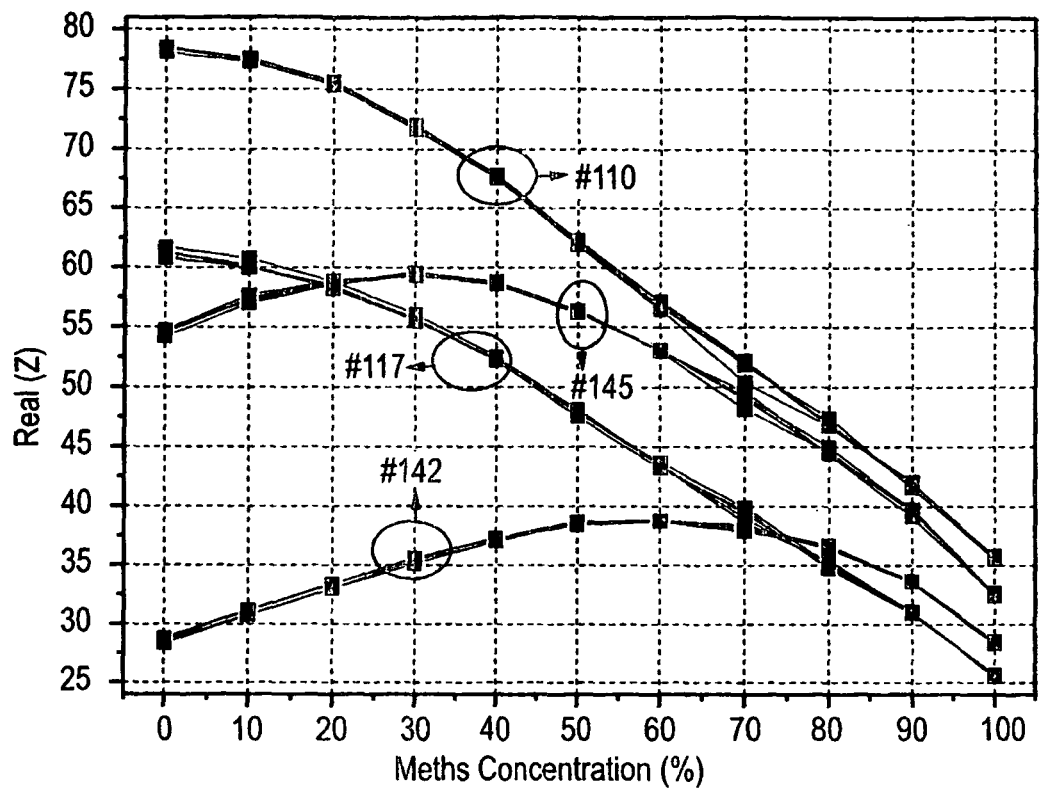
FIG. 43 is a graph showing variation in the real component of the complex impedances plotted in FIG. 42.
Figure 44:
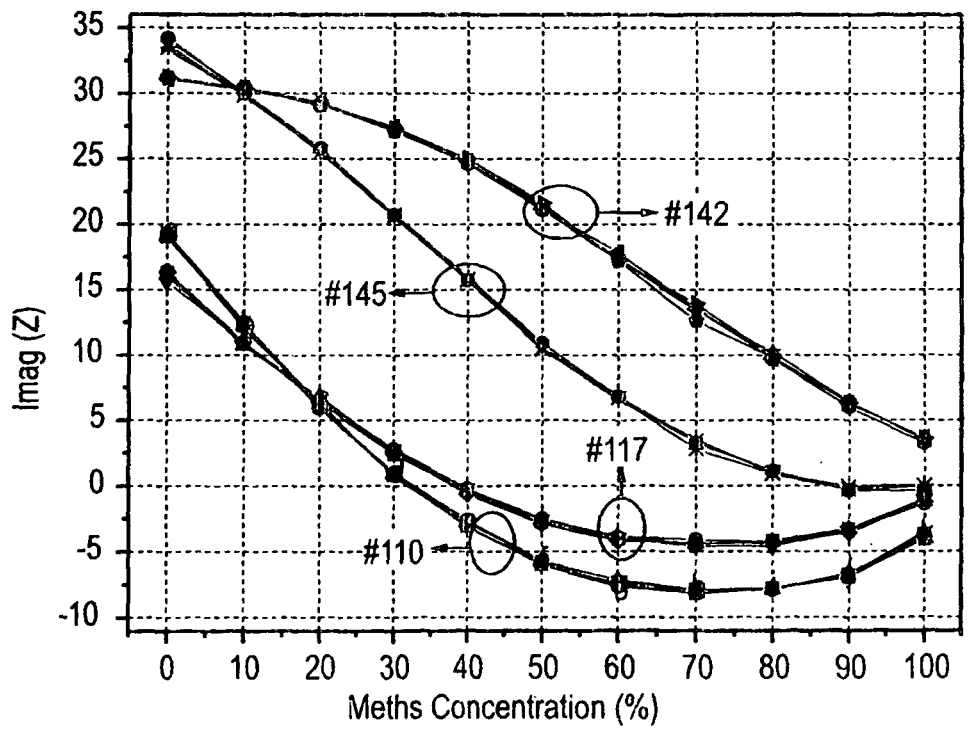
FIG. 44 is a graph showing variation in the imaginary component of the complex impedances plotted in FIG. 42.

FIGS. 42 to 44 are diagrams which demonstrate the repeatable consistency of the calibration standards for three different probes.

FIG. 42 is a Smith chart having plotted thereon the measured complex impedance of the eleven calibration standards discussed above for three probes. Each series of eleven data points has a consistent clockwise distribution. The difference in the clockwise motion of each probe's distribution can be attributed to the manufacturing tolerances in the characteristic impedance for each probe structure. These tolerances can be mathematically corrected, provided the measured impedance distribution motion on the Smith chart is repeatable. The data on this chart show that the calibration standards produce a range of complex impedance values suitable for calibration for different probes.

To asses how well the liquid mixtures are reproduced, measurements using four different probes were repeated five times, each time to a new prepared series of the eleven calibration standards.

The real and imaginary parts of measured complex impedance plotted against liquid concentration for the four probes are shown in FIGS. 43 and 44 respectively. For each probe, the set of eleven data points for each of the five repeated experiments fall substantially along the same line. This show a repeatable impedance change with liquid concentration. The mean standard deviations for the four probes under test (labelled here as probe numbers #110, #117, #142 and #145) are given in Table 4.

TABLE 4 mean standard deviation for four test probes

| | Mean Standard Deviation | |
|---|---|---|
| Probe N° | Real | Imaginary |
| #110 | 0.23 | 0.15 |
| #117 | 0.24 | 0.17 |
| #142 | 0.23 | 0.15 |
| #145 | 0.57 | 0.17 |

As mentioned above, methylated spirits (or denatured alcohol) is a mixture of ethanol (~90%) and methanol (~10%). The composition of this material may change according to the manufacturer or process control. This may have the drawback of causing an unquantifiable variation in the impedance of the calibration standards.

In an alternative embodiment, industrial anhydrous ethanol (i.e. containing 99.9% ethanol) is used to provide a more suitable liquid calibration standard due to its purity. For additional stability and repeatability, the anhydrous ethanol is mixed with deionised water. Deionised water is similar to distilled water. The lack of both ionic and non-ionic organic contaminants in deionised water is deemed bio-medically friendly. Furthermore, it is also less susceptible to corrosive effects. This is a positive feature since the probes may be continuously immersed in liquid during the calibration procedure. By knowing precisely the properties of the mixture, it is possible to reduce errors in the measurement system due to calibration load variations.

Figure 45:
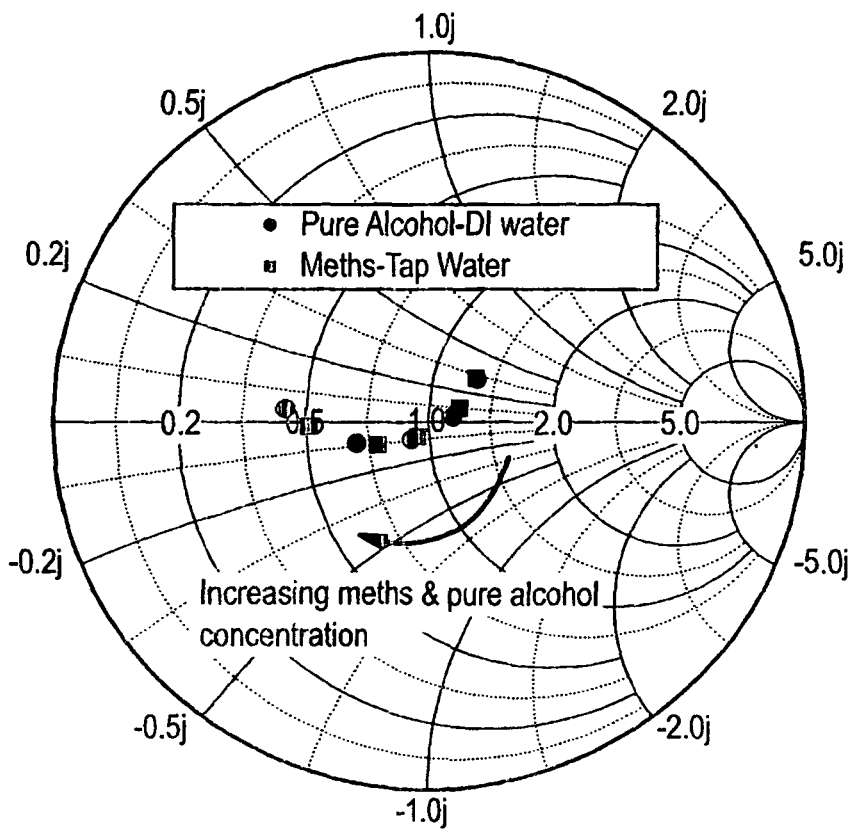
FIG. 45 is a Smith chart having measured impedance values of a set of methylated spirits/water calibration standards and ethanol/deionised water calibration standards taken using the same probe plotted thereon.

FIG. 45 is a Smith chart showing two complex impedance distributions measured using the same probe. Each distribution has five data points corresponding to mixtures of methylated spirits with tap water one the one hand and anhydrous ethanol with deionised water on the other. The anhydrous ethanol used was obtained from Ethimex Ltd, UK.

Both the distributions follow a similar trend, curving in a clockwise manner with increasing methylated spirits or pure ethanol concentration respectively. However, the anhydrous ethanol mixtures offer a wider dynamic range. This is apparently because of differences in the complex impedance of anhydrous ethanol compared with methylated spirits. FIG. 45 shows that the values of the two distributions towards the 100% water end are very similar despite the fact that a lack of ions (impurities) may cause the resistivity of deionised water to increase. It seems from FIG. 45 that the presence of ionic content in deionised water would cause very little variation in impedance. Thus, deionised water may act as a viable alternative to tap water as a calibration standard. Moreover, any change in ionic content of tap water from region to region or country to country may not cause large errors. Nevertheless, using anhydrous ethanol and deionised water can assist in improving the error correction procedure while maintaining calibration accuracy.

Figure 46:
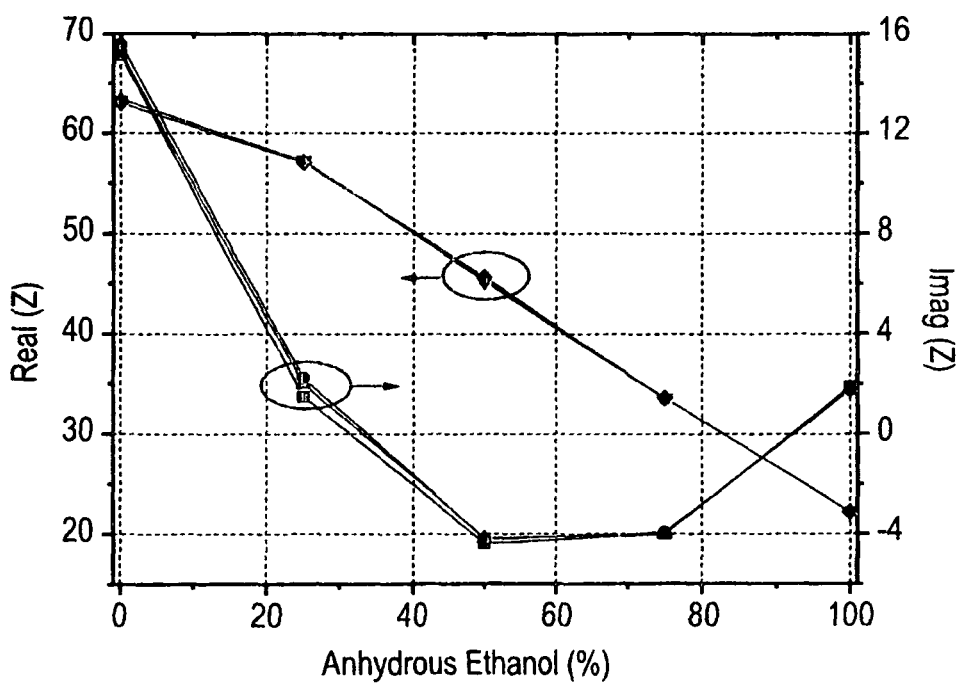
FIG. 46 is a graph showing variation in the real and imaginary components of measured complex impedance values of a set of ethanol/deionised water calibration standards for a probe.

FIG. 46 is a graph which demonstrates the repeatability of deionised water/anhydrous ethanol liquid mixtures. In this case, the same probe was used to measure three sets of five calibration standards. In this embodiment, the calibration standards were each 10 ml having compositions as shown in Table 5.

TABLE 5 composition of calibration standards

| Standard N° | deionised water (ml) | anhydrous ethanol (ml) |
|---|---|---|
| 1 | 0 | 10.0 |
| 2 | 2.5 | 7.5 |
| 3 | 5.0 | 5.0 |
| 4 | 7.5 | 2.5 |
| 5 | 10.0 | 0 |

Deionised water and anhydrous ethanol do not mix as readily as tap water and methylated spirits. However, a consistent (substantially uniform) solution is obtainable by thoroughly mixing the two liquids and then allowing the mixture to settle before taking measurements.

The real and imaginary parts of the measured complex impedance are plotted on the chart shown in FIG. 46 for the three sets of calibration standards. This chart indicates a repeatable impedance change with increasing anhydrous ethanol concentration with a mean standard deviation of 0.12 (real part) and 0.16 (imaginary part).

Figure 47:
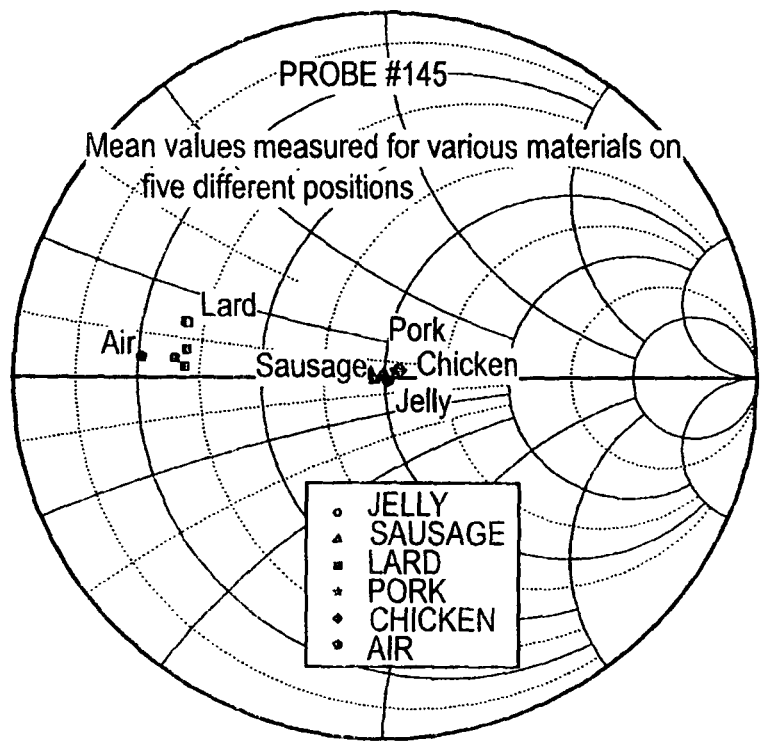
FIG. 47 is a Smith chart having mean values of calibrated complex impedances measured by a probe for different materials plotted thereon.
Figure 48:
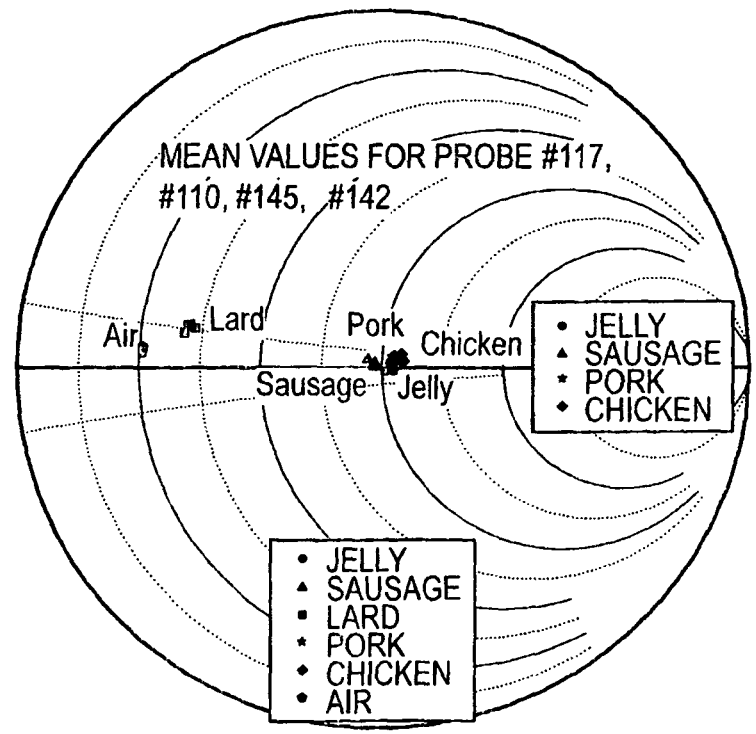
FIG. 48 is a Smith chart having mean values of calibrated complex impedances measured by five different probes for different materials plotted thereon.
Figure 49:
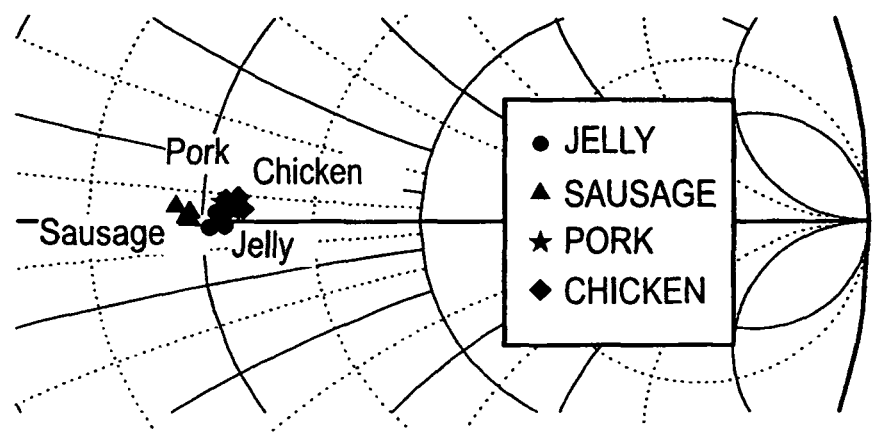
FIG. 49 is a close up view of the centre of the Smith chart shown in FIG. 48.

FIGS. 47 to 49 show how calibration can be used to map measurements of unknown material taken using different probes to a consistent (repeatable) position, which may be usable to identify the unknown material. For example, if calibration is performed using a reference probe, the subsequent mapped measurements may be compared with impedances values for various materials that are predetermined using the reference probe and e.g. stored by the system.

In the following experiment, known tissue types were used. The experiment shows that the mapping function generated using the calibration technique discussed above can map a plurality of measurements taken using different probes to a consistent location, which is then representative of that tissue type.

In this experiment, one probe (number #145) was used as a reference probe. The reference probe was used to measure the complex impedance of various materials in a sample. In the experiment, a layered structure of materials was contained by a jelly-water solution inside a transparent plastic holder. The materials tested were jelly, sausage, lard, pork and chicken. Porcine tissue formed the greatest category as pork most closely resembles human tissue.

FIG. 47 is a Smith chart which shows the measured complex impedance for the materials using probe number #145. The measurement shows consistent complex impedances are obtained when varying the position in the measured materials for air, chicken, pork and jelly. However, the largest inconsistency was recorded in lard followed by the second largest variation in sausage meat.

It is understood that lard is less lossy and this statement is confirmed on the Smith chart shown in FIG. 47, where it can be seen that the impedance of lard is close to that of air, which is also a low loss medium. The inconsistencies for lard were due to its close proximity to the other materials surrounding it in the layered structure, as the impedance measurement becomes sensitive to position of probe tip in the morbid tissue model. Sausage meat on the other hand consists of various other additives and materials which may contribute to the noted uncertainties in the measured impedance values.

Table 6 gives the mean standard deviation values for the real and imaginary parts for the measured complex impedances in morbid tissue model using probe #145.

TABLE 6 mean standard deviation for morbid tissue model using probe number #145.

| | Mean Standard Deviation | |
|---|---|---|
| | Real | Imaginary |
| Air | 0.017 | 0.020 |
| Jelly | 0.33 | 0.21 |
| Sausage meat | 1.45 | 0.76 |
| Lard | 0.44 | 2.19 |
| Pork | 0.23 | 0.25 |
| Chicken | 0.30 | 0.26 |

Three different probes (probe numbers #110, #117, and #142) were calibrated with probe number #145 using the technique described above. In this case, calibration was performed on the system using the methylated spirit and tap water as liquid calibration standards. Three standards were used, having compositions as set out in Table 7.

TABLE 7 composition of calibration standards

| Standard N° | % tap water | % methylated spirits |
|---|---|---|
| 1 | 100 | 100 |
| 2 | 50 | 50 |
| 3 | 0 | 0 |

A mapping function was determined for each of the test probes. Each mapping function acts to map the measured values of the calibration standards for its respective test probe on to values of the corresponding calibration standard measured by the reference probe (here probe #145).

The calibrated probes were then used to take a plurality of complex impedance measurements of the materials in the layered structure discussed above. For each probe, a mean value of the measurements taken for each material was determined and then mapped using the calibration mapping function to an output value which is plotted on the Smith chart shown in FIG. 48.

Thus, FIG. 48 shows the overall mean measured values for the complex impedance of the various tissue types in the layered structure for the three test probes (numbers #110, #117, and #142) and the reference probe (number #145) after a full calibration has been performed using the prepared calibration standards and following error correction using the mapping function.

FIG. 49 is a close-up view of the centre of the Smith chart of FIG. 48, which shows in more detail how focussed the mean values for the probes are after error correction. Table 8 quantifies this by giving the mean standard deviation values for the real and imaginary parts of complex impedance measurements in the morbid tissue model using probe numbers #110, #117, #142 and #145.

TABLE 8 mean standard deviation for morbid tissue model using probe numbers #110, #117, #142 and #145.

| | Mean Standard Deviation | |
|---|---|---|
| | Real | Imaginary |
| Air | 0.14 | 0.27 |
| Jelly | 1.05 | 1.10 |
| Sausage meat | 0.94 | 0.87 |
| Lard | 0.50 | 0.56 |
| Pork | 1.01 | 0.89 |
| Chicken | 1.33 | 1.02 |

Measurement/Ablation System Configuration

The following section discloses enhancements to the system described in WO 2004/047659 which enable small repeatable changes in the phase and magnitude of the signal seen at the distal tip of the surgical antenna to be detected whilst using small amplitude signals in the transmission path. Detecting these changes can prevent the possibility of tissue damage whilst operating the system in the measurement mode. The system described here can be related to the automated calibration idea described above since the distal tip calibration invention may use the sensitive transceiver and the stable frequency source described here.

This section discloses an analysis of the operation of the resonant cavity that is set up between the triple stub tuning filter and the distal tip of the radiating antenna (the aerial). The analysis given here addresses the effects of changing the physical length or the insertion loss of the microwave cable assembly used to connect the output of the tuning filter (triple stub tuner) to the input of the surgical antenna. The ability to use a low loss flexible cable assembly of up to two metres in length (this may be increased if low loss waveguide is used)_ between the generator electronics (tuner) and the surgical antenna may be beneficial in terms of allowing the system to be used in applications where it is necessary to manipulate a small antenna structure in a sensitive region of the biological system in order to measure information or for the effective treatment of fine tissue structures, where collateral damage to healthy tissue structures or adjacent tissue structures is desirably minimised. The added advantage of being able to use the resonant cavity system to dynamically match or deliver a demanded level of energy into a tissue structure under conditions whereby the impedance of the tissue is changing is that the microwave power devices associated with the generation of the required energy to cause effective tissue ablation can be located in a region that is isolated from the treatment antenna. This is particularly advantageous where it is required to ablate large volumes of tissue since the microwave power devices used to generate energy at frequencies associated with the current invention tend to be very inefficient in terms of DC power input to microwave power output (typically between 10% and 15%), therefore, a large amount of DC heat is generated in this process, which leads to the need for large blocks of metal with fins (heatsinks) and fans in order to remove this heat from the junction of the power devices. If the power devices were located close to the treatment antenna then said heatsink and fan arrangement would also be required in this region, thus it would be very difficult to manipulate the surgical antenna or use the system for treating fine tissue_structures.

Preferably, the insertion loss of the flexible cable assembly connected between the filter and the antenna is kept below 2 dB. Appendix A discloses simulation results and mathematics associated with an analysis of the resonant cavity operation carried out in terms of reflection coefficients at either end of the flexible cable assembly and the insertion loss in one transit of the line. The results of the analysis indicate that a loss of up to 2 dB between the tuning filter and the distal end of the surgical antenna can be tolerated. In a practical system, it is expected that the loss will vary from 1.5 dB to 2 dB. The analysis given in Appendix A proves that the use of dynamic tuning offers significant advantage over systems that do not contain a tuning filter. For example, in a particular instance, it is shown that 25.5 Watts of power is delivered to a certain tissue load without the tuning filter, whereas when the tuning filter is deployed this is increased to 47 Watts. Without the ability to operate the system in the manner described in Appendix A, where practical transmission lines (or cable assemblies) are considered, the implementation of the dynamic impedance matching aspect of this work would only be possible where the tuning filter and the means of detecting portions of the changes in phase/magnitude information (H field loop couplers have been used in this work) are connected directly to the treatment antenna. Such an arrangement may make the physical implementation of the treatment system impractical due to the additional bulk and weight caused by the need to include the tuning filter (triple stub tuner or possibly power varactor diode arrangement), the means of adjusting the tuning filter, and additional cabling needed to route signal lines, power supplies and control signals back to the instrumentation electronics contained within the generator hand-piece. Alternatively, the power source can be moved to the hand piece and the dynamic tuning may take place in the hand piece using, for example, power varactor or pin diodes to replace the mechanical tuning stubs.

Figure 24:
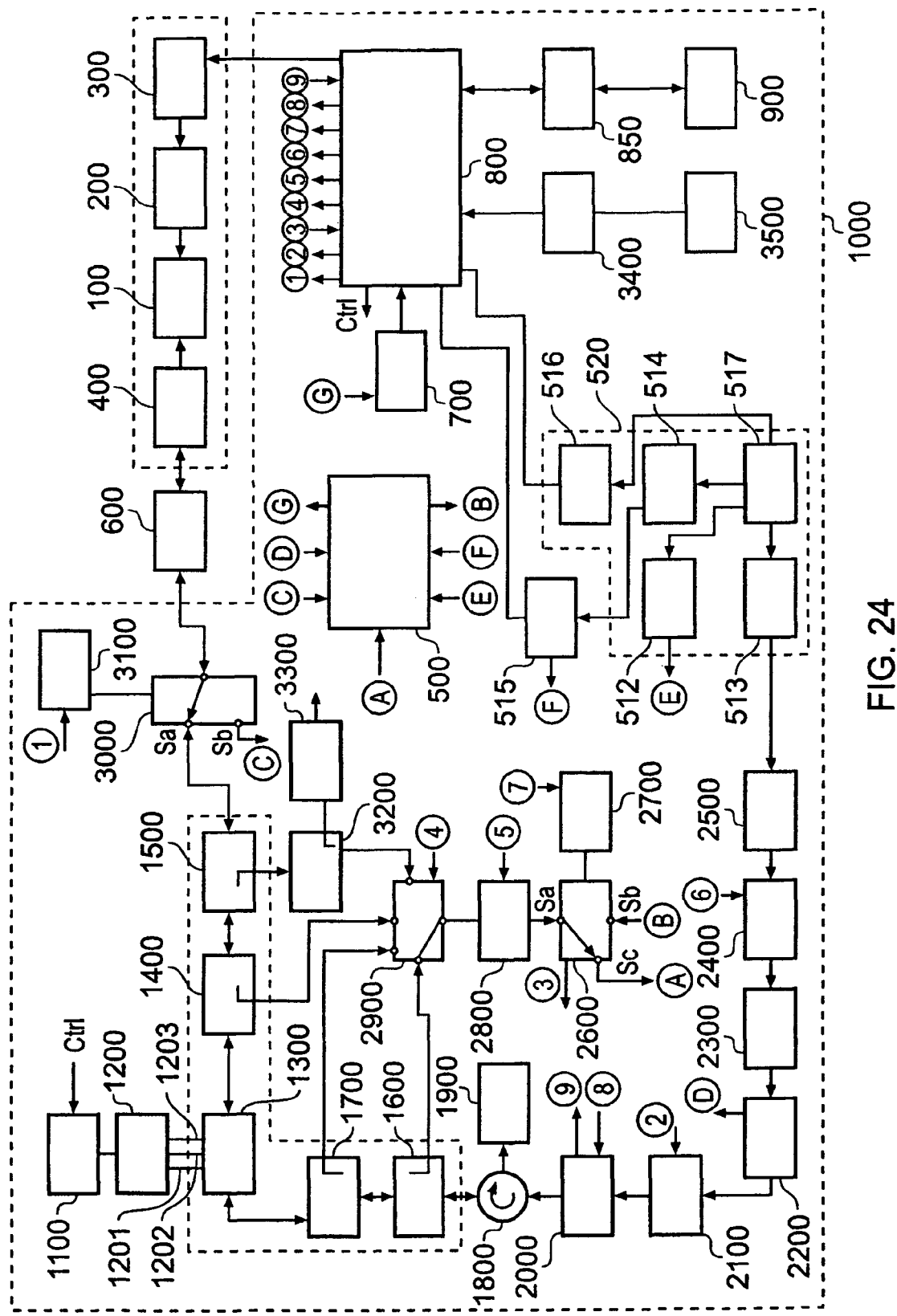
FIG. 24 is a full system diagram for a tissue measurement/ablation system that is another embodiment of the present invention.
Figure 25:
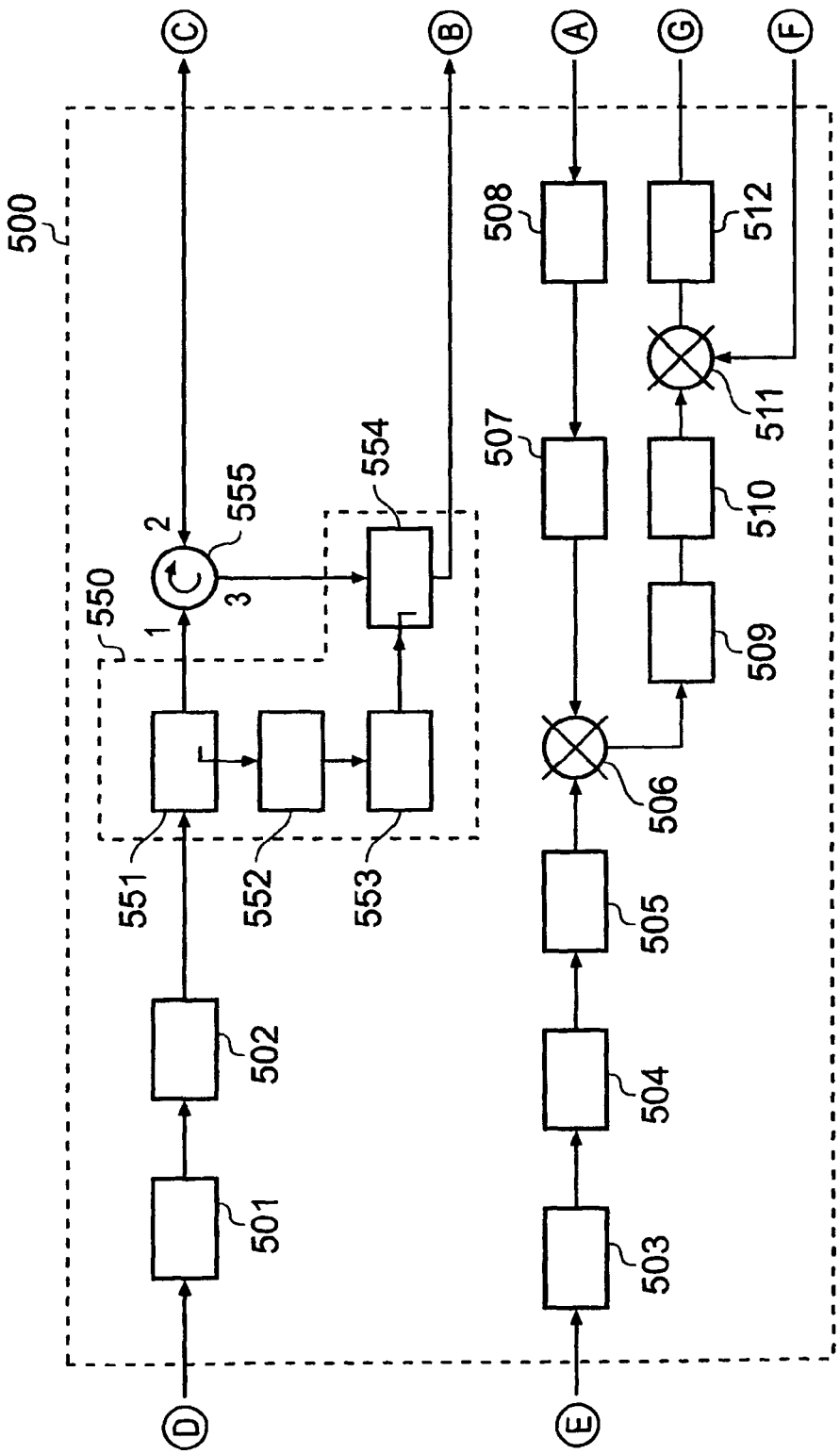
FIG. 25 is a block diagram of the transceiver circuit used in the system of FIG. 24.

FIG. 24 depicts a full schematic system diagram and FIG. 25 shows the new transceiver unit 500 in more detail.

Preferred features of the embodiment disclosed in FIGS. 24 and 25 can be summarised as follows:

1. Treatment channel and measurement channel are separated and connected to single cable assembly using a waveguide switch.

2. A sensitive receiver is used to measure information from the directional couplers in treatment mode.

3. Low power transceiver unit 500 is used to measure tissue state/type information.

4. A phase locked DRO source 513 is used to produce a spot frequency RF signal at 14.5 GHz (+/−1 KHz variation).

5. A phase locked DRO source 512 is used to produce a spot frequency of 14.45 GHz to provide a local oscillator signal for the first frequency down conversion to be performed. The 14.5 GHz RF source 513 and the 14.45 GHz local oscillator 512 share the same temperature compensated 10 MHz reference signal 517.

6. A second frequency down conversion stage is used to produce a final Intermediate frequency (IF) of 10 MHz.

The operation of the two separate channels (treatment and measurement) is as follows:

Channel 1 is used for the treatment mode and uses information measured at the output coupled ports of four directional couplers 1400, 1500, 1600, 1700 to control the position of tuning rods 1201, 1202, 1203 connected to triple stub tuning filter 1300. In this mode of operation the receiver section of transceiver 500 is connected to each of the coupled ports of directional couplers 1400, 1500, 1600, 1700 using PIN switch 2900.

Channel 2 is used for the tissue state measurement mode and in this mode of operation transceiver 500 is connected directly to the proximal end of cable assembly 600, which is attached to surgical antenna 400, which may itself be connected to calibration unit 100 and associated components.

The two modes of operation are separated using a low loss waveguide switch 3000. Due to the need to minimise insertion loss in the cavity formed between the triple stub tuning filter 1300 and the distal tip of surgical antenna 400 (see analysis given in appendix A) it is desirable to minimise the insertion loss caused by inserting waveguide switch 3000 into the system. A further consideration concerning the choice of waveguide switch is that of switching times, i.e. the time during which the mechanical switchover takes place (known as dead time), since during this time neither tissue measurement nor treatment can take place. The advantage of this embodiment is that the sensitive receiver is normally connected to PIN switch 2900 (as shown in FIG. 24) to enable detected forward and reflected power signals incident at the output coupled ports of directional couplers 1400, 1500, 1600, 1700 to permit the necessary measurements to be made that allow dynamic tissue matching to be performed. It may only be required to make sensitive dielectric (or tissue state) measurements before the treatment process to identify the tumour and after the treatment process to check whether the cancerous tissue has been destroyed. During the rest of the time the treatment mode is selected and dynamic tissue matching is operational to enable efficient tumour ablation to occur.

Suitable candidates for waveguide switch 3000 are: AST 75 manufactured and supplied by Advanced Switch Technology (Canada) and WS8189M/00 manufactured and supplied by Sivers Lab AB (Sweden). The characteristics of the two switches considered are summarised in Table 9.

TABLE 9

AST and Sivers Waveguide switches (3000)

| Parameter | AST 75 | Sivers WS8189M/00 |
|---|---|---|
| Frequency range | 10.0 GHz to 15 GHz | 10.0 GHz to 15 GHz |
| Switching time | <100 ms | 100 ms |
| Isolation | 70 dB | 90 dB |
| Power handling (CW) | 2 kW | 2 kW |
| Port matching | −28 dB (return loss) | 1.08 (VSWR) |
| Duty | | 500 ms |
| Switch back time | <200 ms | |
| Insertion loss | <0.05 dB | 0.1 dB |

A particular advantage of using the two channel arrangement shown in FIG. 24 is that sensitive transceiver 500 allows power levels of less than 10 dBm (10 mW) to be transmitted into tissue structures to enable valid tissue type/state recognition measurements to be made. With a single channel arrangement, up to 30 dBm (1 W) of signal power may be required, to perform the same measurement, i.e. up to 30 dBm of power would have to be transmitted into the tissue to achieve the same measurement sensitivity. It is possible to ablate small tissue structures using 30 dBm of CW power, hence having this situation occur during the tissue state measurement process is highly undesirable. The reason that high power levels are used in the single channel measurement/ablation system is due to the fact that the architecture uses 20 dB directional couplers 1400, 1500, 1600, 1700 to extract the information required to make dielectric (or tissue state) measurements, hence the measurement signal is attenuated by 20 dB before it reaches the input to the measurement receiver. This implies that the transmitted signal required to make the same measurement as the system disclosed in the present embodiment must be boosted by 20 dB, i.e. +10 dBm+20 dB=30 dBm (1 W), in order to be able to maintain the same signal level going into the input to the receiver section of transceiver 500.

The ability to measure small changes in phase and magnitude enables small variations of the complex impedance of the tissue load 'connected' to the distal tip of the surgical antenna to be detected. These small changes may be due to a change in the stage of a particular cancerous growth or may be due to the distal tip of the antenna coming in to contact with various tissue structures as the antenna traverses through various anatomical planes, for example, skin, fat, muscle and blood. The transceiver shown in FIG. 25 (discussed below) has a sensitivity that is close to the thermal noise floor, which is around −174 dBm and is defined as the thermal noise power at room temperature (290 K) in a 1 Hz bandwidth. It is in fact the performance obtainable at room temperature if no other signal degradation factors are involved.

The complete system showing the improved topology is shown in FIG. 24. The frequency oscillator unit 520 comprises of five separate oscillators built up into one single module. The 10 MHz crystal oscillator 517, provides the reference signal for the other four oscillators 512, 513, 514, 516 that are used to control the system and enables said oscillator signals to be synchronised with one another. It is preferable for said crystal oscillator 517 to be a temperature compensated crystal oscillator. The other four oscillators contained within frequency oscillator unit 520 are as follows: 14.5 GHz RF source 513, 14.45 GHz local oscillator 512 for first frequency down conversion stage, 40 MHz local oscillator 514 for second frequency down conversion stage, and 50 MHz general oscillator 516 that may be used for timing functions in digital signal processor 800.

The actual embodiment of oscillator unit 520 used in the system was a unit built by Nexyn Corporation (Santa Clara Calif.) and the parameters that are of interest for use in the electrosurgical system described here are listed in Table 10 given below:

TABLE 10

Parameters of stable source oscillator

| Parameter | Value |
|---|---|
| Frequency/power @ Port 1 | 14.50 GHz/>+10 dBm |
| Frequency/power @Port 2 | 14.45 GHz/>+10 dBm |
| Frequency/power @Port 3 | 40 MHz/>+8 dBm |
| Frequency/power @Port 4 | 50 MHz/>+8 dBm |
| Frequency accuracy | <+/−1 kHz over temp and supply voltage |
| Frequency ageing (first year) | <+/−0.3 ppm |
| Frequency ageing (ten years) | <+/−2.5 ppm |
| Discrete spurious (all ports) | <−70 dBc |
| Pulling | 1.5:1 VSWR will not break lock |
| Harmonics | <−20 dBc |

TABLE 10-continued

Parameters of stable source oscillator

| Parameter | Value |
|---|---|
| Phase noise @ 10 kHz | <100 dBc/Hz |
| Operating temperature | 0° C. to 50° C. (baseplate) |
| DC power supply requirements | +15 V +/−0.5 V 1 A steady state, 1.5 A surge |

The output from 14.5 GHz oscillator 513 is fed into the input of DC block 2500, whose function is to prevent switch breakthrough, that may be caused by signals that are sub-harmonic components at the frequency of source oscillator 513 and maybe produced by pulse modulation switch 2400 when switching at a fast rate, for example, less than 10 ns, from getting back into source oscillator 513 and upsetting its operation by, for example, causing frequency pulling, which may result in a shift in the output frequency of source oscillator 513 by an amount that is outside the operation as defined by the specification or requirements for the system (see table 4). DC block 2500 takes the form of two co-axial to waveguide WR75 launchers connected together back-to-back, thus forming a microwave signal environment whereby there is no physical connection between the output from source oscillator 513 and modulation switch 2400. This arrangement creates a band-pass filter to prevent signals outside the frequency range of WR75 waveguide (see table 1) from reaching the input to source oscillator 513. The output from DC block 2500 is fed into the input port of modulation switch 2400, whose function is to enable the RF signal produced by source oscillator 513 to be switched on and off (modulated) at a rate that allows desirable tissue effects to be achieved. The switch position and the switching rate of modulation switch 2400 is determined by a control signal produced by digital signal processor 800; this signal may be a TTL level signal. The ability to deliver microwave energy in a pulsed signal format using modulation switch 2400 enables short duration high amplitude pulses of energy to be delivered into tissue structures and allows various duty cycles and/or custom waveform formats to be developed to achieve the desired clinical effects. In the particular embodiment of the system described here, a S2K2 absorptive single pole two throw switch from Advanced Control Components Inc. was used to implement modulation switch 2400. This particular switch exhibits the following performance parameters: maximum of 3 dB insertion loss, minimum isolation between input and output (poles) when switch is open of 85 dB, maximum time to switch pole positions of 100 ns. The output from modulation switch 2400 is fed into the input of second DC block 2300, whose function is to prevent sub-harmonic (or other) signals produced by the switching action of modulation switch 2400 from reaching the input to power amplifier 2000 and causing the output from power amplifier 2000 to change or to effect the input stage of power amplifier 2000, for example, if a frequency component contained within a switching spike produced by changing the switch position of modulation switch 2400 is within the bandwidth of operation of power amplifier 2000, i.e. at a frequency where said power amplifier 2000 produces gain, then the amplitude of the signal component will be amplified by the gain of power amplifier 2000 at the particular frequency of the signal and will produce additional power at the output of the power amplifier that may cause undesirable tissue effects to occur. DC blocking filters 2500, 2300 used here comprise of two co-axial to waveguide transitions joined together in a back-to-back arrangement to produce a practical embodiment for preventing DC or frequencies below the cut-off frequency of the waveguide of choice (in this case WR75) from propagating, but this invention is not limited to using this particular arrangement, for example, it may be preferable to use waveguide cavity filters, microstrip filters, or co-axial blocks. The filter profiles required for correct operation of blocking filters 2300, 2400 are either low pass or band-pass.

Figure 31:
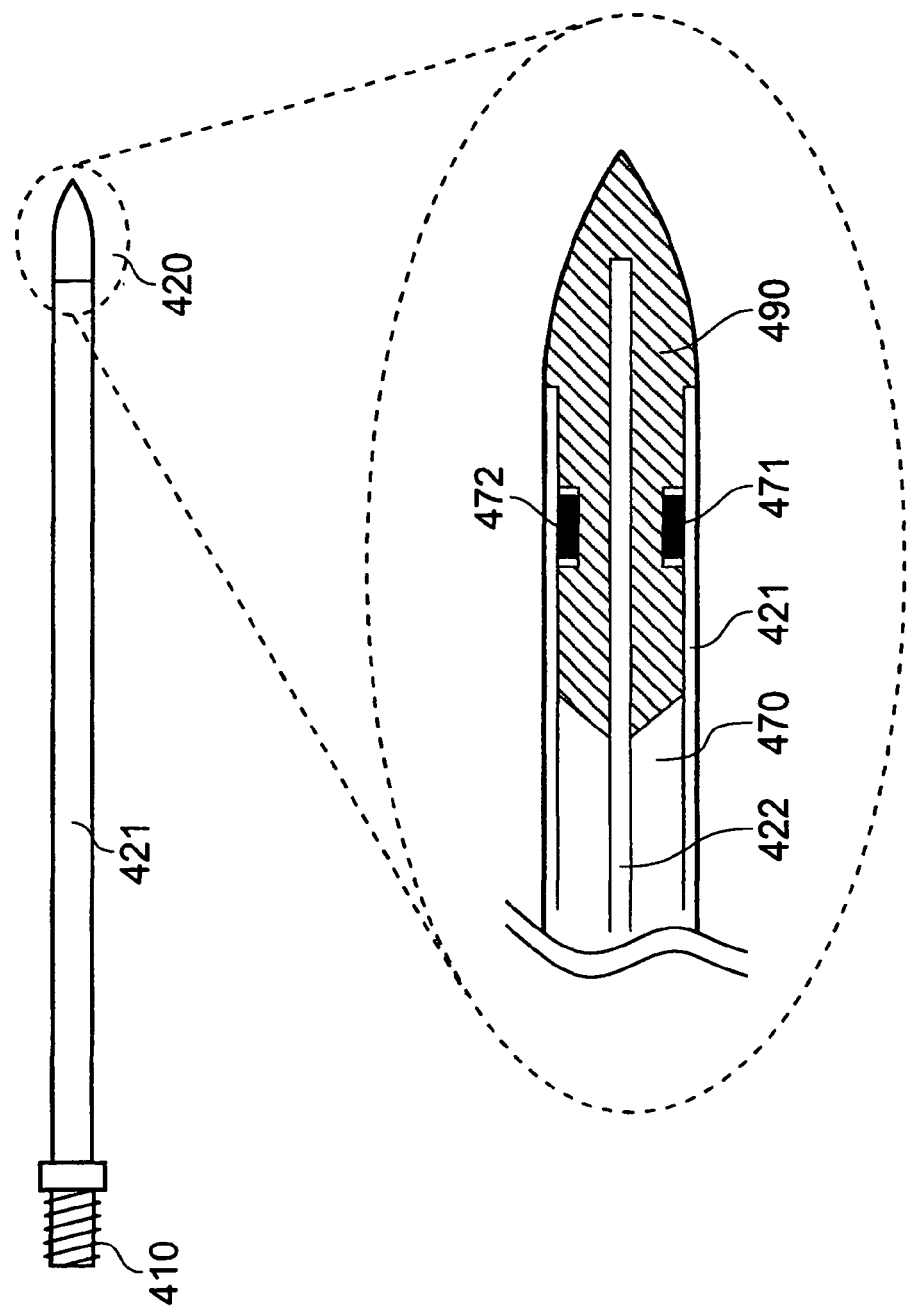
FIG. 31 shows a further antenna suitable for use in the present invention.

The output from second DC block 2300 is fed into the input port of power splitter 2200, whose function is to split the power level at its input into two equal parts, i.e. perform a 3 dB split. Power splitter 2200 is designed to be well matched to the signals connected to the input and the output ports that are contained within a 50Ω environment, i.e. connections are made to the input and output ports using 50Ω SMA connectors connected to semi-rigid co-axial cable assemblies. The first output port from power splitter 2200 connects to the input port of power level controller 2100 and the second output port of power splitter 2100 connects to the input of transceiver 500 (the function of transceiver 500 is described in detail in a separate section given later in this description). The purpose of power level controller 2100 is to control the level of output power delivered at the output of power amplifier 2000 and is, therefore, responsible for controlling the power delivered into tissue structures used to treat various lesions or tumours. The most appropriate devices that could be used for implementing power level controller 2100 for operation at the frequencies of interest in this work are absorptive and reflective PIN diode attenuators. A specific device that is suitable as the power level controller 2100 herein is a 60 dB linearised digital attenuator part number AT-UMCC F00B-HD from Microwave International Ltd. The specification for this particular device is as follows: frequency range 14.4 to 14.6 GHz, VSWR 1.5:1 on all settings, insertion loss (with 0 dB attenuation) 2.6 dB max, 8 bit positive binary TTL control lines, setting time 500 ns maximum, and input power handling 20 dBm CW maximum. The TTL control signals are generated by digital signal processor 800. The output from power level controller 2100 is fed into the input of power amplifier 2000, whose function is to boost the level of the signal provided by power level controller 2100 to a level that can be used to enable surgical antenna 400 to deliver the desired amount of energy to cause ablation of biological tissue in contact with the tip of said surgical antenna 400. The specific device used for implementing power amplifier 2000 in this work is 125 W CW Ku band amplifier unit HPAK2125A-RM from Paradise Datacom Ltd. The specification for this device is as follows: minimum small signal gain 77 dB, gain flatness over band of operation 0.2 dB, 1 dB compressed output power at 14.5 GHz of 50.4 dBm (109.6 W), saturated output power at 14.5 GHz of 50.5 dBm (112.2 W), input return loss 20.5 dB, and output return loss 17.7 dB: Sensors are integrated within power amplifier 2000 to enable the base-plate and power device temperature monitoring, drain and gate-source voltage monitoring, forward power level (amplifier block) monitoring. The unit also accepts input control lines to enable the amplifier to be muted and to allow the power to be controlled using an internal PIN diode attenuator. The sensor signals coming from the amplifier are input into signal processor 800 for subsequent processing. Digital signal processor 800 is also used to control/mute internal attenuator signals. Power circulator 1800 is used to protect the output port of power amplifier 2000 against damage due to reflected energy coming back into the output stage caused by mismatched loads at the distal tip of surgical antenna 400 (or another condition that may cause reflected power at the output of power amplifier 2000, for example, damage to cable assembly 600, cable assembly 600 not being connected, or a setting of tuning stubs 1201, 1202, 1203 that causes a refection to occur at the input of tuning filter 1300). The third port of power circulator 1800 is connected to a 50Ω power dump load 1900 to enable any energy that flows in the reverse direction between ports 2 and 3 to be absorbed. It is desirable for power dump load 1900 to be well matched to the impedance of port 3 of power circulator 1900 to ensure that energy flow between ports 3 and 1 is minimised. Power circulator 1800 should also exhibit high reverse signal direction isolation in order to minimise energy flowing back into the output of power amplifier 2000. In the specific system embodiment developed here, power amplifier 2000 has an internal power circulator (the combination of the circulator and the dump load is often referred to as an isolator) which provides signal isolation at a frequency of 14.5 GHz of 23 dB. Additional circulator 1800 and dump load 1900 shown in FIG. 31 provide an extra 23 dB of isolation, thus the forward and reflected signals are isolated from the output stage of power amplifier 2000 by up to 43 dB, therefore, if, for example, the output power level from power amplifier 2000 is 50 dBm (100 W) and the output port of circulator 1800 was connected to an open circuit or a short circuit load, where the reflection coefficient is +1 or −1 respectively, i.e. all of the output power is reflected back, then the output devices contained within amplifier 2000 would be subjected to a reflected wave of amplitude 50 dBm−46 dBm=4 dBm (2.5 mW), which is negligible. This arrangement caters for the generator being turned on without a cable assembly being attached. The output from power circulator 1800 is fed into the input of tuning filter/coupler unit 530, which is an integrated unit comprising of four directional couplers 1400, 1500, 1600, 1700 triple-stub tuning cavity 1300, and three tuning rods 1201, 1202, 1203. The purpose of tuning filter/coupler unit 530 is to enable the distal tip of surgical antenna 400 (the aerial) to be impedance matched with the 50Ω output impedance of power amplifier 2000 to enable maximum power to be delivered into the complex load impedance of the biological tissue. The impedance of tuning filter comprising of triple stub tuning cavity 1300 and three tuning rods (stubs) 1201, 1202, 1203 may also be adjusted to set up a resonant cavity between tuning filter/coupler unit 530 and the distal tip of surgical antenna 400 in a similar manner to a conventional Fabrey-Perot resonant cavity used in optical systems, whereby multiple reflections are set up within the cavity, to enable a demanded power to be delivered to the distal tip of surgical antenna 400 and into the biological tissue load even under the condition where there is a large mismatch between the 500 generator and the tissue load. The operation of the resonant cavity between the tuning filter 1300 and the surgical antenna 400 (including cable assembly 600) is described in detail in Appendix A given at the end of this description, but the general principle of operation is as follows: the impedance of the triple stub tuning cavity 1300 will be set using tuning rods (stubs) 1201, 1203, 1203 to 'match' the conditions experienced by the distal tip of surgical antenna 400, such that the maximum power is transmitted out of the end of surgical antenna 400 and into surrounding biological tissue. This condition is made possible by reflecting microwave power forwards and backwards along the transmission path (or cavity) between the tuner and the radiating tip of the antenna. For matched conditions, a standing wave may be set up in said transmission line, thus the field in the transmission line (cavity) will be higher than both the incident field from power amplifier 2000 and the desired field to be delivered into the tissue. The magnitude of the field will be determined by the power of the incident wave from power amplifier 2000, transmission line losses, and the degree of mismatch at the distal tip of antenna 400. The transmission line losses will be primarily governed by the insertion loss of cable assembly 600, hence low loss cable assemblies must be used. Other components that add to the transmission loss include: the insertion loss of the co-axial shaft of surgical antenna 400, the insertion loss of waveguide switch 3000 when set-up to enable the system to operate in treatment mode, i.e. a connection is made between output from tuning filter/coupler unit 530 to input to cable assembly 600, insertion loss of tuning filter/coupler unit 530, loss caused by DC break used to form an isolation barrier between the generator (equipment) and the patient (not shown), and the waveguide to co-axial transition at the output of the generator (not shown). The transmission line losses will have an effect on the 'tunability' of the surgical antenna 400, the level of power that can be transmitted into the tissue of the patient, and the amount of stress (voltage and current) that components within the system, for example, SMA connectors and cables, will be subjected to. Appendix A fully describes and analyses the resonant cavity operation described above in terms of reflection coefficients at either end of cable assembly 600, and the loss in one transit of the lumped element transmission line.

The three tuning rods (stubs) 1201, 1202, 1203 inserted through the broad wall of stub tuning cavity 1300 enable all inductive and capacitive impedances to be created. It is possible for the tuning rods to move freely within the cavity whilst maintaining a good short circuit between the outer surface of the tuning rods and the inner wall of the tuning cavity by using three waveguide chokes inside the walls of the waveguide cavity. The design and operation of these chokes is the same for the first choke used in the calibration unit described in detail earlier in this description. The movement of tuning rods 1201, 1202, 1203 inside tuning cavity 1300 is achieved using linear actuators 1200 and appropriate actuator controller units 1100.

The actuators used to move the rods in and out of the tuning cavity could take the form of a linear motor, a moving coil actuator, a piezoelectric device, a stepper motor or a magnetostrictive material based actuator. For the system developed here, it was preferable to use high resolution linear actuators in order to ensure that it was possible to achieve desired length (impedance) adjustment accuracy. The specific linear actuators used in the system disclosed here are LAL20-010-55F devices from SMAC Europe Ltd and the characteristics of interest are shown in Table 11.

TABLE 5

Characteristics of linear actuators used to move tuning stubs

| Parameter | Value |
| --- | --- |
| Linear stroke | 10 mm |
| Movement resolution | 5 μm |
| Rod diameter | 6 mm |
| Force constant | 5 N/Amp |
| Peak force | 7 N @1.3 A (48 V DC) |
| Continuous force | 5 N @ 1 A (48 V DC) |
| DC voltage | 24 V |
| Coil DC resistance | 31 Ω @ 22° C. |
| Coil inductance | 4.12 mH @ 1 KHz |
| Encoder resolution | 5 micron |
| Encoder accuracy | +/−4 counts |
| Operating temperature range | −10° C. to +65° C. |

It is necessary to use three tuning stubs in order to ensure that all regions of the Smith chart can be reached to enable any load impedance to be matched with the 50Ω output impedance of the power amplifier 2000. Actuator controllers 1100 take the form of PID control units, and these units provide the signals required to drive linear actuators 1200 to enable the desired electromechanical conversion to be made to drive tuning rods 1201, 1202, 1203. The input signals to actuator controllers 1100 were provided by digital signal processor 800 and these signals were based on feedback information provided by directional couplers 1400, 1500, 1600, 1700 contained within tuning filter/coupler unit 530. Said directional couplers provide the following information to signal processing unit 800 via time division multiplexing switch 2900, power level adjustment controller 2800, co-axial channel switch 2600, and transceiver 500 to enable appropriate adjustment of tuning rods 1201, 1202, 1203 to be made 1500—reflected power from the distal tip of surgical antenna 400, 1400—forward power from the output of tuning filter/coupler unit 530, 1700—reflected power from the input of tuning filter/coupler unit 530, and 1600—forward power from the output of power amplifier 1800. Reflected power coupler 1500 provides information concerning the reflected signal coming back along cable assembly 600 caused by an impedance mismatch between the distal tip of surgical antenna 400 and the tissue impedance. A further directional coupler 3200 is inserted between the output port from reflected power coupler 1500 and PIN switch 2900 to ensure the power level entering the sensitive receiver section of transceiver 500 is not exceeded. This is achieved by using magnitude detector 3300 to detect the level of power present at the output of reflected power coupler 1500 and using this signal to adjust the attenuation introduced by power level controller 2800 to ensure that the input signal to the receiver contained within transceiver 500 is not saturated. The reason that the signal produced at the output port of reflected power coupler 1500 could exceed the maximum signal acceptable by the receiver is due to high power that may be produced within the resonant cavity for short periods of time due to the resonant cavity action described above (fully addressed in Appendix A), where the signals inside the cavity, of which tuning filter/coupler unit 530 forms an integral part can be injected into the output port of reflected power coupler 1500. The tuning filter/coupler unit 530 used in the system developed in this work was an AM75CD-TUN-MIC3 unit developed by Link Microtek Limited based on the technical specification provided by MicroOncology Ltd. The parameters associated with this unit that are of most importance for use in this work are as follows: insertion loss through unit less than 0.3 dB, coupling factor for all directional couplers 20 dB+/−1 dB, power handling greater than 150 W CW, directivity 26 dB minimum, stub-tuner spacing quarter of the guide wavelength, chokes in guide walls to enable rods to move in and out of the cavity whilst making a good short circuit connection between the tuning rod and the waveguide cavity, and output return loss −26 dB.

The signals from the four output ports of directional couplers 1400, 1500, 1600, 1700 enable the operation of the tuning cavity 1300 to be fully defined and processed information based on the signals from said directional couplers enables the position of the tuning stubs to be moved to create the matched impedance condition, or the resonant cavity condition.

It may be desirable to attach in-line fixed attenuators between the output ports of directional couplers 1400, 1500, 1600, 1700 and the input ports of PIN switch 2900 in order to ensure that the levels of power incident at the inputs to said switch are limited. The power rating of said fixed attenuators must enable power levels generated by the resonant cavity action to be safely absorbed. For example, it may be desirable to use 5 W or 10 W CW rated devices.

The outputs from the four directional couplers 1400, 1500, 1600, 1700 are fed into the input ports of time division multiplexing PIN switch 2900, whose function is to form a microwave signal connection between the output signals at the four directional couplers and the input to the receiver section of transceiver 500 to enable phase and magnitude information relating to the forward and reflected signals, seen at both sides of tuning cavity 1300, to be extracted for the purpose of setting up the correct conditions to enable tissue impedance matching, or the resonant cavity operation to be set-up. The control signals to enable the contacts of PIN switch 2900 to change position (switch polling) are provided by digital signal processor 800. The action of polling all four switches in turn enables changes in phase and magnitude of forward and reflected signals to be measured with respect to one another. The specific embodiment used for time division multiplex switch 2900 was a S4K2 absorptive single pole four throw switch from Advanced Control Components Inc. This device provides the following performance: insertion loss 3.5 dB, isolation 85 dB, and switching speed is less than 100 ns. The single output from PIN switch 2900 is fed into the input of measurement system power level controller 2800, whose function is to adjust the level of power of the signal entering the receiver section of transceiver 500 to prevent the input to said receiver from exceeding an acceptable value or to prevent input saturation. The variation in signal level is due to the large dynamic range of signal levels that may occur when the system is being operated in the treatment modality and also where resonant cavity operation as described in Appendix A occurs, where instantaneous power levels may be much larger than the maximum steady state power level produced by power amplifier 2000. The level of signal attenuation introduced by measurement power level controller 2800 is based on information provided to digital signal processor 800 by magnitude (level) detector 3300. The control signals to measurement power level controller 2800 come from digital signal processor 800 and may be in the form of TTL level signals or another appropriate signal format. The particular device used for the implementation of the measurement power level controller 2800 in this work was a 32 dB linearised digital attenuator UMCC AT-F00B-HD-G1 supplied by Microwave International Ltd. The parameters of particular interest associated with this device are: frequency range 14.4 to 14.6 GHz, VSWR 1.5:1 on all settings, insertion loss with 0 dB attenuation 2.6 dB max, 8-bit positive binary TTL, setting time 500 ns max, and CW input power handling 20 dBm maximum.

The output from measurement power controller 2800 is connected to switch position Sa of co-axial channel switch 2600, whose function is to either connect transceiver 500 to the high power dynamic energy delivery matching/tuning circuit (described above) or to the low power dielectric (tissue impedance) measurement circuit (described below). For operation in the energy delivery mode, common switch contact Sc is connected to contact position Sa, and for tissue impedance measurement mode, common switch contact Sc is connected to contact position Sb, which connects the low power transmitter circuit (described in detail below). Co-axial channel switch 2600 is an electromechanical switch, where the switch position is controlled by current flowing through actuation coils. Coil actuation circuit 2700 provides the drive current required to cause the switch position to change. Coil actuation circuit 2700 is driven by low power signals produced by digital signal processor 800. The low power signals may be TTL level signals or in another appropriate signal format. The control signals for co-axial channel switch 2600 are synchronised to the control signals for waveguide channel select switch 3000.

The operating mode (tumour ablation using dynamic energy delivery matching/tuning circuit or low power dielectric (tissue impedance) measurement) is selected using mode select switch 3000. Mode select switch 3000 and channel select switch 2600 are configured in such a way that they change contact position at the same time; i.e. they are synchronised together. These two switches enable either the controlled ablation or the measurement mode to be selected. Control actuation circuits 3100 and 2700 were developed to enable TTL level control signals from digital signal processor 800 to be used to enable the electromechanical switches 3000, 2600 to be correctly operated.

The position control signal comes from a select line provided by digital signal processor 800. In the first switch position ($S_a$) the system will operate in the controlled ablation mode where only the receiver section of transceiver 500 is used, and in the second position ($S_b$) the system will operate in measurement or tissue recognition mode, where the full transceiver 500 is used, i.e. in this mode both the low power transmitter and the receiver is used.

The output from waveguide channel select switch 3000 is fed into the input to cable assembly 600, whose function is to provide a means of transmitting signals from the generator instrumentation to the distal tip of the surgical antenna and to provide a means of receiving signals from the tip of the surgical antenna, back at the generator instrumentation end of the system. Said cable assembly 600 preferably has a low insertion (or transmission) loss in order to fulfil the requirements associated with the resonant cavity operation described above (and in the detailed analysis given in Appendix A) and to enable as much energy as possible to be available for the treatment of large volume tumours or to be used with resection tools to prevent excessive blood loss during surgery on highly vascularised organs within the human body. Other parameters of interest are flexibility, weight and phase variation with random flexure. The length of the cable assemblies used for the system being developed in this work was 1.5 metres, and the final choice was based on the practical needs of the surgeon and the tolerable transmission loss (as discussed above). The cable assemblies were provided with N-type male connectors at the proximal end and SMA male type connectors at the distal end. During the development of the system described here, a number of microwave cable assemblies were evaluated and tested, but three final assemblies were chosen as candidates for use in the system. Details of the three cable assemblies of choice are given in Table 12 below:

TABLE 6

Low loss cable assemblies usable in the current invention

| Manufacturer | Part number | Insertion loss per 1.5 metres (dB) | Phase variation with random flexure (rms) |
| --- | --- | --- | --- |
| Rosenberger Micro-Coax Ltd | UFB311A | 1.044 | 0.53° |
| Huber & Suhner | Sucoflex 106E 693387 | 0.97 | 1.57° |
| W.L. Gore & Associates Inc. | 8WQ01R010600 | 0.98 | 1.23° |

The values given in Table 12 were measured at a spot frequency of 14.5 GHz using a 50 MHz to 20 GHz 8720ET Agilent vector network analyser.

The output from cable assembly 600 is shown connected to surgical antenna 400 and the other components used for performing distal tip calibration. The components used in the calibration system have been described in detail above. Specific details of surgical antennas that may be used with the current invention are provided below.

Transceiver block 500 is now described in detail by referring to FIGS. 24 and 25. The transceiver 500 uses a microwave circulator 555 to separate the transmitting and receiving signal paths. The principle of operation of the low power transceiver 500 is as follows: a low amplitude and frequency stable 14.5 GHz microwave signal, generated using source oscillator 513 that is referenced to 10 MHz temperature compensated crystal oscillator 517, passes through circulator 1800 from port 1 to port 2 and is transmitted along cable assembly 600 via waveguide switch 3000 through surgical antenna 400 and into either calibration unit 600 (as shown in FIG. 24) or biological tissue structures. A portion of the signal incident at the distal tip of surgical antenna 400 is then be reflected back along the shaft of said needle antenna 400, and cable assembly 600, back into port 2 of circulator 555. The internal path for the signal flowing back into circulator 555 is from port 2 to port 3. The received signal, passing from port 2 to port 3 of circulator 555, is then frequency down converted to provide an analogue signal at a frequency that is suitable for ADC 700 to convert the analogue signal into a digital signal for subsequent signal processing. The transmitter circuit comprises of source oscillator 513, which produces a single frequency at 14.5 GHz with a maximum frequency variation of 1 kHz. Said source oscillator 513 is preferably a dielectric resonator oscillator (DRO) and is phase locked to a temperature compensated crystal reference 517 to provide a single frequency with a small variation around the desired centre frequency, for example, 14.5 GHz with a variation of +/−1 KHz. The output from source oscillator 517 is connected to the input port of first band-pass filter 501, whose function is to pass the signal produced by source oscillator signal 517, but reject all other signals that are present at other frequencies. It is necessary, and indeed highly desirable, for first band-pass filter 501 to block any signals present at the frequency of the first local oscillator 512. It is preferable for any signals that may be present at the frequency of first local oscillator 512 to be attenuated by greater than 40 dB with respect to the signal level produced by source oscillator 517 in order to avoid the signal from first local oscillator 512 degrading the performance of the overall measurement system. The particular embodiment for band-pass filter 501 used in this system was a WB4178 waveguide filter supplied by BSC Filters Ltd. This particular filter exhibits the following characteristics: 4 MHz bandwidth with a centre frequency of 14.5 GHz, 3 dB maximum pass-band insertion loss, 20 dB minimum pass-band return loss, and pass-band signal rejection at +/+50 MHz away from 14.5 GHz of 50 dB. The output from first band-pass filter 501 is connected to the input of fixed attenuator 502, whose function is to attenuate the level of the signal produced by source oscillator 513 and to act as an isolator to help ensure that any reflected signal present at port 1 of microwave circulator 555 cannot get back into the output of source oscillator 513 and effect the operation, for example, cause frequency pulling or output power level variation. The output from fixed attenuator 502 is connected to the input of first directional coupler 551, whose function is to tap off a portion of signal from source oscillator 513 in order to perform carrier cancellation for the received signal (this aspect of the invention is described in detail later in this description when the function of the receiver circuit is addressed). The output from the through path (main signal line) of first coupler 551 (the output port) is passed into port one of microwave circulator 555. Microwave circulator 555 acts as a roundabout for microwave signals, i.e. allows signals to flow in one direction only; the signal paths through microwave circulator 555 are as follows: input on port 1 and output on port 2, input on port 2 and output on port 3, and input on port 3 and output on port 1. Ideally, it should not be possible for any signal to travel from port 1 to port 3, from port 3 to port 2, or from 2 to port 1. Also, path loss or insertion loss from ports 1 to 2, 2 to 3 and 3 to 1 should ideally be zero. In practice, some signal passes from port 1 to port 3, from port 3 to port 2, and from 2 to port 1, and the level of signal is determined by a property known as 'isolation'. For a good circulator, the value of isolation between said ports is as high as possible, for example, an optimised circulator may exhibit isolation of up to 35 dB if narrow bandwidth operation is required. Insertion loss between transmission ports is normally around 0.1 dB for a good circulator that can be operated in the frequency band that is of interest for this work. The output signal from the transmitter stage comes out of circulator 555 at port 2. This signal is then passed down cable assembly 600, through surgical antenna 400 and into calibration unit 100 (or into the biological tissue structure of interest). The level of signal emerging from the distal tip of surgical antenna 400 is such that the biological tissue structure will not be affected or damaged in any way, i.e. the power level will be less than 10 mW (10 dBm) and will most likely will be around 1 mW (0 dBm).

On the receiver side, the signal reflected back along surgical antenna 400, through cable assembly 600 arrives at port 2 of microwave circulator 555, where it travels from port 2 to port 3. The received signal coming out of port 3 goes into the input port of second directional coupler 554. First and second directional couplers 551 and 554 respectively form a part of a carrier cancellation circuit, which is used to increase the level of signal isolation between the transmitted and received signals. The carrier cancellation circuit comprises of first directional coupler 551, a variable phase adjuster 552, a variable attenuator 553, and second directional coupler 554. The operation of the carrier cancellation circuit is as follows: a portion of the forward going signal from stable source oscillator 513, in this case—10 dB (or 10%), from the coupled port of first directional coupler 551 is fed into the input of phase adjuster 552, and the output from phase adjuster 552 is fed into the input of variable attenuator 553. The output from variable attenuator 553 is connected to the coupled port of second directional coupler 554. Second directional coupler 554 is configured such that the received signal from port 3 of microwave circulator 555 passes through the coupler in the 'low loss' path. As already mentioned, the purpose of the carrier cancellation circuit is to increase the isolation between the transmitted and received signals, i.e. reduce the effect of transmitted power at port 1 of circulator 555 getting through to port 3 of circulator 555 via the isolated path from port 1 to port 3. In addition, there will be signals that result from unwanted reflections due to mismatches in the output circuit between port 2 of circulator 555 and surgical antenna 400. The carrier cancellation circuit will also reduce the magnitude of these signals. In the configuration shown, the portion of the forward power from stable source oscillator 513 is adjusted in phase, using phase adjuster 552, and adjusted in magnitude, using attenuation adjuster 553, until the signal injected onto the main line of second directional coupler 554, via the coupled port of second directional coupler 554, is in anti-phase and equal in magnitude to the component of the unwanted transmitted signal coupling into port 3 of circulator 555 from port 1. Once the carrier cancellation circuit 550 has been optimised with cable assembly 600 and surgical antenna 400 fitted, it may be desirable to replace variable attenuator 553 with a fixed value attenuator. If the signal that is coupled into the main-line of second directional coupler 554 is in anti-phase and of the same magnitude as the unwanted signals that are added to the wanted received signal, then the unwanted signals, which will be made up of both the finite isolation across ports 1 and 3 of circulator 555 and the unwanted reflections in the output path, will be removed and the signal seen at the output of second directional coupler 554 will be the wanted received signal only. It is preferable for the coupling factors of first and second directional couplers 551 and 554 respectively to be the same; in this case 10 dB. The use of a stable single frequency transmitter signal is advantageous in terms of allowing circulator 555 to be optimised to increase the breakthrough isolation between ports 1 and 3 of circulator 555 and the single frequency enables only one fixed phase adjustment to be made, and also helps to enable effective cancellation of any reflected signals coming back along the reflected path due to mismatches that may be present along said path. This feature may be used to increase the measurement sensitivity of the overall system.

The particular device used to implement microwave circulator 555 was model SR1414C11 developed by Quest Microwave and supplied by Microwave Marketing.com Ltd. This particular device exhibits the following performance figures: 14.3 GHz to 14.7 GHz frequency range where the following design parameters are guaranteed: 30 dB minimum of isolation between ports where power flow is undesirable, 0.3 dB maximum insertion loss between ports used for forward power flow, and 1.5:1 maximum VSWR. This device was tuned by the manufacturer to provide enhanced performance in terms of port isolation over the frequency range of interest.

Figure 32A:
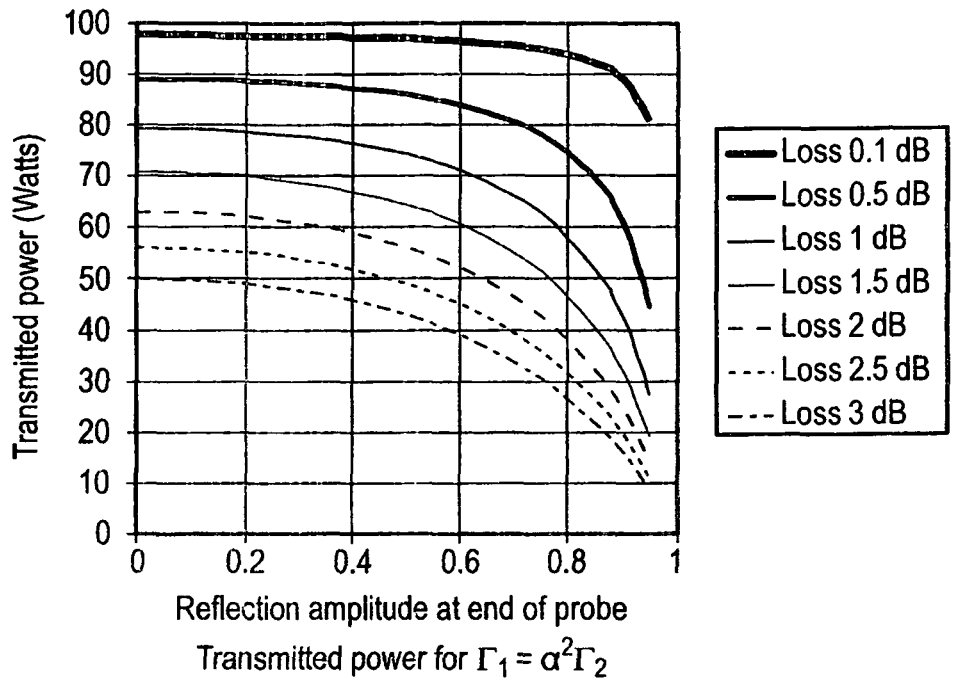
FIGS. 32 to 38 are graphs showing the levels of microwave power that can be delivered for a range of different reflective conditions that may occur at an antenna probe.

The output port of second directional coupler 554 is connected to the input of isolator 508 via co-axial channel switch 2600, whose function is to enable the receiver section of transceiver 500 to be used for making measurements from directional couplers 1400, 1500, 1600, 1700 to enable dynamic impedance matching to be performed, and to also allow for dielectric or tissue state measurements to be made by switching in the low power transmitter stage to complete the transceiver circuit. The function of isolator 508 is to prevent any mismatch or reflection at the input to low noise amplifier 507 from effecting the operation of the carrier cancellation circuit. The output from isolator 508 is connected to the input port of said low noise amplifier 507, whose function is to boost the level of the received signal to a level that is acceptable at the RF input to first frequency mixer 506 to enable said frequency mixer 506 to operate. It is preferable for amplifier 507 to be a low noise amplifier to ensure that the received signal at its input is not corrupted with excessive noise, for example, thermal or short noise produced by the amplifier itself, which will add to the received signal. The particular device used to implement low noise amplifier 507 was model ALN05-0046 developed by Advanced Logging Components and supplied by Link Microtek Limited. This particular device exhibits the following performance figures: 14.5 GHz+/−2 MHz frequency range, 20 dB minimum small signal gain, 2.0 dB typical noise figure, and 14 dBm output power at the 1 dB compression point. The local oscillator input signal to first frequency mixer is a 14.45 GHz signal that is produced by first local oscillator source 512. Said first local oscillator source 512 is preferably a dielectric resonator oscillator (DRO) and is phase locked to a temperature compensated crystal reference 517 to provide a single frequency with a small variation around the desired centre frequency, for example, a 14.45 GHz signal with a variation of less than +/−1 KHz. It is preferable for main stable source oscillator 513 (and measured RF signal) to be synchronised to first local oscillator 512, and this may be achieved by using the same crystal reference 517 (in this case a 10 MHz crystal reference has been used). The output from first local oscillator 512 is connected to the input of signal isolator 503, whose purpose is to prevent any mismatch or reflected signal seen at the input to first driver amplifier 504 from pulling the frequency produced by first local oscillator 512. The output from isolator 503 is connected to the input of said first driver amplifier 504, whose function is to boost the level of the signal produced by first local oscillator 512 to a level that is acceptable by first frequency mixer 506 as a local oscillator signal that will enable said first mixer 506 to operate correctly. The output from driver amplifier 504 is connected to the input of band-pass filter 505, whose function is to pass the signal produced by first local oscillator signal 512, but reject all other signals that are present at other frequencies. It is necessary for band-pass filter 505 to block any signals present at the frequency of the stable source oscillator 513. It is preferable for any signals that may be present at the frequency of the source oscillator 513 to be attenuated by greater than 40 dB with respect to the signal level produced by first local oscillator 512 in order to avoid the signal from source oscillator 513 degrading the performance of the overall measurement system. The particular embodiment for band-pass filter 505 used in this system was a WB4178 waveguide filter supplied by BSC Filters Ltd. This particular filter exhibits the following characteristics: 4 MHz bandwidth with a centre frequency of 14.45 GHz, 3 dB maximum pass-band insertion loss, 20 dB minimum pass-band return loss, and pass-band signal rejection at +/−50 MHz away from 14.5 GHz of 50 dB. The output from band-pass filter 505 is fed into the local oscillator input to first frequency mixer 506. First frequency mixer 506 produces two output frequencies, which are the sum and difference of the RF and local oscillator (LO) frequencies, i.e. RF+LO and RF−LO. In this particular embodiment, 14.5 GHz+14.45 GHz=28.95 GHz, and 14.5 GHz−14.45 GHz=50 MHz. These frequencies are known as intermediate frequencies (IF). The 50 MHz IF is required in this work as this is a usable frequency that can be used to extract magnitude and phase from the measurement signal. The particular embodiment used to implement first frequency mixer 506 for the system addressed in this work was on MQ3531-10 image reject mixer obtained from Microwave Marketing.com Ltd. This device provides the following performance: 10 dB maximum conversion loss, 40 dB minimum LO/RF isolation, 30 dB minimum LO/IF isolation, 14 dBm output power at 1 dB compression point, 16 dBm to 20 dBm local oscillator input power requirement, and 35 dB side band rejection. The output IF from first frequency mixer 506 is fed into the input of fixed attenuator 509 and the output from fixed attenuator 509 is fed into the input of third band-pass filter 510, whose function is to filter out the signal at the sum frequency (RF+LO) and any other undesirable signals that may be present, for example, the components of source oscillator signal 513, the first local oscillator signal 512, the crystal reference signal 517, and the signal going into second local oscillator 511. The band-pass filter shown in the particular embodiment given in FIG. 32 allows the 50 MHz IF signal to pass through the filter unadulterated. The output from third band-pass filter 510 is fed into the RF input to second frequency mixer 511, whose function is to further frequency down-convert the 50 MHz IF signal. The local oscillator input to second frequency mixer 511 comes from second local oscillator source 514 fed via power splitter 515. In this particular instance the frequency of second local oscillator 514 is 40 MHz and it is preferable to use a temperature compensated crystal oscillator or a voltage controlled oscillator (VCO) module for the implementation of this unit. It is preferable for second local oscillator source 514 to be connected to temperature compensated crystal reference to provide a single frequency with a small variation around the desired centre frequency. It is required that main source oscillator 513, first local oscillator 512, and second local oscillator 514 be synchronised together, and this may be achieved by using the same crystal reference 517. The output from second local oscillator 514 is connected to the input of a two way power splitter 515, whose function is to split the power level produced by second local oscillator 514 into two equal parts without causing an impedance mismatch. It may be preferable to use a co-axial 3 dB power splitter to perform this function. The first output from power splitter 515 is fed into the local oscillator input of second frequency mixer 511. Second frequency mixer 511 produces two output frequencies, which are the sum and difference of the RF and local oscillator (LO) frequencies, i.e. RF+LO and RF−LO. In this particular embodiment, 50 MHz+40 MHz=90 MHz, and 50 MHz−40 MHz=10 MHz. The 10 MHz IF is a frequency that can be used by the chosen ADC 700 and fed into digital signal processor unit 800 where it can be used to extract magnitude and phase from the measurement signal. The advantage of using a lower frequency ADC is that greater linearity and dynamic range is normally available. The output IF from second frequency mixer 511 is fed into the input of a band-pass filter 512, whose function is to filter out the signal at sum frequency (RF+LO), in this case 90 MHz, and any other undesirable signals that may be present, for example, the source oscillator signal 513, the first local oscillator signal 512, the crystal reference signal 517, and the second local oscillator signal 514. The band-pass filter shown in the particular embodiment given in FIG. 32 allows the 10 MHz IF signal to pass through the filter unadulterated. The second output from power splitter 515 is fed into the digital signal processor 800 and is used for timing functions and synchronisation of the measurement signals.

An analogue to digital converter (ADC) 700 was used to convert the analogue signal produced at the output of band-pass filter 512 into a digital format that can be processed using digital signal processor 800. Digital signal processor (DSP) 800 is used to perform signal processing functions, for example, calculating phase and magnitude from digital signals provided by ADC 700, and to provide control signals to control the operation of various microwave components within the system (the control signals and requirements for individual components have already been described in detail above). It is preferable to extract phase and magnitude information digitally since the digital processing is noise free, hence the measurement sensitivity is maximised. The signal processing unit used in the system developed in this work was a TMDSEZD2812-OE DSP supplied by Texas Instruments Ltd. Other suitable DSP boards that may suit the requirements for this system include: Analog Devices ADSP21992 Mixed signal DSP controller and Analog Devices BF537 DSP processor. The TMDSEZD2812-OE DSP device has a core speed of greater than 100 MHz, has at least 32 general purpose inputs and outputs available, is capable of being driven by a 40 MHz clock signal, has 64 k words of internal flash ROM, and has 16 k words of internal RAM. It may be preferable for ADC 700 and DSP 800 to be integrated into one single unit. The process of digitally extracting phase and magnitude information is not limited to using a digital signal processor. For example, a single board computer (SBC) with an appropriate input/output (I/O) card may be used.

Single board computer 850 is used to control user interface functions, perform mathematical computation and perform various other functions required for the system to operate correctly. The single board computer used in the system described here was a PCM-9582F-S1A1/5.25" Biscuit PC board with 1.1 GHz Pentium M processor supplied by Hero Electronics Ltd.

User interface 900 provides an interface between the system (equipment) and the user and enables the user to input instructions, for example, treatment requirements, energy delivery settings, size of the_tumour to be ablated, duration of energy delivery, etc. User input 900 also enables treatment information to be displayed, for example, energy delivery profile, net energy being delivered into tissue, tissue structure identification, i.e. fatty tissue, bone, blood etc, and tissue structure information, i.e., cancerous or benign tumour, etc. The user interface may take the form of a touch screen display, a LCD/LED display with a membrane keypad, or a selection of LCD/LED bar graphs with LED indicators and push buttons. A touch screen display was used for the system being developed in this work. A suitable device for this system is a PDC-170-T TFT monitor 17" medical grade high resolution touch screen supplied by Hero Electronics Ltd.

A DC isolation circuit 3400 was developed to provide DC isolation between the footswitch pedal and the user. In the system developed for this work a transformer was used to provide galvanic isolation between the footswitch cable and user. The circuit used two isolated windings on a ferrite core and associated electronic instrumentation. Footswitch pedal 3500 consisted of two normally open switches connected in series and mounted inside an insulated user friendly footswitch pedal enclosure. The system was operated under the control of footswitch pedal 3500 and energy delivery could not be initiated without the two series connected switches contained within footswitch pedal 3500 were closed by the action of physically pressing or operating footswitch pedal 3500.

A typical calibration procedure relating to the electrosurgical system described above may be as follows:

1. With the antenna 400 in place in the calibration unit 100, switch on generator 1010 and activate the calibration procedure via user interface 900. Where the sliding load calibration system is used, it may be preferable for sliding short 125 to be moved to the first short circuit position using electromechanical actuator 200 and then withdraw (or move) the sliding short out of the cavity. The distance traveled should enable the load seen by the distal tip of surgical antenna 400 to change from a short circuit to an open circuit and back to a short circuit again. During movement of the mechanical short, magnitude and phase will be measured using transceiver 500, ADC 700, and Digital Signal Processor/Microprocessor Unit 800 for a number of positions of the sliding short within waveguide cavity 160.

2. The measured points can be used to determine the necessary parameters to calibrate the system (i.e. I/Q gain imbalance calibration and/or DC offset calibration) to enable information seen at the distal tip of surgical antenna to be measured with the effects (noise or errors) introduced by components in the system between the distal tip of the surgical antenna and the digital signal processor cancelled out, therefore, after the error cancellation process has been performed, any measurements taken using the system and subsequently treated using the calibration data will be representative of the load seen at the distal tip of the antenna. The ability to measure a plurality of calibration points enables errors to be minimised, i.e. the more calibration points that can be measured the more any systematic errors that are present will be reduced.

During the calibration procedure described above, DC offset and gain calibration is performed. This calibration procedure relates to ADC unit 700 (this unit may be combined with DSP 800). During this procedure a DC offset calibration coefficient and a gain calibration coefficient is determined. These coefficients are applied to ADC 700 to remove DC offset errors and gain errors to provide the maximum usable range of the ADC. The offset calibration coefficient compensates for DC offset errors in both ADC 700 and the input signal from transceiver 500. The gain calibration coefficient compensates for DC gain errors in both the ADC and the input signal. Increasing the offset coefficient compensates for positive offset, and effectively pushes the ADC transfer function down. Decreasing the offset coefficient compensates for negative offset, and effectively pushes the ADC transfer function up. Increasing the gain coefficient compensates for a smaller analog input signal range and scales the ADC transfer function up, which effectively increases the slope of the transfer function. Decreasing the gain coefficient compensates for a larger analog input signal range and scales the ADC transfer function down, which effectively decreases the slope of the transfer function. An example of this calibration is given in an analog devices technical note, where a certain ADC uses a method where the offset calibration coefficient is divided into ADCOFSH (6 bits) and ADCOFSL (8 bits) and the gain calibration coefficient is divided into ADCGAINH (6 bits) and ADCGAINL (8 bits). The ADC may be calibrated in the factory prior to shipping and the offset and gain calibration coefficients are stored in a hidden area of FLASH/EE memory. Each time the ADC powers up, an internal power-on configuration routine, copies these coefficients into the offset and gain calibration registers in the special function register area.

After calibration, it is possible to define a plane where all complex impedance points that represent various tissue structures (or other load impedances) can be located, and the positions of the points on the plane will be unique to the quantity being measured. The data corresponding to each tissue type may be stored in a look-up table. The data will be gathered using the system described here and the measurements will be made after the unit has been calibrated. Once the complex impedance values have been loaded into look up tables contained within the system, it will be possible to locate the same points using the system once the above calibration procedure has been performed. It may be preferable to use look up tables along with mathematical extrapolation to determine the properties or the type of load connected to the distal tip of the surgical antenna.

Figure 26:
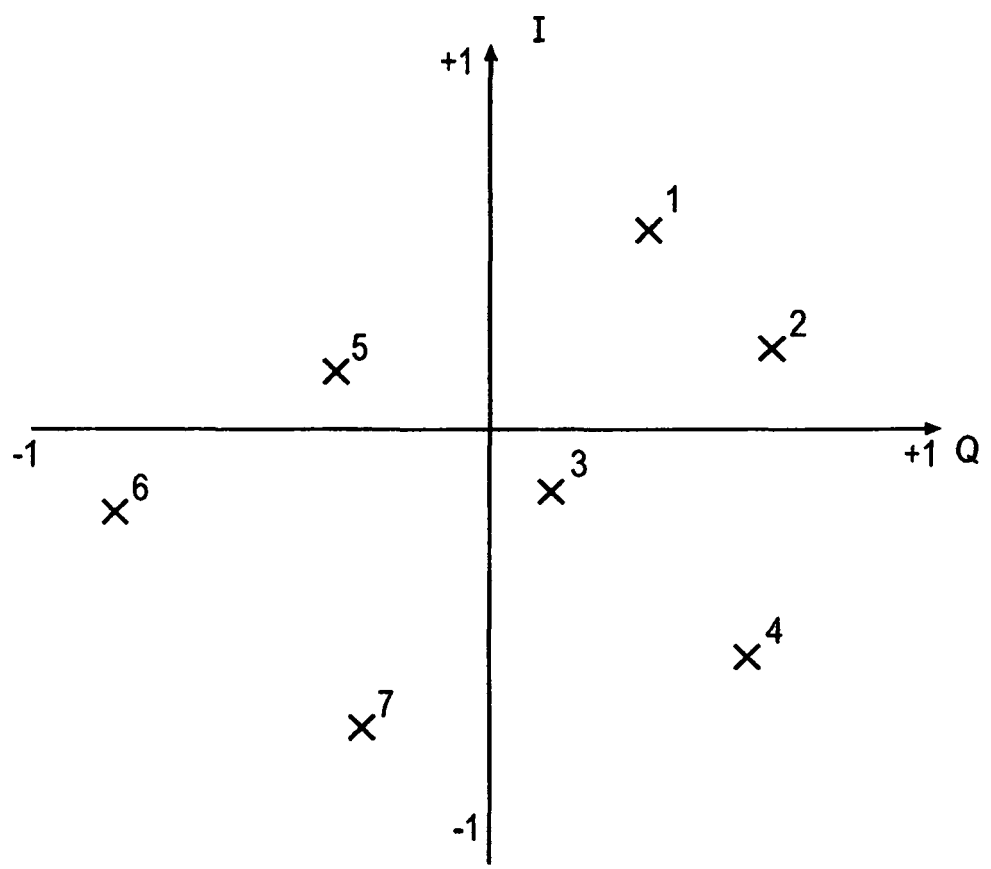
FIG. 26 shows measured information obtained from an antenna after calibration.

FIG. 26 illustrates a representation of seven tissue types using points located on a plane that goes from −1 to +1 in the vertical direction and −1 to +1 in the horizontal direction. It should be understood that once the calibration procedure has been carried out, the seven tissue types will always be defined by the same position on the (−1,1) and (−1,1) plane. In reality these points may represent the stage of the cancerous growth, for example, benign or malignant, or the various biological tissue structures, for example, skin, fat, muscle, blood, bone, etc.

Antenna Structures

The following section provides details of the surgical antenna structures. The surgical antenna structures described here may be calibrated using the procedure described above, e.g. the sliding short (load) calibration unit and means of automatically performing the calibration routine.

Surgical antenna structures that have been considered for this work and described here include: co-axial structures using a plurality of monopole radiating elements housed in a ceramic cone tip with an integral matching transformer, structures using spiral or helical antennas (lines) fabricated onto the surface of ceramic cone tips, inverted balun arrangements, loaded waveguide structures (rectangular, cylindrical, square or any other appropriate geometry), single co-axial monopole and dipole antenna structures, turnstile antenna structures, and single monopole co-axial antennas with integrated matching transformers similar to those described elsewhere for use in a treatment and measurement system associated with the treatment of breast tumours. This invention is not limited to using the surgical antenna structures listed above, and the calibration system described in this work may or may not be used in surgical applications, for example, antenna structures that can be fitted into the calibration unit described here may be developed for measuring the properties of perfumes, detecting hazardous chemicals or materials, measuring the stages associated with the waste processing procedure, or detecting the stages associated with ageing of wines or whisky, etc. This is a non exhaustive list that names some potential applications for this invention.

Figure 27:
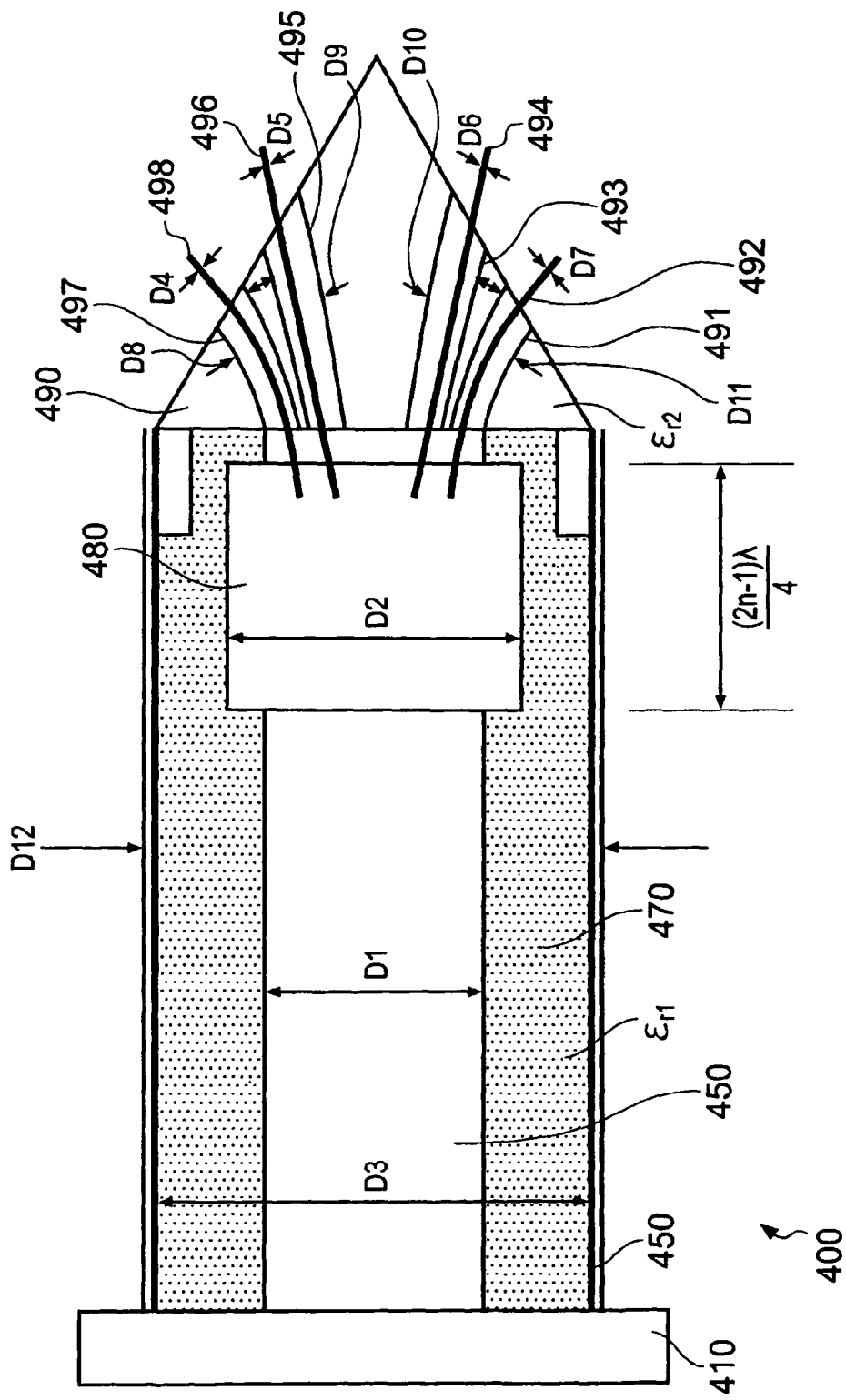
FIG. 27 shows a coaxial antenna with four monopole radiators that is an embodiment of another aspect of the present invention.

FIG. 27 shows a surgical antenna 400 that can be calibrated using the sliding short circuit calibration method described above. The antenna shown in FIG. 27 is a co-axial antenna structure comprising of a first section (410,450,460,470), which is a standard co-axial cable assembly, a second section 480, which is an impedance transformer, and a third section, which comprises of four co-axial lines (491,492), (493,494), (495,496), (497,498) mounted inside a ceramic cone structure 490. The distal ends of said four co-axial lines are preferably coated with a biocompatible material, for example, Parylene C, to prevent tissue or ingress from getting inside the antenna structure. The open co-axial lines are in contact with the biological tissue load and the fields produced by the radiators are used to treat the biological tissue structures. It may be preferable to mount small metallic disks on the ends of centre conductors 492, 494, 496, 498 to change or adjust the field profile. This antenna structure may be used to treat large organs, for example, the liver or the lungs, and may also be used to measure tissue information in terms of tissue state recognition during the treatment process or to determine the tissue structure as the surgical antenna is inserted through various anatomical planes. Ceramic cone 490 preferably uses a low loss dielectric material and this material is preferably a hard material to enable the complete surgical antenna 400 to be inserted percutaneously into the human anatomy.

The surgical antenna 400 is a co-axial structure with an impedance transformer 480 to transform the impedance of a standard co-axial cable to a load impedance made up of the parallel impedance of four further co-axial transmission lines terminated at the distal end with a biological tissue load. The feeding co-axial cable comprises of an inner conductor 460, an outer conductor 450, and a first dielectric ($\in_{r1}$) 470. The feeding co-axial structure is terminated at the proximal end with an SMA connector 410, which enables a connection to be made to flexible cable assembly. It may be preferable for the physical length of said four transmission lines to be an exact multiple of a half the loaded wavelength at the frequency of interest in order to make said transmission lines transparent, i.e. the distal end of impedance transformer 480 will 'see' one fourth of the impedance of the biological tissue 'connected' to the distal end of each of the four transmission lines, assuming that the impedance of the tissue load is the same at each of the four measurement points, i.e. the tissue structure is uniform in terms of impedance.

Impedance transformer 480 is shown in FIG. 27 as an integral part of the co-axial structure. In this arrangement, impedance transformer 480 comprises of a co-axial section whose physical length is an odd multiple of a quarter of the loaded wavelength at the frequency of interest and of an impedance that is equal to the square root of the product of a quarter of the load impedance (assuming that the length of transmission lines (491,492), (493,494), (495,496), (497,498) are an exact multiple of a half the loaded wavelength at the frequency of interest) and the characteristic impedance of feeding co-axial line 450,460,470. If there are no other transformations present in the structure and the characteristic impedance of the co-axial transmission line 450, 460,470 is that of a standard co-axial feed cable, i.e. 50Ω, then the following formula describes the impedance of the first section of antenna structure 400:

$$(138/\sqrt{\in_{r1}})\log_{10} D3/D1 = 50\Omega \qquad 4$$

where $\in_{r1}$ is the relative permittivity of first dielectric material 470 (dimensionless), D3 is the inner diameter of the outer conductor 450 (in metres), and D1 is the outer diameter of the first inner conductor 460 (in metres)

Equation 5, given below, describes the impedance of impedance transformer 480, which is used to match the impedance of the standard co-axial section 450,460,470 with the sum of four parallel impedances of the tissue load and transmission lines (491, 492), (493, 494), (495, 496), (497, 498) [$Z_L$]:

$$(138/\sqrt{\in_{r1}})\log_{10} D3/D2 = \sqrt{(Z_L \times ((138/\sqrt{\in_{r1}})\log_{10} D3/D1))} \qquad 5$$

where D2 is the outer diameter of the second inner conductor 480 (in metres).

The length of the second section (the impedance transformer) is formally described using equation 6 given below:

$$v \times (2n-1)/(4 \times f \times \sqrt{\in_{r1}}) \qquad 6$$

where n is any integer value (dimensionless), v is the speed of light in vacuum or air (3×10⁸ m/s), and f is the frequency of operation (in Hz).

The loss tangent (tan δ) for $\in_{r1}$ is preferably as low as possible to prevent energy from being dissipated in the antenna structure and causing the structure to heat up.

The dielectric constant used for the standard co-axial section can be different from that used for the impedance transformer, but it is preferable to fabricate the structure using the same dielectric material for both sections.

In an alternative arrangement, the outer diameters D1, D2 of inner conductors 460, 480 respectively may be the same, and the relative permittivity of the dielectric material in the region of inner conductor 480 may be changed to provide the necessary impedance transformation.

On the other hand, it may be advantageous to make the diameter D2 large to accommodate the connectivity between the inner conductor of transmission lines (491,492), (493, 494), (495,496), (497,498), i.e. the dimensions D4 (498), D5 (496), D6 (494), D7 (492) within D2 (480).

It should be noted that the dielectric material used for transmission lines 491,492; 493,494; 495,496; 497,498 shown in FIG. 27 is the same as that used for cone tip 490, i.e. $\in_{r2}$.

This arrangement has been used for convenience and ease of manufacture and this invention is not limited to using the same material for the hard cone tip and the dielectric between the inner and outer conductor of the four transmission lines. Furthermore, this invention is not limited to the use of four transmission lines; in theory, any number of transmission lines that can be practically attached to the ceramic cone tip may be used so long as the dimensions of matching transformer 480 are adjusted to ensure that a good impedance match is obtained between the standard co-axial feed structure and the load presented by the biological tissue.

Furthermore, it may be noted that transmission lines 491, 492; 493,494; 495,496; 497,498 may be replaced with single radiating monopole antennas comprising of centre conductors 498, 496, 494, 492 and low loss dielectric cone material 490. This form of antenna may be preferable in terms of enabling the complete surface of cone 490 to effectively act as an omni-directional radiator.

In a practical embodiment, the first section of the antenna structure is a co-axial arrangement comprising of an outer conductor 450 with an outside diameter of 12 mm and an inside diameter of 11 mm, a solid centre (or inner) conductor 460 with an outside diameter of 3.38 mm, and a first dielectric material ($\in_{r1}$) 470 with a relative permittivity (dielectric constant) of 2.0. This co-axial arrangement produces a first transmission line with a characteristic impedance ($Z_{01}$) of 50Ω (using equation 3). The second section of the antenna structure is an impedance transformer, which uses the same dielectric material ($\in_{r1}$) 470, and the same outer conductor 450 as that used in the first co-axial transmission line section, but this time uses a different diameter inner conductor 480. The outer diameter of second inner conductor 480 is 6.1 mm; this produces a section of transmission line with a characteristic impedance ($Z_{02}$) of 25Ω (obtained using equation 3). The physical length of second inner conductor 480 is 10.97 mm, which equates to three quarters of a wavelength at 14.5 GHz, when the structure is loaded with a material that has a dielectric constant of 2.0. The 10.97 mm long section of 25Ω transmission line forms an impedance transformer that can be used to match the 50Ω source impedance (the co-axial input feed line) with a load impedance of 12.5Ω, i.e. $\sqrt{(50\Omega.12.5\Omega)}=25\Omega$. This implies that the parallel impedance of the four transmission lines contained within the ceramic cone 490 must be 12.5Ω if the condition for an impedance matched network is to be satisfied. Ceramic cone 490 is a hard, low loss material that is has a relative permittivity or dielectric constant ($\in_{r2}$) of 10. A suitable material that may be used is a hard ceramic, for example, alumina. The four transmission lines contained within ceramic cone 490 are each made up using two conductors separated with a dielectric material. In this embodiment said dielectric material is the same as that used for the body of the cone tip 490, but this design is not limited to this being the case. In the arrangement shown, the inner diameter of outer conductors 491,493,495, 497 used for the four transmission lines contained within the cone tip is 2.8 mm, and the outer diameter of inner conductors 492,494,496,498 is 0.2 mm. If alumina, with a relative permittivity of 10, is used between the two conductors then the characteristic impedance ($Z_{03}$) of the four transmission lines is 50Ω, thus if the impedance of the biological tissue is also 50Ω, then the impedance seen at the distal end of the impedance transformer is 12.5Ω, i.e. 50Ω/4. Small metal plates are shown attached to centre conductors 492,494,496,498 and these plates may be used to disperse the fields produced by the four radiating transmission lines to produce radiating fields over larger surface areas than that possible if non-terminated elements were used. A small gap exists between the distal end of the impedance transformer and the connection between ceramic cone tip 490 in order to prevent a short circuit being produced between the distal end of 480 and the outer conductors 491,493,495,497. Cone tip 490 is designed to fit inside the co-axial structure.

It may be preferable to remove outer conductors 491,493, 495,497 from the four transmission lines to produce a structure comprising of four monopoles radiating inside ceramic tip 490.

The larger diameter inner conductor 480 used to create the impedance transformer enables the four inner conductors 492, 494, 496, 498 to be physically connected with relative ease.

It may be preferable for the inner conductor used for first section 460 and that used for transformer 480 to be manufactured using a single solid bar or rod. For example, a brass bar with an outer diameter of 6.1 mm may be used and the centre conductor for the first section 460 may be produced by turning the 6.1 mm bar down using a lathe to a diameter of 3.38 mm. A length of 10.97 mm of the 6.1 mm diameter section should be left to perform the required impedance transformation when the bar is assembled inside a conductor 450 filled with dielectric 470.

The antenna structures which protrude from the cone may each consist of an inner and outer conductor separated by a first dielectric material to form a co-axial environment for the waves to propagate, and a second dielectric material used to form a protective cone over said inner conductors. Said protective cones are preferably made from a hard material and may be used to support said inner conductors. The outer body of the antenna is a cylinder and may be a co-axial or waveguide structure. A suitable impedance transformer (or a plurality of impedance transformers) are contained within the antenna structure to enable the co-axial structures to be impedance matched with the antenna feed and the biological tissue load. This type of structure may be used in applications where it is required to ablate large volumes of tissue, for example, within the liver. This structure could be calibrated at the region where the antennas protrude out of cone 490 to enable the structure to be used with the dynamic impedance matching mechanism to enable energy to be efficiently delivered in the instances where load variations occur, for example, during liver treatment when the radiating tips of the antennas become saturated in blood.

Figure 28A:
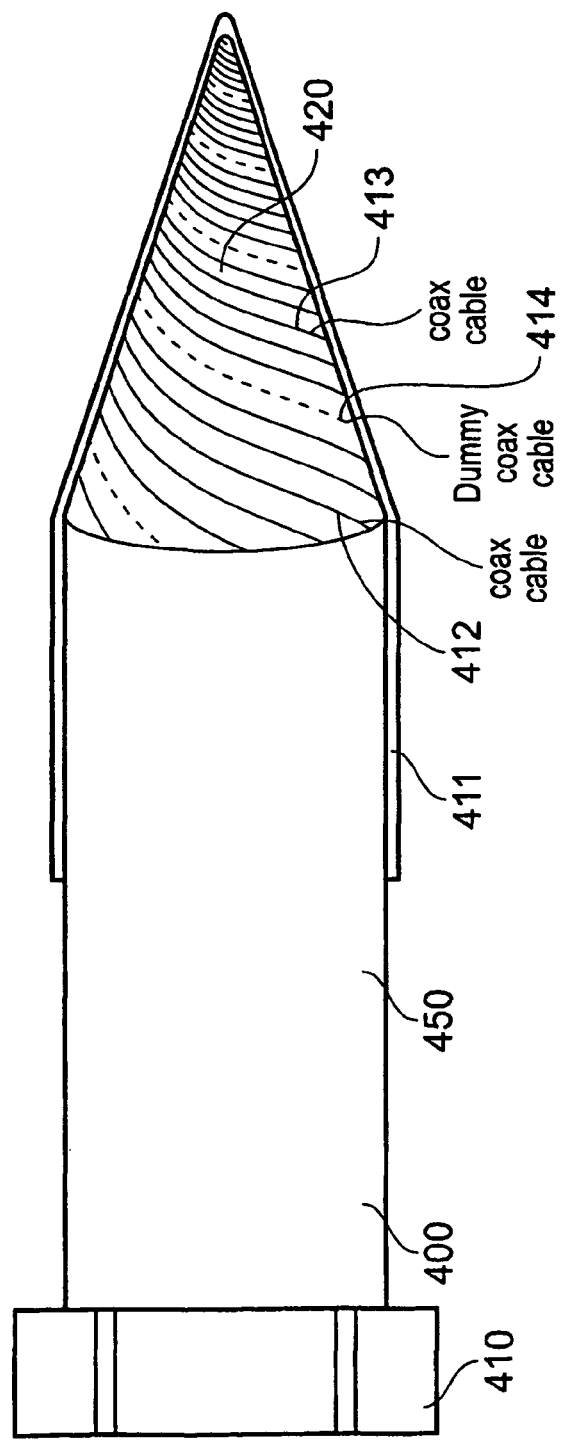
FIG. 28(a) shows a surgical antenna with spiralled metal strips at its distal tip that is another embodiment of the present invention.

FIG. 28(a) shows a spiral antenna structure that has been fabricated onto a ceramic cone. In the arrangement shown here the centre conductor of a co-axial cable is used as the radiating antenna 420 and the return conductor 412 is attached to the outer conductor 450 of the co-axial feed assembly. It may be preferable to fabricate a plurality of radiating elements onto a cone to form the antenna. For example, a turnstile type antenna may be formed where two half wavelength dipole antennas are energised with currents of equal magnitude but in phase quadrature. In order that the currents on the half wavelength dipoles be in phase quadrature, the dipoles may be connected to separate non-resonant lines of unequal length. At the preferred frequency used in this work the unloaded half wavelength is around 10 mm, thus it is feasible to mount a spiral or two dipoles onto a small ceramic (or other) cone to create a radiating antenna structure that can be used for various biological applications. The spiral and turnstile antenna structures described here could be fitted into the calibration assembly described as a specific embodiment of the current invention given in the first part of this document, and the structures could be calibrated to said radiating spiral or turnstile.

Figure 28B:
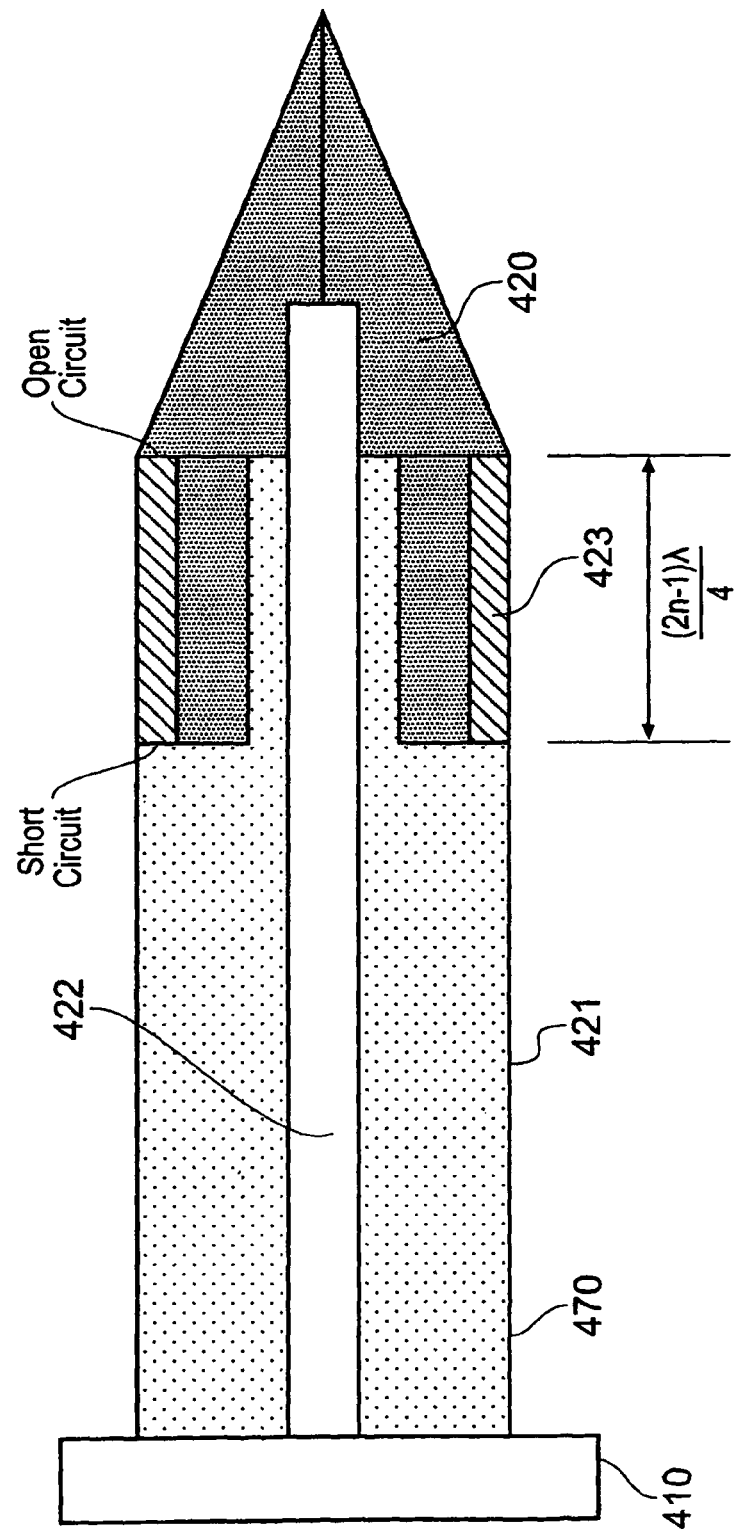
FIG. 28(b) shows an antenna with an inverted balun arrangement that is yet another embodiment of the present invention.

FIG. 28(b) shows a monopole antenna structure where the radiating element is contained within a ceramic cone and a transformer has been included to prevent RF currents from flowing back along the outer jacket of co-axial feed structure 421 and cause the field pattern to change (it has been observed that the radiation produced by the antenna can wrap back onto itself) and produce the undesirable effect of currents flowing along the shaft. The feature of interest here, shown in FIG. 28(b), is the new transformer (often called a 'balun') arrangement that has been developed to make the distal end of conductor 421 'see' an open circuit condition. The shape of cone tip 420 is such that an inverted transformer (or balun) has been formed. This is made possible by making a small groove 423 between the inner wall of outer conductor 421 and the outer section of ceramic cone 420. The length of groove 423 must be an odd multiple of a quarter of the wavelength at the frequency where it is required for no surface currents to flow. All walls of groove 423 must be metallised apart from the wall at the distal end where the edge of the ceramic tip 420 comes into contact with the distal end of outer conductor 421 and the second wall contained within groove 423. The opposite end of the groove must provide a good electrical short circuit in order for the distal end (where the end of ceramic tip 420 comes into contact) to see an open circuit, hence provide the necessary condition for zero current flow. It is preferable for the groove 423 to be filled with air, but a low loss dielectric material may be used to reduce the length of the groove. If a dielectric material is used that is lossy, for example, has a dissipation factor of greater than 0.001 at the frequency of interest, then the balun may become less effective. The balun arrangement introduced here enables an antenna structure to be fabricated that has a continuous profile thus enabling the structure to be inserted inside a patient percutaneuosly to enable minimally invasive procedures to be performed without the risk of burns to healthy tissue or non-desirable energy profiles being produced due to the inclusion of a short circuit to open circuit transformer contained inside the antenna structure at the distal end of the centre conductor. For the treatment of breast tumours, it is preferable for the antenna to be end fined.

A particular advantage of this arrangement is that there is no need to produce a tri-axial structure by attaching a third conductor to outer conductor 421 to produce an open circuit condition at the distal end of outer conductor 421 by using a second co-axial structure where the new outer conductor is short circuited to the new inner conductor 421 at a distance from the end of old outer conductor 421 that is an odd multiple of a quarter of the wavelength at the frequency of interest to produce the desired impedance transformation (balun). If air exists between the two conductors then the length of the balun should be 5 mm at the frequency of interest in this work. It can be seen that the disadvantage of using the conventional balun arrangement is that the diameter of the structure is increased and the structure is a stepped geometry, i.e. the outer conductor and the radiating cone are no longer continuous, hence it would be difficult for an antenna structure using the conventional balun method to be inserted percutaneously inside the human body or to be used in minimally invasive surgery.

The co-axial antenna structure containing an inverted balun described here could be fitted into the calibration assembly described as a specific embodiment of the current invention given in the first part of this document and the antenna structure could be calibrated to the radiating cone aerial.

In another embodiment, the distal end of the centre 422 conductor is not enclosed and so comes into direct contact with biological tissue. Preferably, a low loss, but physically hard material is used to support the inner conductor 422 at the tip and the overall profile of the tip could be such that the antenna structure would lend itself to being used for interstitial treatment where the structure is percutaneously inserted through human tissue structures.

Figure 29:
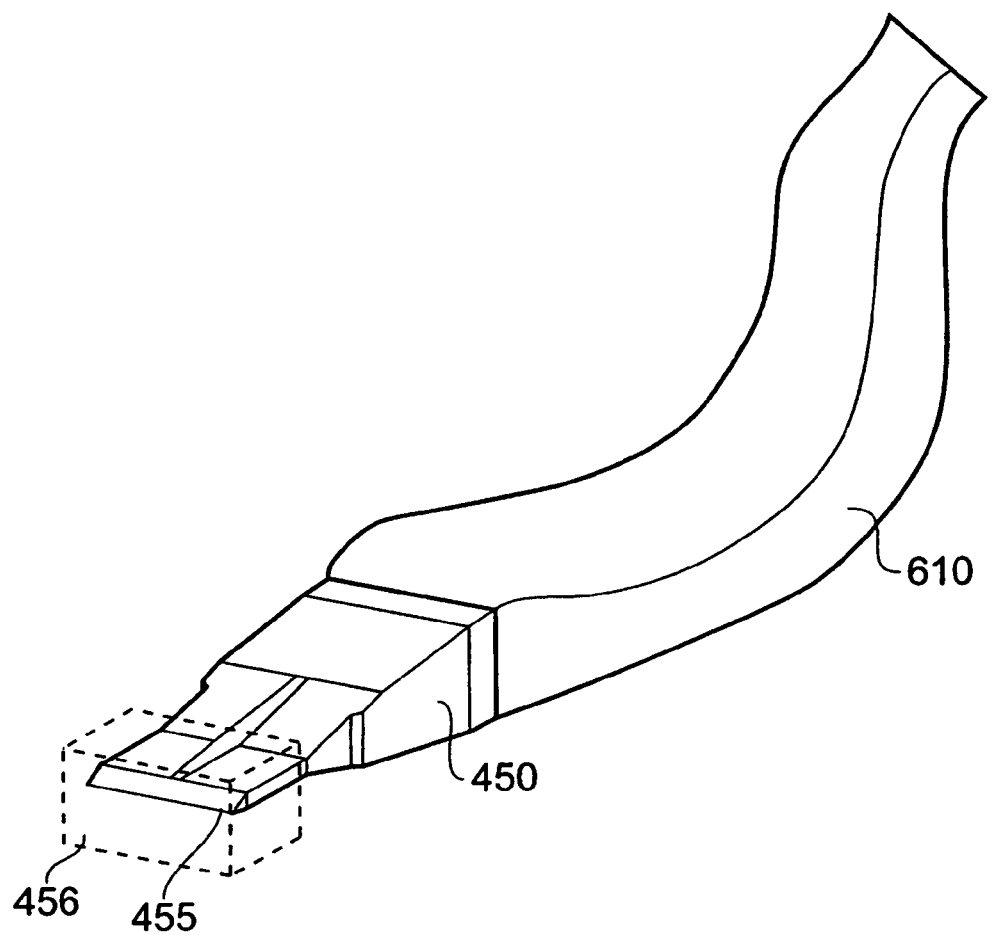
FIG. 29 is a three dimensional view of another antenna that is an embodiment of the invention.

FIG. 29 shows a further surgical antenna structure that can be calibrated at the distal radiating aerial using the calibration method described above. The arrangement shown here is a loaded waveguide antenna, which uses a sapphire material to form the radiating section 455 and, in this particular instance, to also act as a sharp blade that can be used to cut through biological tissue. The structure consists of a length of flexible waveguide 610, a matching transformer 450, and said sapphire blade 455. The sapphire section may be metallised over the surface using an electroforming process with only the end of the blade exposed. The sapphire material may also be used to perform an impedance match between the impedance of the unloaded waveguide section 610, which is a high impedance close to that of air, and the biological tissue, which may be a low impedance, for example, between 100Ω and 1Ω. The size of the waveguide 610 will be dependent upon the frequency of operation. In a particular embodiment for a surgical antenna developed as a part of this work, a section of WG18 (WR 62) flexible waveguide was used that operates over the frequency range of between 12.4 GHz and 18 GHz (see table 1 given above), which was most suitable since the frequency of operation was 14.5 GHz. It may be appropriate to insert tuning screws into the wall of matching transformer 450 to provide a means of statically tuning the antenna to a specific tissue load.

Matching transformer 450 also provides a means of holding the sapphire blade in position and acts as an interface between flexible waveguide 610 and sapphire material 455. FIG. 29 shows sapphire blade 455 in contact with a block of biological tissue 456. One particular application for this surgical antenna is for use in liver resection, where the blade is used to assist with cutting through the liver whilst the microwave energy is used to prevent bleeding by instantly coagulating the blood and also to assist with the cutting process. Blood loss is a particular problem during liver resection using conventional methods, for example, using a scalpel blade. It has been reported that up to 8 pints of blood may be lost during a liver resection procedure, therefore, this invention may be of particular interest for minimising or preventing blood loss during a liver resection procedure or a surgical procedure on other highly vascularised organs within the human body. It could be particularly advantageous to use this antenna with the automated calibration unit disclosed in this work due to the fact that it may be desirable to match into blood and liver tissue.

Figure 30:
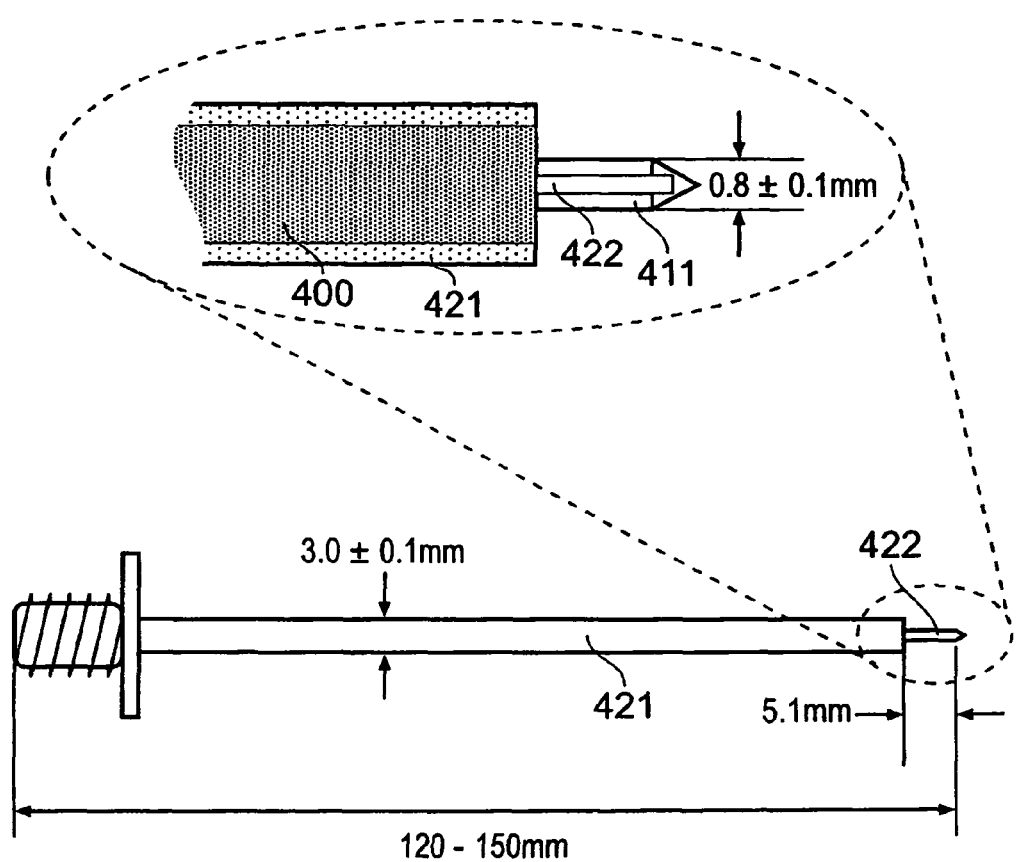
FIG. 30 shows a coaxial monopole antenna suitable for use in the present invention.

FIG. 30 shows a co-axial antenna structure with a stainless steel body 421 and a simple monopole radiating element 422. Said radiating element may be enclosed or encased using a biocompatible material 411 and the material of choice may be a hard material to provide a degree of rigidity for the structure to enable said monopole 422 to be inserted inside a human body unaided. The body of the antenna 400 may be enclosed in a second biocompatible material 421. It may be preferable for biocompatible materials 411 and 421 to be the same material and it may also be preferable for the structure to have a conformal coating of said material. The antenna structure shown in FIG. 40 may be inserted inside calibration unit 100 described in the first section of this document and calibration may take place at radiating monopole 422.

FIG. 31 shows details of a surgical antenna that has been developed to perform ablation of small spherical tumours and to measure information concerning the changing of the state of the tissue during ablation in terms of changes that take place in the impedance of the tissue, and also to measure the impedance of various tissue types as the antenna is being inserted through the tissue structure, and also to differentiate between healthy and cancerous tissue states to locate the position of the tumour to be treated.

The structure shown here consists of a co-axial body 421, a radiating aerial 420, and a microwave connector 410. The co-axial body 421 is preferably rigid to enable the structure to be inserted inside the body percutaneously and unaided. The material used, for the outer jacket of co-axial body 421 is preferably stainless steel and more preferably is a medical grade stainless steel. The inside of the co-axial structure consists of an inner conductor 422 and a first dielectric material 470. The radiating antenna 420 comprises a second dielectric material 490, which is used to provide an impedance match between the co-axial feed structure and the tissue load, and is also used to provide a rigid cone tip to enable the antenna structure to be inserted percutaneously into the human body. The structure also contains a second matching transformer or stub 471 which is a metal ring that sits inside a recess 472, which is machined or moulded inside transformer/tip 490. The function of stub 471 is to help provide a good impedance match between the radiating section of the antenna structure (the aerial) and the tissue load, for example, the stub may produce a small inductance at the frequency of interest that may be used to cancel out a capacitive reactance that may be present when the antenna is inserted inside a tumour. The material used for second dielectric 490 should be a low loss microwave material and is preferably a hard ceramic material. A specific material that may be used is Alumina with a relative permittivity of around 10. This antenna structure can fit inside the calibration unit described in detail above. The antenna structure may be calibrated using the calibration unit to enable the antenna to be used as a measurement device, where it is required to identify various types or states of biological tissue structures and/or to controllably ablate tissue structures using dynamic impedance matching, where the impedance of the tissue being treated is constantly monitored and adjustments are made to a tuning filter to enable the distal tip of the antenna (the aerial) to be impedance matched with the changing tissue load impedance in order to efficiently deliver energy into the tissue to cause fast and efficient tissue ablation.

It is desirable for the surgical antenna structures described above to be made from materials that have no magnetic components. It is also preferable to apply a conformal coating of Parylene C material to the surgical antenna structures described here. A coating thickness of around 10 µm will not affect the microwave behaviour of the structure but will reduce the coefficient of friction on the surface of the antenna. Parylene C is easy to apply and is a biocompatible material that has undergone extensive material tests concerning its use inside the human body. Should the tip of the surgical antenna be made from a non-biocompatible material, i.e. a hard ceramic that is non-biocompatible, then the inclusion of a layer (or coating) of Parylene C may enable the structure to be acceptable for use inside the human body.

APPENDIX

Operation of Surgical Antenna and Triple Stub Tuner Connected at Opposite Ends of a Transmission Line with Losses In this analysis a "probe" corresponds, to the "surgical antenna" or "antenna" described above.

A preferred function of the measurement and ablation system disclosed herein is to deliver microwave power to tumours within a patient. This is to be carried out by inserting into the tumour a 'probe' from which the microwave radiation will be emitted. The probe will constitute an omni-directional aerial that will be in contact with, and be surrounded by, human tissue. It is known that different tissue types have different electrical properties and that these will present a range of electrical impedances to the probe. A consequence of this is that generally optimum power delivery from the generator to the tissue will not occur. This situation is further exacerbated as it is expected that the electrical properties of the tumour will change during ablation, that is while microwave power is being delivered, and so the tissue impedance and efficiency of the process will correspondingly alter during this period.

To obviate the situation described above the system will carry out dynamic tuning of the probe that will be appropriate to the changing electrical conditions presented to the probe. This is to be accomplished using a 'three stub waveguide tuner'. This tuner will be capable of creating all inductive and capacitive impedances, and it will be located within the main equipment. The probe will be situated at the distal end of a cable, and the opposite end of this cable will be connected to a circuit that leads to the tuner.

The impedance of the tuner will be set to 'match' the conditions experienced at the probe, such that a maximum power is transmitted out of the probe and into the surrounding tissue. This process will involve microwave power reflecting 'back and forth', i.e. in both directions, between the probe and the tuner. For matched conditions, a standing wave may be set up in the cable, the field being higher than both the incident field from the generator and that of the field transmitted into the tissue. The magnitude of this field will be determined by both the power of the incident wave and the losses in the transmission line, and also by the degree of mismatch of the probe. The higher this mismatch together with a correspondingly higher mismatch set at the tuner, then the greater will be the multiple reflections between the two and the larger will be the standing wave.

The cable will form part of a transmission line. In addition to the cable, other microwave components will be included in this line between the tuner and the probe, these primarily being a waveguide switch, waveguide directional couplers, a waveguide DC break, a waveguide to coaxial transition and coaxial connectors. It is important to assess the effect that these components will have on the 'tunability' of the probe, and the power that can be transmitted to the tissue of the patient. It is also important to determine whether the magnitude of the standing wave can have any effect on the choice or design of those circuit components that comprise this transmission line.

The problem can be simply described and analysed in terms of the reflection coefficients at either end of a transmission line, and the loss in one transit of the line. In the next section the mathematics of this description will be shown to give simple solutions that are easily calculated through the use of a spreadsheet. This is followed by a discussion and description of some of the conclusions that may be drawn from the analysis.

In this description the voltage reflection coefficient at the probe is $\Gamma_2$, the voltage reflection coefficient at the tuner is $\Gamma_1$, and the one way voltage loss coefficient between the tuner and the probe, including any loss within the tuner, is $\alpha$. $T_1$ and $T_2$ are the corresponding voltage transmission coefficients.

It is assumed that the tuner will be adjusted to give the best phase for the required effect, and so the phase has not been included in the voltage coefficients. The power loss coefficients can be obtained by taking the square of the voltage coefficients. This assumes that all the transmission lines have the same impedance. Similar calculations could be carried out if the lines have different impedances, but with more complicated equations.

In an ideal system there would be no reflections, no loss and perfect transmission. In this case $\Gamma_1$ and $\Gamma_2$ would be zero and $T_1$, $T_2$ and a would be 1. All these coefficients are in the range 0 to 1.

A transmission line has a voltage reflection coefficient from the far end $\Gamma_2$. A whole number of half wavelengths towards the transmitter, along a transmission line of power attenuation $\alpha^2$ there is a discontinuity with voltage reflection coefficient $\Gamma_1$. It will be assumed that the two reflections add either in-phase or out-of-phase, depending on their relative signs.

For a single pass, the transmission through the first discontinuity will be $T_1 = \sqrt{1-\Gamma_1^2}$ (by conservation of power, assuming the impedance stays the same). The reflection from the second discontinuity will be $T_1 \alpha \Gamma_2$. This will be transmitted back along the transmission line and past the first discontinuity with strength $T_1 \alpha T_1 \alpha \Gamma_2$, and also reflected back towards the second discontinuity to reach it with strength $-\Gamma_1 \alpha^2 T_1 \alpha \Gamma_2$.

The sum of the initial reflection from the first discontinuity and all the subsequent multiple reflections transmitted out is given by equation 7:

$$\Gamma_1 + T_1^2 \alpha^2 \Gamma_2 \left(1 - \Gamma_1 \alpha^2 \Gamma_2 + (\Gamma_1 \alpha^2 \Gamma_2)^2 - (\Gamma_1 \alpha^2 \Gamma_2)^3 + \ldots\right) = \Gamma_1 + \frac{T_1^2 \alpha^2 \Gamma_2}{1 + \Gamma_1 \alpha^2 \Gamma_2} \qquad 7$$

The terms in brackets in equation 7 are a convergent geometric series which has then been summated to an infinite number of terms.

This represents the voltage coefficient for the total reflection back to the generator from both discontinuities with the lossy line between them.

Condition 1: When There is No Reflection to the Generator

If the first discontinuity is tuned so that no power returns to the generator then, using equation 7, the voltage reflection coefficient is zero, i.e.

$$\Gamma_1 + \frac{T_1^2 \alpha^2 \Gamma_2}{1 + \Gamma_1 \alpha^2 \Gamma_2} = 0. \qquad 8$$

Then $$\begin{aligned}
\Gamma_1 &= -\frac{T_1^2 \alpha^2 \Gamma_2}{1 + \Gamma_1 \alpha^2 \Gamma_2} \\
&= -T_1^2 \alpha^2 \Gamma_2 - \Gamma_1^2 \alpha^2 \Gamma_2 \\
&= -\alpha^2 \Gamma_2 (T_1^2 + \Gamma_1^2) \\
&= -\alpha^2 \Gamma_2
\end{aligned} \qquad 9$$

This is the expected result, where the two discontinuities, when viewed from the generator, would give exactly opposite displacements of the impedance displayed on a Smith chart, and the reflection from the first discontinuity is smaller than the second because the effect of the second discontinuity is reduced by the attenuation in the transmission line.

The signal that is transmitted past the second discontinuity can be calculated as:

$$T_1 \alpha T_2 \left(1 - \Gamma_1 \alpha^2 \Gamma_2 + (\Gamma_1 \alpha^2 \Gamma_2) - (\Gamma_1 \alpha^2 \Gamma_2)^3 + \ldots \right) = \frac{T_1 \alpha T_2}{1 + \Gamma_1 \alpha^2 \Gamma_2} \qquad 10$$

Because in this example the first discontinuity is tuned so that no power returns to the transmitter, $\Gamma_1 = -\alpha^2 \Gamma_2$ (from equation 9) and the last term in equation 10 can be re-written as:

$$\begin{aligned}
\frac{T_1 \alpha T_2}{1 + \Gamma_1 \alpha^2 \Gamma_2} &= \frac{T_1 \alpha T_2}{1 - \Gamma_1^2} \\
&= \frac{T_1 \alpha T_2}{T_1^2} \\
&= \alpha \frac{T_2}{T_1} \\
&= \alpha \sqrt{\frac{1 - \Gamma_2^2}{1 - \Gamma_1^2}} \\
&= \alpha \sqrt{\frac{1 - \Gamma_2^2}{1 - \alpha^2 \Gamma_2^2}}
\end{aligned} \qquad 11$$

This is the voltage signal transmitted to the tissue and so by squaring, the power that is transmitted is given by equation 12 below:

$$\alpha^2 \frac{1 - \Gamma_2^2}{1 - \alpha^2 \Gamma_2^2} = \frac{1 - \Gamma_2^2}{1/\alpha^2 - \Gamma_2^2} = \frac{\alpha^2 - \Gamma_1^2}{1 - \Gamma_1^2} \qquad 12$$

Because we are considering the 'tuned' case where no power is reflected to the generator, then we can calculate the power absorbed in the transmission line as the power not transmitted past the second discontinuity. Using the second term in equation 12, the power absorbed in the transmission line (the remaining power) is given by equation 13 below:

$$\begin{aligned}
1 - \frac{1 - \Gamma_2^2}{1/\alpha^2 - \Gamma_2^2} &= \frac{1/\alpha^2 - \Gamma_2^2 - 1 + \Gamma_2^2}{1/\alpha^2 - \Gamma_2^2} \\
&= \frac{1/\alpha^2 - 1}{1/\alpha^2 - \Gamma_2^2} \\
&= \frac{1 - \alpha^2}{1 - \Gamma_1^2/\alpha^2}
\end{aligned} \qquad 13$$

The total forward travelling signal immediately after the first discontinuity has amplitude $1/T_1$ and power flow $1/T_1^2$ (this does not allow for loss in the discontinuity itself). These can be larger than one because of the resonant build up of signal in the transmission line between two discontinuities, which can be regarded as a resonant cavity. The backward travelling signal at the same point has amplitude $-\Gamma_1/T_1$ and power flow $\Gamma_1^2/T_1^2$. The difference between these power flows is 1, i.e. all the incident power flows forward because the first discontinuity is tuned to present a match to the transmitter.

Condition 2: When the Discontinuities are of Equal Magnitude

If the first discontinuity is made equal in size to the second discontinuity, then $\Gamma_1 = -\Gamma_2$ and the total transmitted signal can be calculated from equation 10 and given in equation 14:

$$\frac{T_1 \alpha T_2}{1 + \Gamma_1 \alpha^2 \Gamma_2} = \frac{T_1 \alpha T_1}{1 - \Gamma_1 \alpha^2 \Gamma_1} = \frac{\alpha T_1^2}{1 - \alpha^2 \Gamma_1^2} = \frac{\alpha(1 - \Gamma_1^2)}{1 - \alpha^2 \Gamma_1^2} \qquad 14$$

The power transmitted is then given by equation 15:

$$\left(\frac{\alpha(1 - \Gamma_1^2)}{1 - \alpha^2 \Gamma_1^2}\right)^2 \qquad 15$$

The power returned to the transmitter is, from equation 7 given by equation 16:

$$\left(\Gamma_1 + \frac{T_1^2 \alpha^2 \Gamma_2}{1 + \Gamma_1 \alpha^2 \Gamma_2}\right)^2 = \left(\frac{\Gamma_1 - \Gamma_1^3 \alpha^2 - T_1^2 \alpha^2 \Gamma_1}{1 - \Gamma_1^2 \alpha^2}\right)^2 \qquad 16$$

$$= \left(\frac{\Gamma_1(1 - \Gamma_1^2 \alpha^2 - T_1^2 \alpha^2)}{1 - \Gamma_1^2 \alpha^2}\right)^2$$

$$= \left(\frac{\Gamma_1(1 - \alpha^2)}{1 - \Gamma_1^2 \alpha^2}\right)^2$$

because by definition $T_1^2 + \Gamma_1^2 = 1$ as no loss is considered within the discontinuity.

The power absorbed in the transmission line (the remaining power) is then given by equation 17 below:

$$1 - \left(\frac{\Gamma_1(1-\alpha^2)}{1-\Gamma_1^2 \alpha^2}\right)^2 - \left(\frac{\alpha(1-\Gamma_1^2)}{1-\Gamma_1^2 \alpha^2}\right)^2 = \frac{(1-\Gamma_1^2)(1-\alpha^2)(1+\alpha^2 \Gamma_1^2)}{(1-\Gamma_1^2 \alpha^2)^2} \qquad 17$$

The signal travelling forward after the first discontinuity is given by equation 18 below:

$$\frac{\sqrt{1 - \Gamma_1^2}}{1 - \Gamma_1^2 \alpha^2} \qquad 18$$

and the signal travelling backward to the first discontinuity is given by equation 19:

$$\frac{-\Gamma_1 \alpha^2 \sqrt{1 - \Gamma_1^2}}{1 - \Gamma_1^2 \alpha^2}. \qquad 19$$

A general equation for the reflection from the tuner and probe with a line between them has been derived (equation 7). Two 'matching' situations have been explored, one in which no power is reflected back to the transmitter (the tuner impedance is the complex conjugate of the tuner impedance seen through the lossy transmission line), and the other in which the tuner reactance is the complex conjugate of the probe impedance. The two cases are examined in order to represent the results that would occur from different tuning techniques. Measurement of the probe impedance can be made through the cable to obtain the complex reflection of the combined effect and, as indicated above, used to set the tuner. Other methods can involve numerically removing the known loss of the transmission line from the measurement before tuning, or alternatively setting the tuner to pre-determined values to correspond to different types of tissue, these types having been identified using the systems' measurement mode. From equations 13 and 17 it can be seen that, as expected, low values of attenuation ($\alpha$ close to 1) results in the lowest losses in the transmission line. However, the other terms in the equations show that for constant attenuation in the line, the losses are lowest when the reflection from the first discontinuity (the tuner) is smallest ($\Gamma_1$ is close to zero). This means that in these low-loss situations the reflection from the probe will also be small ($\Gamma_2$ is close to zero) in both the cases considered. This means that the lowest losses in the transmission line occur when the probe is matched. If the probe is not matched, stored power builds up in the transmission line and there are associated higher losses. For this reason it is recommended that for the design of the probe, the probe should be pre-matched to typical electrical properties of the tumour. In this way little or no tuning is required during the ablation process when the power is high. For this reason the present design of the probe was developed to have a good match into tumour, with progressively poorer matches into fat and air, which are to be identified using low power during the measurement mode. In cases when ablation is to be carried out at lower powers, the higher losses (proportionally) incurred in the transmission line as a result of the necessary tuning are not a significant problem.

The effect of the mismatch and attenuation on the transmitted power and the loss in the transmission line are shown in the figures that follow. On each graph the reflection amplitude at the end of the probe ($\Gamma_2$) varies from 0 to 1 across the horizontal axis, and curves are drawn for values of the one-way loss in the transmission line ($10 \log(\alpha^2)$) from 0.1 dB to 3 dB as the parameter:

For each situation evaluated a pair of graphs is provided. The first graph shows the predicted behaviour for the case when no power is reflected back to the transmitter ($\Gamma_1 = \alpha^2 \Gamma_2$), and the second graph shows the predicted behaviour for the case when the probe and the tuner have conjugate reflection coefficients ($\Gamma_1 = \Gamma_2$).

Figure 32B:
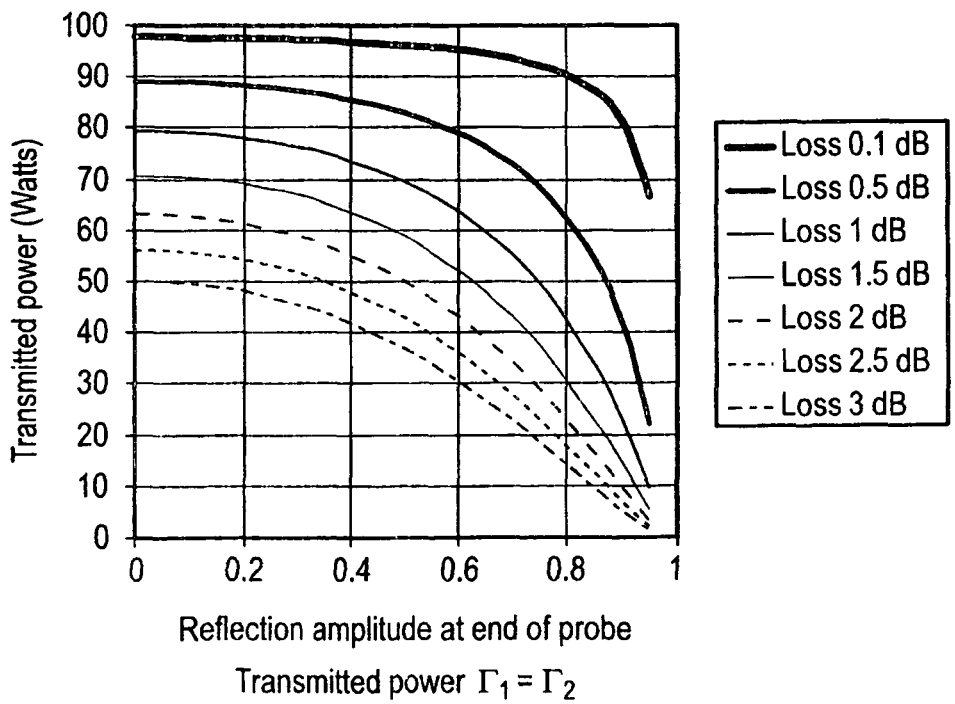
Figure 33A:
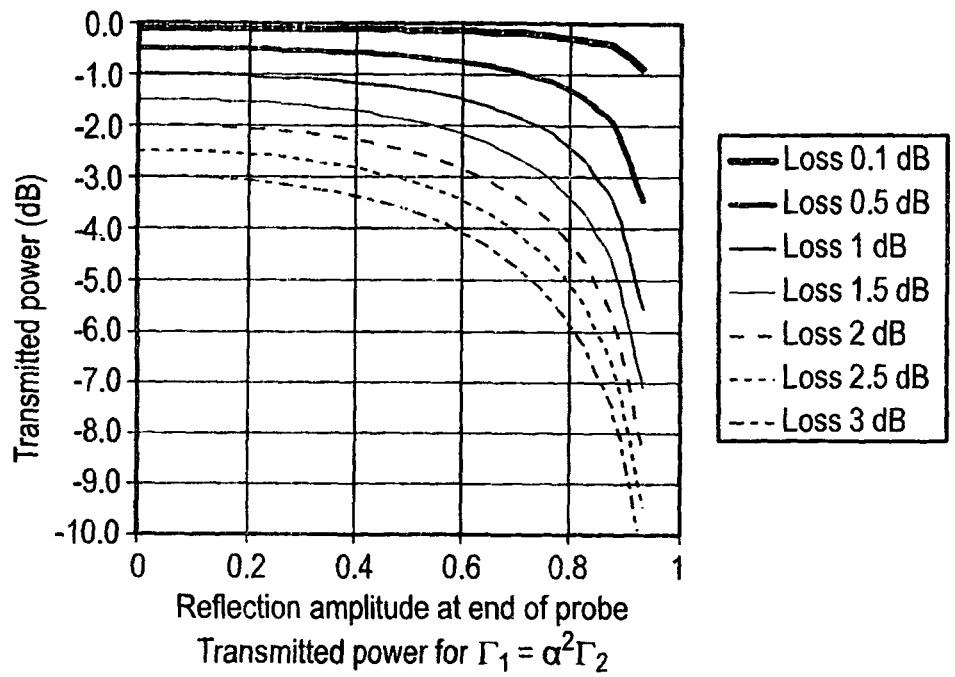
Figure 33B:
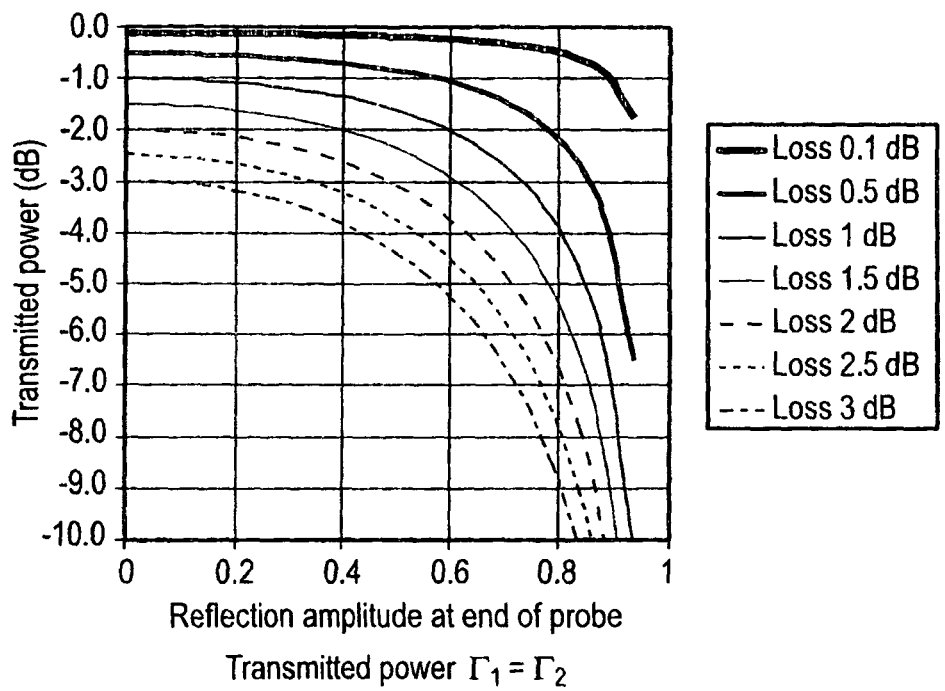

FIG. 32 shows the power transmitted to the tissue when 100 Watts is incident at the tuner. FIG. 33 also show this as the reduction in power expressed in dB. As expected, the graphs show that at low reflection coefficient the losses incurred correspond approximately to those of the transmission line and represents the situation where the inherent impedance of the probe is close to that of the tissue. For this case, few multiple reflections, each way along the transmission line, occur. However, it is seen that as the reflection increases in value, the losses also increase, and these are due to the larger number of transits of the wave, each undergoing attenuation. The benefits of designing the probe to be pre-matched to the characteristics of the tissue to be ablated, in this case a tumour, are immediately shown.

It is apparent from the above that under the conditions when tuning is necessary, the larger the mismatch to be compensated then the poorer will be the efficiency of the power transfer to the tissue. The benefits to be gained by installing a tuner into the system should therefore be examined. This can be assessed by calculating the power transmitted to the tissue in the absence of a tuner, only the transmission line and the probe will be in the circuit. The forward power will be given by $\alpha^2(1-\Gamma_2^2)$.

Figure 34A:
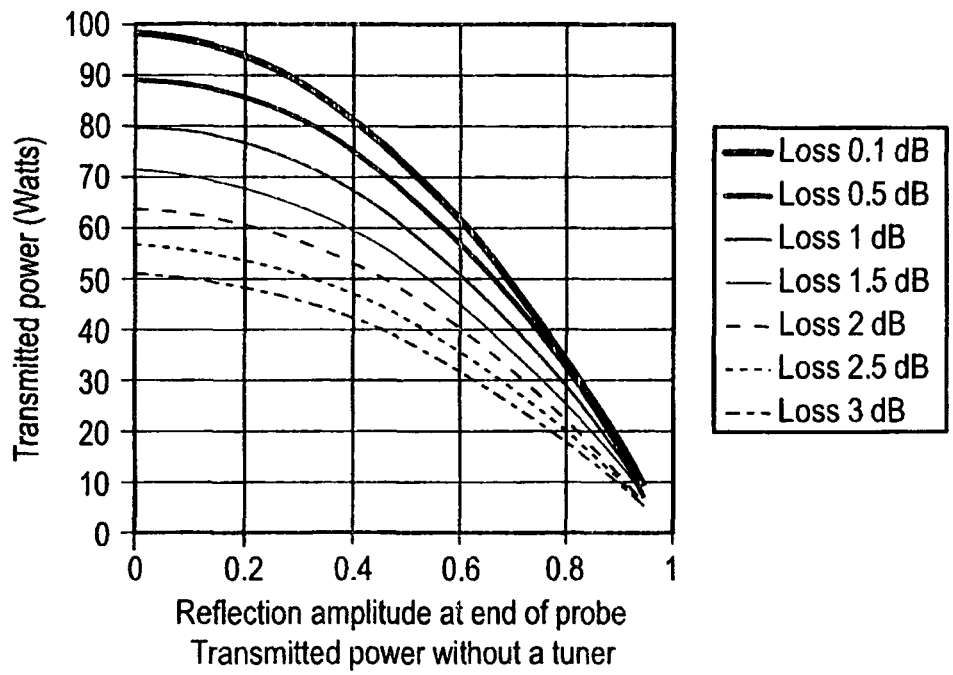
Figure 34B:
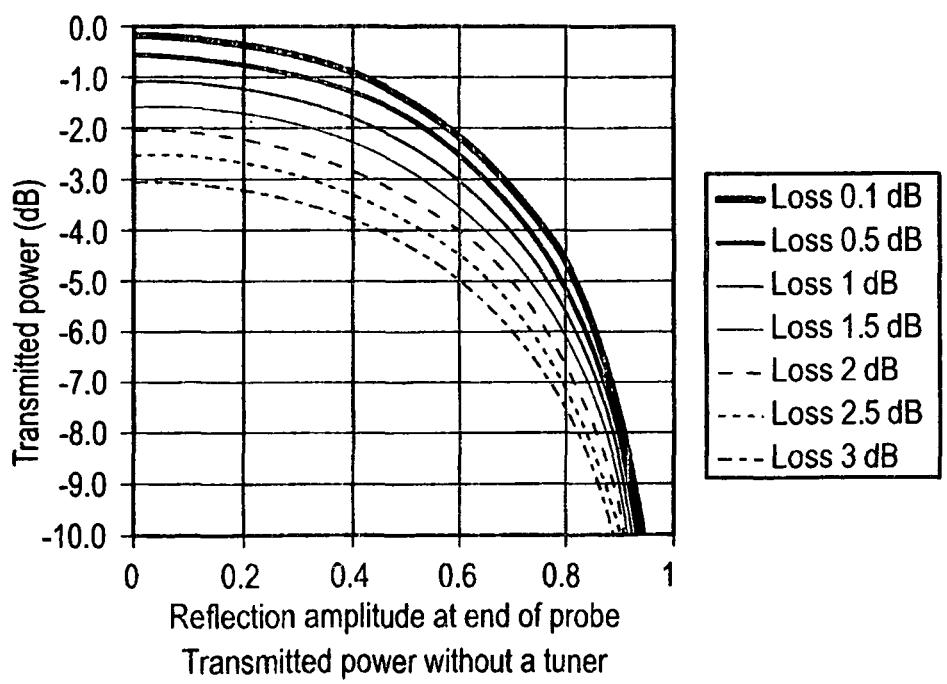

Again for 100 Watts of microwave power supplied from the generator, the power delivered to the tissue is plotted against the probe reflection coefficient for various values of cable loss. FIG. 34A shows this power in Watts while in FIG. 34B the loss compared to the input power supplied by the generator is shown in dB. Comparing these with FIGS. 32 and 33 it is immediately apparent that as the reflection approaches unity, a more rapid decrease in power is experienced when the tuner is absent. This is particularly noticeable at the lower values of cable loss. It is informative to examine a specific case and it is expected that in practice the losses in the transmission line will be in the region of 2 dB while the best that might be achieved could be 1.5 dB. Taking the example of 1.5 dB loss in the transmission line and comparing FIG. 32A with FIG. 34A at a reflection coefficient of 0.8, approximately 47 Watts is passed to the tissue when the tuner is deployed while only 25.5 Watts would be emitted without the use of a tuner.

Figure 35A:
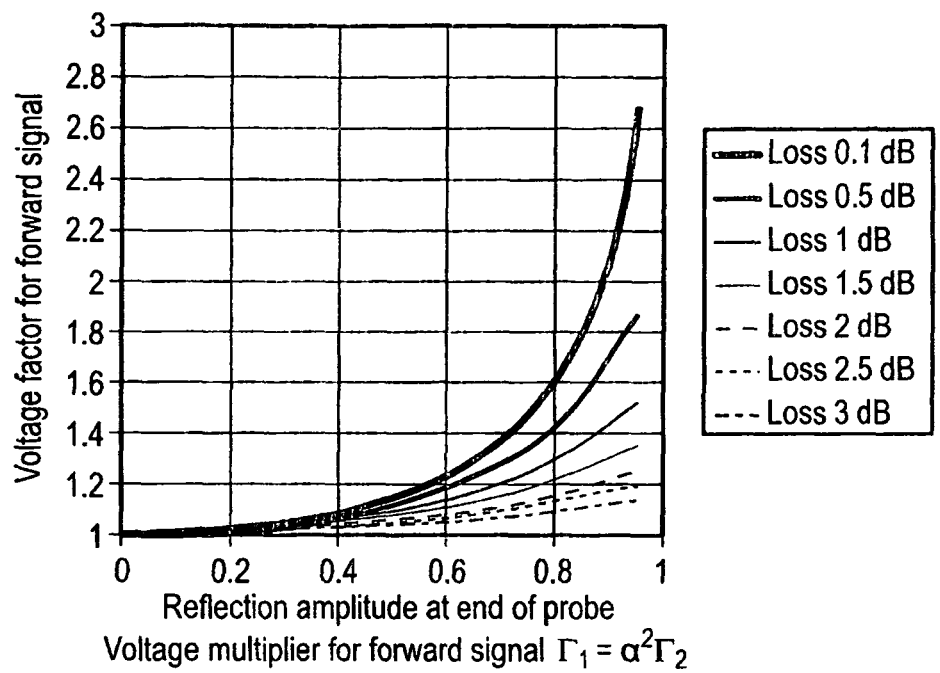
Figure 35B:
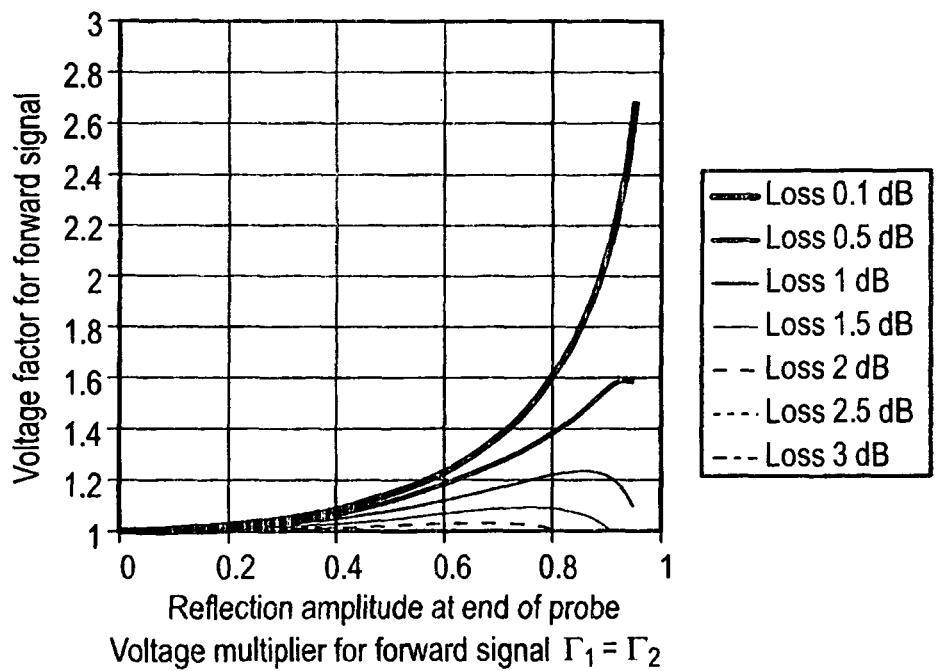
Figure 36A:
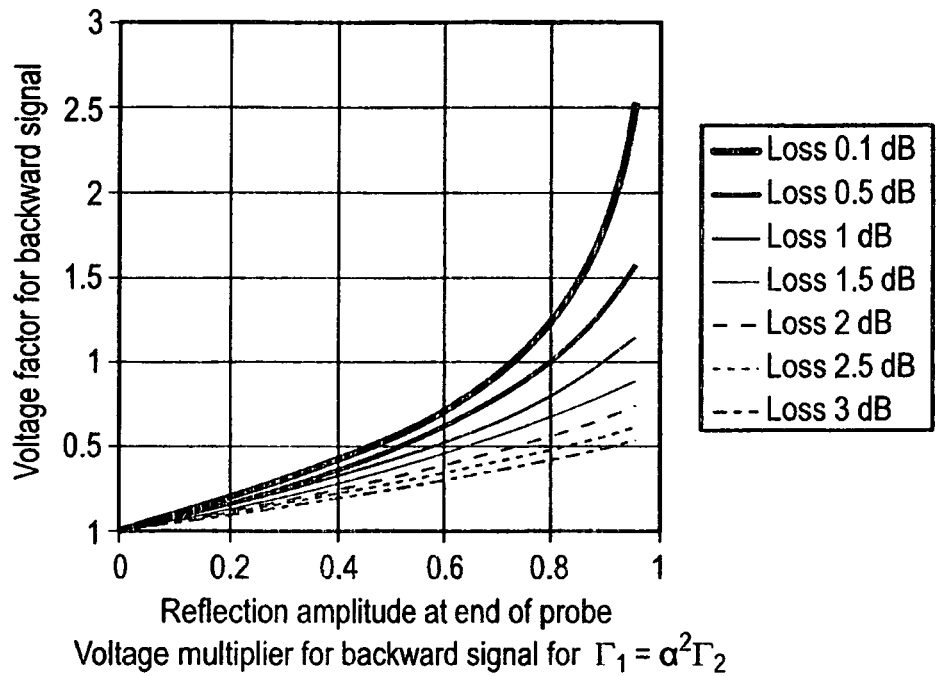
Figure 36B:
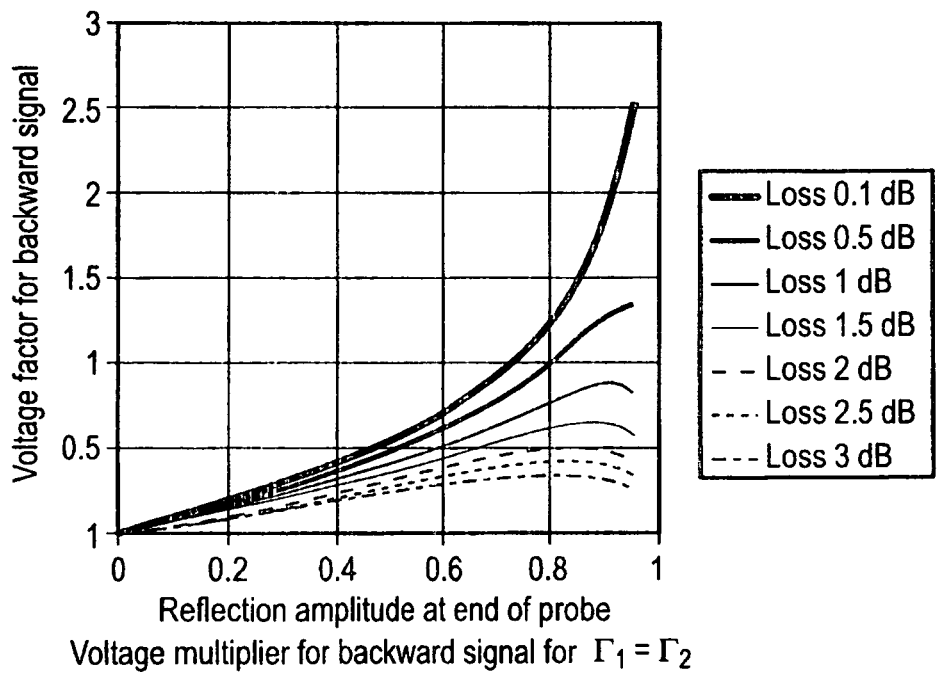

FIG. 35 shows the multiplication of the voltage for the forward travelling wave immediately after the tuner, and FIG. 36 shows the multiplication of the voltage for the backward travelling wave immediately after the tuner. It is seen from the curves that the situations where no power is returned to the generator yield the higher voltages, and so to examine the worst cases we observe FIG. 35A and FIG. 36A for, again, a single transit loss of 1.5 dB. Extrapolating these curves on the two graphs to the limit of the refection coefficient equal to one, the forward travelling wave has a voltage multiplication factor close to 1.4 at the tuner while the voltage for the backward travelling wave at the tuner is approximately equal to that in the incident wave. For a maximum input power of 100 Watts, the RMS voltage occurring in waveguide 17 at 14.5 GHz will be in the region of 212 Volts RMS, 300 Volts peak, hence 1.4 times this, i.e. approximately 420 Volts, might be expected. This supplies a limiting value for the requirements to be set for the waveguide components in proximity to the tuner; i.e. the tuner itself and the waveguide directional couplers.

Figure 37A:
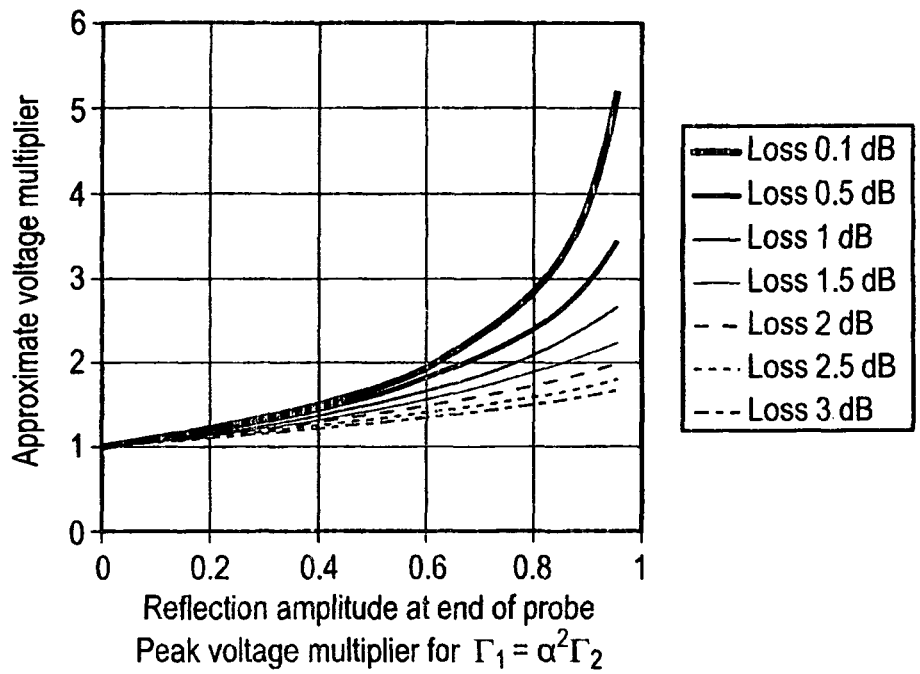
Figure 37B:
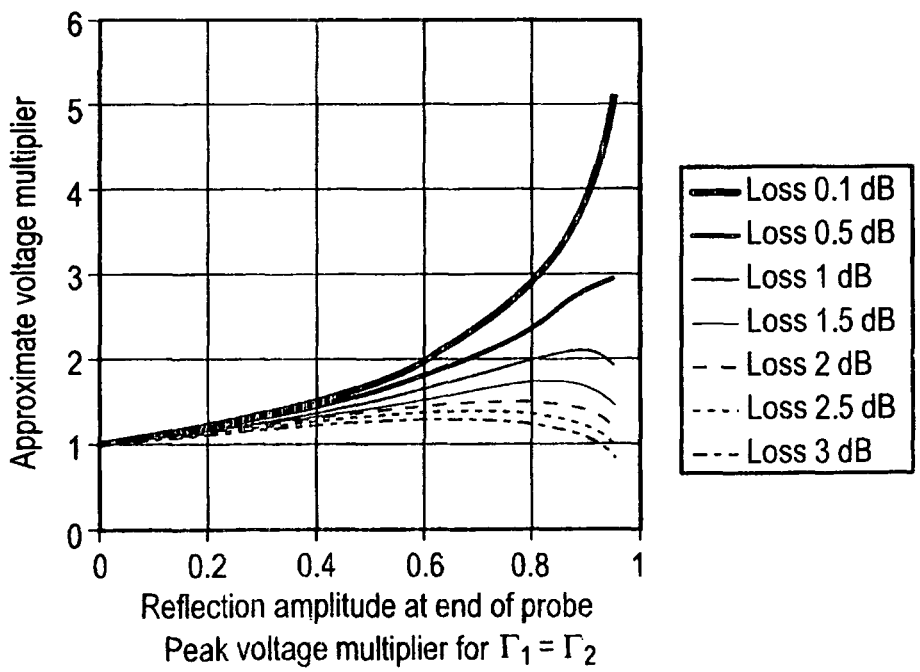
Figure 38A:
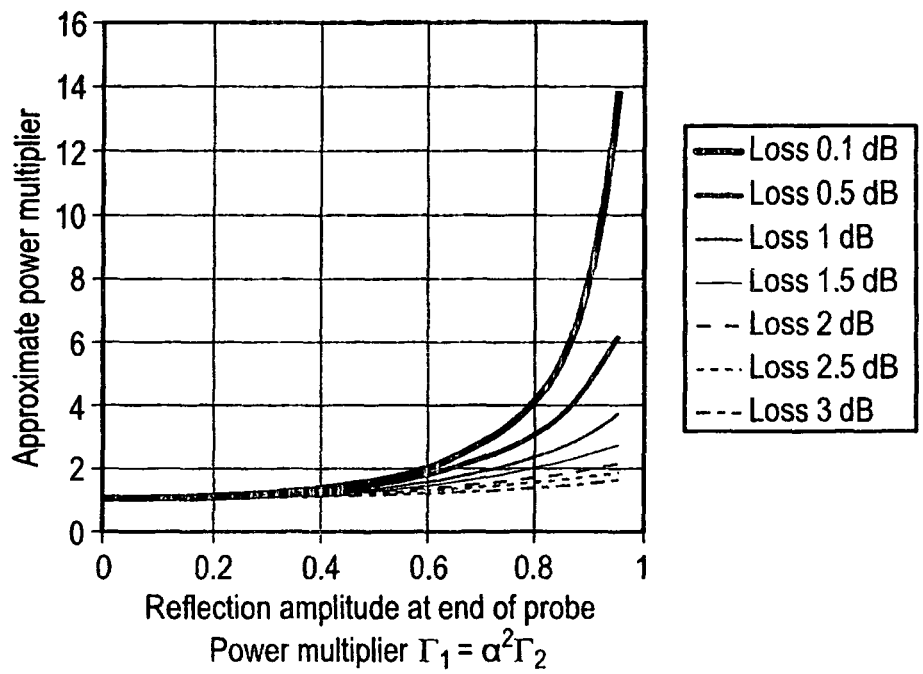
Figure 38B:
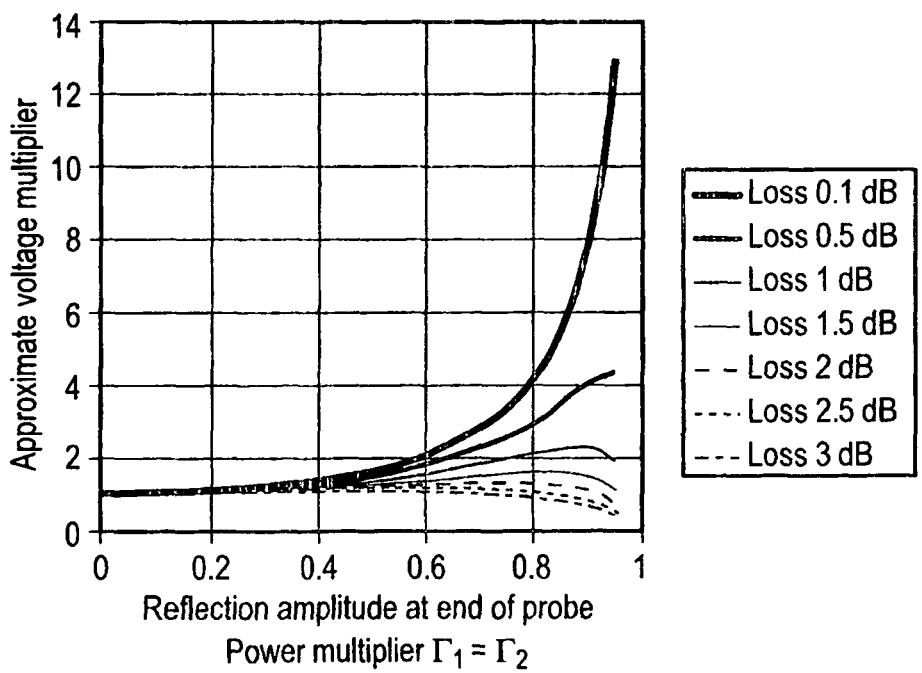

FIG. 37 shows the peak voltage possible due to the standing wave. This is the sum of the voltages of the forward and backward waves at the point where the forward wave is largest, i.e. next to the first discontinuity (the tuner). FIG. 38 shows the peak of the sum of the powers for the forward and backward travelling waves. This indicates the potential for generation of local heating of components.

The peak voltage that can occur in the transmission line is an important parameter to determine because it will have an impact on the performance necessary for other circuit elements in the transmission line, namely the coaxial components such as the waveguide to coaxial transition and the connectors. As shown_previously, examination of the figures shows that with the system tuned for zero return to the generator, higher voltages and powers are created. The worst cases are therefore shown by FIG. 37A and FIG. 38A where we will again observe the plots for a one way loss of 1.5 dB. Extrapolating the curve in FIG. 37A to unity reflection coefficient, a voltage multiplication of approximately 2.4 is obtained. In a 50 Ohm coaxial line this will lead to peak voltages close to 170 Volts when 100 Watts is incident at the tuner. Once again this value provides a limiting condition for the specification of the coaxial components. Similarly FIG. 38A shows that local heating may also be increased by a factor of 3.3.

A mathematical analysis has been carried out to describe the conditions that occur when a microwave tuner unit is used to 'match' a 'probe' aerial that is remotely placed at the far end of a lossy transmission line. The combined impedance of the probe and a tissue medium in which it is embedded can vary, and in general will be different from the impedance of the transmission line and the microwave generator. The mathematical formulations account for the interaction of the electromagnetic waves that reflect between the tuner and the mismatched probe in the tissue, and for a standing wave that can be set up in the transmission line.

It has been shown that when the impedance of the probe differs from that of the generator then significantly more microwave power can be transferred to the tissue through the use of a tuner unit. However, it has also been shown that optimum transmission occurs when the impedance of the probe—tissue combination is equal to that of the generator. It is therefore_advisable that information should be obtained for the complex impedance of the tissue type that the probe is primarily to be used to ablate. Probes should preferably be designed to be internally matched to that impedance. Under such conditions maximum power will be available for ablation without any discontinuity introduced by the tuner. The function of the tuner will be to attain the best possible power transfer when the tissue conditions are other than those designed for.

Equations have been set out to analyse the situations whereby the tuner is set up to cancel all reflections from the cable and probe, and also the situation when the tuner exactly matches the impedance conditions found at the probe. These two cases have been evaluated to account for different techniques by which the tuner might be controlled. It is seen that higher powers are coupled to the tissue when then tuner is to set the complex conjugate of the match that is formed by the combined effect of the cable with the probe.

Graphs have been plotted that show the levels of microwave power that can be delivered to a patient for a range of different reflective conditions that will occur at the probe. Included in the analysis is the effect that different levels of loss present in the cable will have on the transmitted power. As is expected higher powers are transferred at lower cable losses. However, it has also been shown that at lower cable losses the action of the tuner is notably more effective in maintaining good power transfer at high probe mismatch conditions. This emphasises the advantages of a low loss transmission line, and so with future advances in cable technology, a single probe design can be more effective over a wider range of tissue properties.

Also calculated and presented in graphical form are the voltages that build up at the tuner and the peak of the voltages that can occur in the standing wave. The importance of these graphs is that the numerical values calculated enable the conditions under which the components in the circuit are to operate to be specified. In addition, heating effects can be estimated from this analysis.

The invention claimed is:

1. Calibration apparatus for an antenna that is arranged to emit microwave radiation from an emitting region thereof, the apparatus having: a loading arrangement adapted to subject the emitting region of the antenna to a plurality of impedances, each impedance having a known value for a predetermined frequency of microwave radiation, a detector arranged to measure the magnitude and phase of microwave radiation having the predetermined frequency that is emitted from the antenna and reflected from the loading arrangement, and a processing unit configured to generate calibration data for the antenna, wherein the plurality of impedances are repeatably selectable from a continuous range of impedances, and wherein the antenna is used subsequently to measure magnitude and phase of microwave radiation having the predetermined frequency reflected from an unknown load at the emitting region of the antenna, the calibration data is usable to convert the measured magnitude and phase to be representative of the unknown load.

2. Calibration apparatus according to claim 1, wherein the loading arrangement includes a substantially lossless waveguide cavity between a first end adapted to receive the emitting region of the antenna and a second end, and wherein the apparatus includes an actuator arranged to slide the second end relative to the first end to vary a distance between the first end and the second end.

3. Calibration apparatus according to claim 2, wherein the cavity is electrically connectable to the antenna and the second end is electrically connected to the cavity.

4. Calibration apparatus according to claim 1, including at least one radio frequency (RF) choke arranged to provide an electrical connection between the cavity and antenna and/or between the cavity and the second end.

5. Calibration apparatus according to claim 1, wherein the continuous range of impedances includes 0Ω (short circuit) and ∞Ω (open circuit).

6. Calibration apparatus according to claim 1, wherein the loading arrangement is adapted to permit generation of calibration data for two or more different frequencies of microwave radiation.

7. A combination of calibration apparatus according to claim 1, and an antenna arranged to emit microwave radiation from an emitting region thereof, wherein at least the emitting region of the antenna and the loading arrangement are packaged together in a sterile environment.

8. A method of calibrating an antenna that is arranged to emit microwave radiation from an emitting region thereof, the method including:
　selecting an impedance to be exhibited by a loading arrangement, the loading arrangement being capable of exhibiting any impedance in a continuous range of impedances, a plurality of impedances being repeatably selectable from the continuous range of impedance, each of the plurality of impedances having a known value for a predetermined frequency of microwave radiation;
　subjecting the emitting region of the antenna to the selected impedance; emitting microwave radiation having the predetermined frequency through the antenna;
　measuring the magnitude and phase of the emitted microwave radiation that is reflected from the loading arrangement; generating calibration data for the antenna from the magnitude and phase measured;
　repeating the above steps for each of one or more different impedances selected from the plurality of impedances;
　whereby, the antenna is used subsequently to measure magnitude and phase of microwave radiation having the predetermined frequency with an unknown load at the emitting region of the antenna, the calibration data for the different impedances is usable to convert the measured magnitude and phase to be representative of the unknown load.

9. A method of calibrating a surgical probe having an antenna arranged to emit a microwave radiation field at a predetermined frequency from an emitting region thereof, the method comprising:
　sequentially immersing the antenna in each of three or more flowable calibration standards, each calibration standard having a different impedance value selected from a range of complex impedances at the predetermined frequency;
　detecting the magnitude and phase of microwave radiation reflected from the probe when presented to each calibration standard to determine a measured impedance value for each calibration standard; and
　comparing the measured impedance values with reference impedance values for each standard to determine a mapping function for transforming subsequent measured impedance values; wherein, the antenna is used subsequently to measure magnitude and phase of microwave radiation having the predetermined frequency with an unknown load at the emitting region of the antenna, the calibration data for the different impedances is usable to convert the measured magnitude and phase to be representative of the unknown load.

10. A method according to claim 9, wherein one of the flowable calibration standards is air.

11. A method according to claim 9, including selecting an impedance value for each of the calibration standards from a continuous range of complex impedances.

12. A method according to claim 9, wherein the calibration standards include two or more mixtures containing varying proportions of two or more materials which have differing impedances for microwave radiation at the predetermined frequency.

13. A method according to claim 12, wherein the two or more materials include ethanol and de-ionised water.

14. A method according to claim 9, wherein the calibration standards have complex impedances at the predetermined frequency that include real components spread between 0.5 and 2.0.

15. A method according to claim 9, wherein the reference impedance values for each calibration standard are measurements taken using a reference probe or the absolute impedance values of the calibration standards.

* * * * *